United States Patent
Hunt et al.

(10) Patent No.: US 12,205,719 B2
(45) Date of Patent: Jan. 21, 2025

(54) HEALTH MANAGEMENT SYSTEM

(71) Applicant: Big Sky Labs, Inc., Everett, WA (US)

(72) Inventors: Dave Hunt, Tulalip, WA (US); Dan Stone, Issaquah, WA (US); Eric Paul, Newberg, OR (US); Dan Preston, Bainbridge Island, WA (US); Rigel Correa, Bainbridge Island, WA (US); Jessica Milanio, Tacoma, WA (US); Lindsey Atkinson, Port Orchard, WA (US); John Gibson, Federal Way, WA (US); Benjamin Cheek, Bremerton, WA (US); John Friar, Bellevue, WA (US); Lucas Cheek, Bremerton, WA (US)

(73) Assignee: Big Sky Labs, Inc., Everett, WA (US)

( * ) Notice: Subject to any disclaimer, the term of this patent is extended or adjusted under 35 U.S.C. 154(b) by 375 days.

(21) Appl. No.: 17/306,594

(22) Filed: May 3, 2021

(65) Prior Publication Data

US 2021/0343404 A1   Nov. 4, 2021

Related U.S. Application Data

(60) Provisional application No. 63/019,935, filed on May 4, 2020, provisional application No. 63/091,223, filed on (Continued)

(51) Int. Cl.
*G16H 40/67* (2018.01)
*G16H 20/13* (2018.01)
*G16H 80/00* (2018.01)

(52) U.S. Cl.
CPC ............. *G16H 40/67* (2018.01); *G16H 20/13* (2018.01); *G16H 80/00* (2018.01)

(58) Field of Classification Search
CPC ......... G16H 40/67; G16H 20/13; G16H 80/00
(Continued)

(56) References Cited

U.S. PATENT DOCUMENTS 6,997,455 B2 * 2/2006 Romine ................ B65H 9/002
                                                    271/227
7,654,261 B1 * 2/2010 Rockhold .............. A61B 50/13
                                                    128/202.13

(Continued)

FOREIGN PATENT DOCUMENTS

EP       2757537 A1 *  7/2014  ........... A61J 7/0076
JP    2020014599 A     1/2020
(Continued)

OTHER PUBLICATIONS

The International Preliminary Report on Patentability mailed Nov. 17, 2022 for PCT Application No. PCT/US2021/030486, 6 pages.
(Continued)

*Primary Examiner* — Rakesh Kumar
(74) *Attorney, Agent, or Firm* — Lee & Hayes, P.C.

(57) ABSTRACT

Described herein is an integrated health management system, and method that includes a pre-packaged tablet delivery apparatus configured to deliver pre-packaged tablets to a user. The delivery apparatus comprising an alignment guide, a processor modulated differential drive used for the directional control of the pre-packaged tablets, a sensor for sensing a location and an orientation of the pre-packaged tablet, a cutter mechanism, and cutter mechanism control logic. The sensed location and orientation of the pre-packaged tablet is used to modulate the differential drive. The cutter mechanism control logic is configured to monitor the sensed pre-packaged tablet location and orientation, then initiate a cutting sequence responsive to at least one of the predetermined configuration within the processor and the dynamic configuration responsive to determining an optimal (Continued)

sensed location and orientation. The control logic generates and logs a message into the distributed database responsive to the cutting sequence.

23 Claims, 26 Drawing Sheets

Related U.S. Application Data on Oct. 13, 2020, provisional application No. 63/148,071, filed on Feb. 10, 2021.

(58) Field of Classification Search
USPC .......................................................... 221/30
See application file for complete search history.

(56) References Cited

U.S. PATENT DOCUMENTS

| | | | | |
|---|---|---|---|---|
| 7,828,147 | B2* | 11/2010 | Caracciolo | A61J 7/0084 |
| | | | | 206/530 |
| 7,963,201 | B2* | 6/2011 | Willoughby | G07F 17/0092 |
| | | | | 83/210 |
| 9,931,174 | B2* | 4/2018 | Machado | A61B 42/40 |
| 12,040,066 | B1* | 7/2024 | Weiss | G16H 40/20 |
| 2007/0016443 | A1* | 1/2007 | Wachman | G16H 20/10 |
| | | | | 600/300 |
| 2014/0346184 | A1* | 11/2014 | Bae | A61J 7/0445 |
| | | | | 221/7 |
| 2015/0083742 | A1* | 3/2015 | Choi | B65B 69/0058 |
| | | | | 221/7 |
| 2015/0112703 | A1* | 4/2015 | Sysko | G06Q 10/10 |
| | | | | 705/2 |
| 2015/0216413 | A1* | 8/2015 | Soyao | H04L 67/12 |
| | | | | 709/204 |
| 2016/0042151 | A1* | 2/2016 | Akdogan | B25J 19/023 |
| | | | | 700/240 |
| 2016/0324727 | A1 | 11/2016 | Waugh et al. | |
| 2018/0028409 | A1* | 2/2018 | Doshi | A61J 7/0418 |
| 2018/0096175 | A1* | 4/2018 | Schmeling | G06F 1/3206 |
| 2018/0240536 | A1* | 8/2018 | Bostic | G16H 10/60 |
| 2018/0240539 | A1* | 8/2018 | Doherty | G16H 20/10 |
| 2020/0145997 | A1* | 5/2020 | Luo | H04W 16/02 |
| 2021/0202103 | A1* | 7/2021 | Bostic | G16H 50/80 |
| 2021/0343404 | A1* | 11/2021 | Hunt | G16H 10/60 |
| 2023/0087658 | A1* | 3/2023 | Wheeler | B65G 47/64 |
| | | | | 414/267 |

FOREIGN PATENT DOCUMENTS

| | | | |
|---|---|---|---|
| KR | 20090121265 A | * | 11/2009 |
| KR | 102077599 B1 | | 2/2020 |

OTHER PUBLICATIONS

Extended European Search Report mailed Apr. 5, 2024 for European Application No. 201799491.2, a foreign counterpart to U.S. Appl. No. 17/306,594, 8 pages.

* cited by examiner

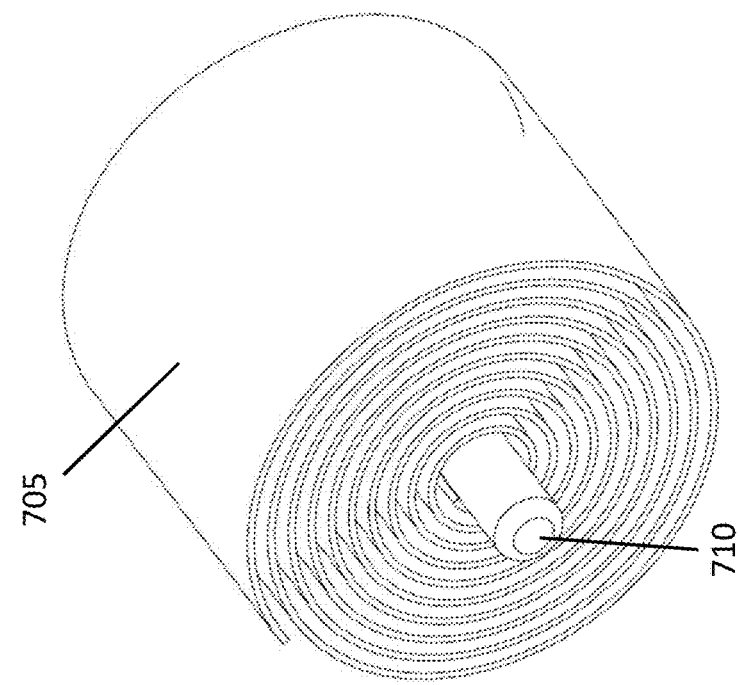
FIG 5B
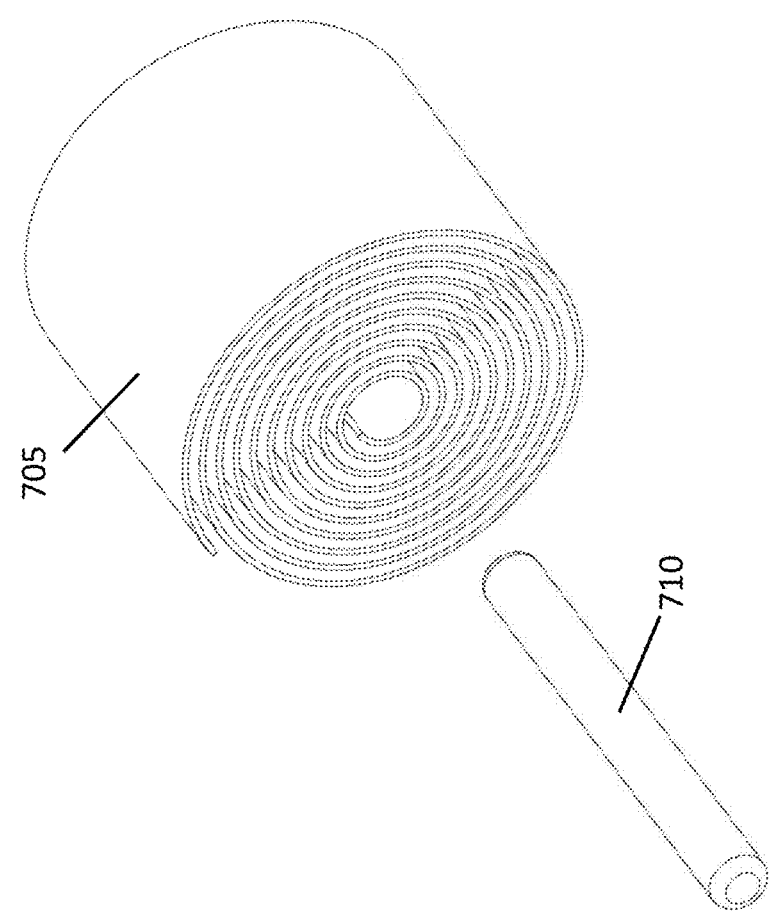
FIG 5A
FIG 5

FIG 10
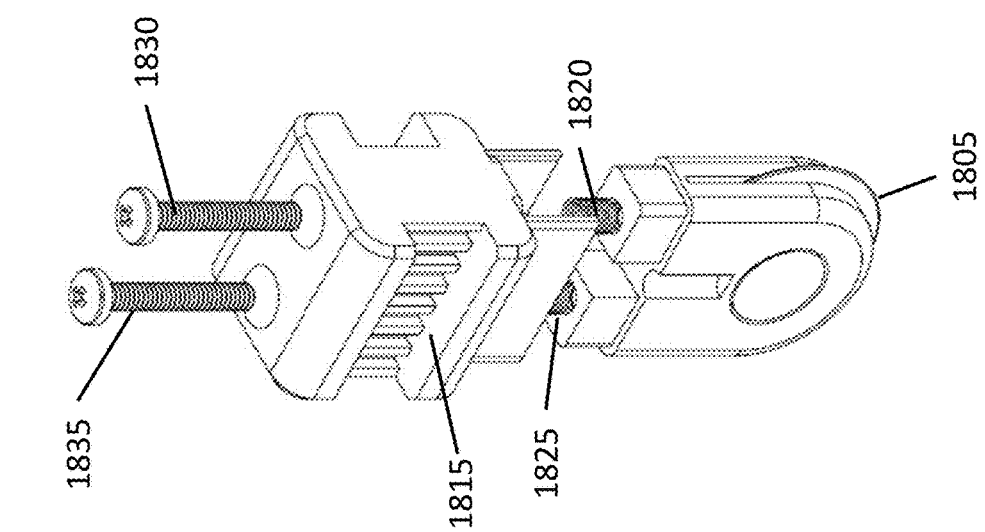
FIG 10A
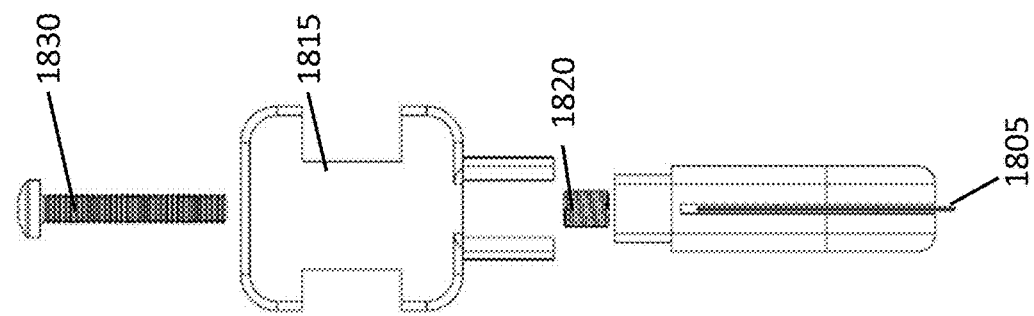
FIG 10B
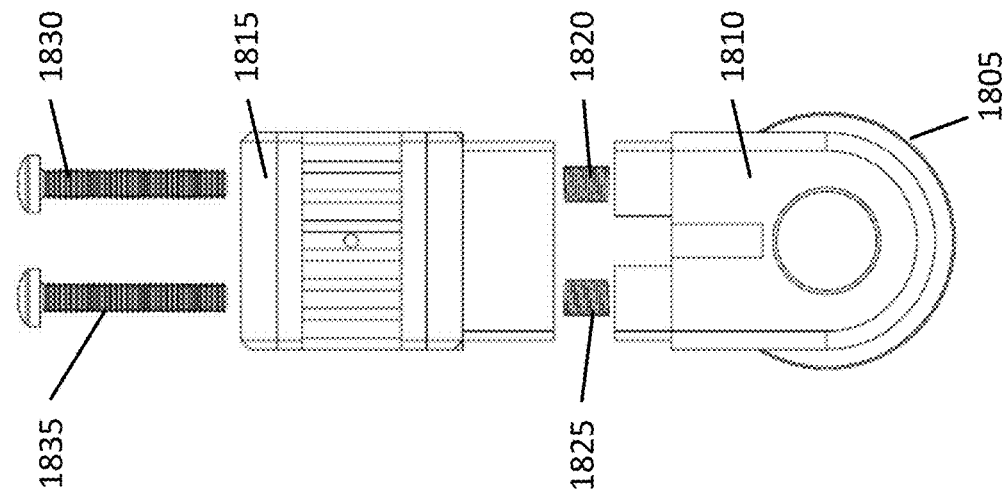
FIG 10C

FIG 11
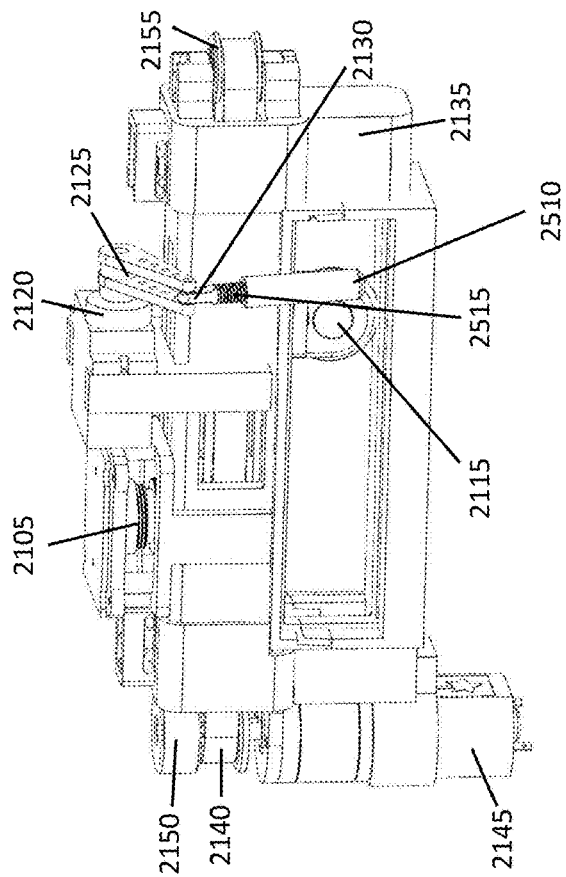
FIG 11B
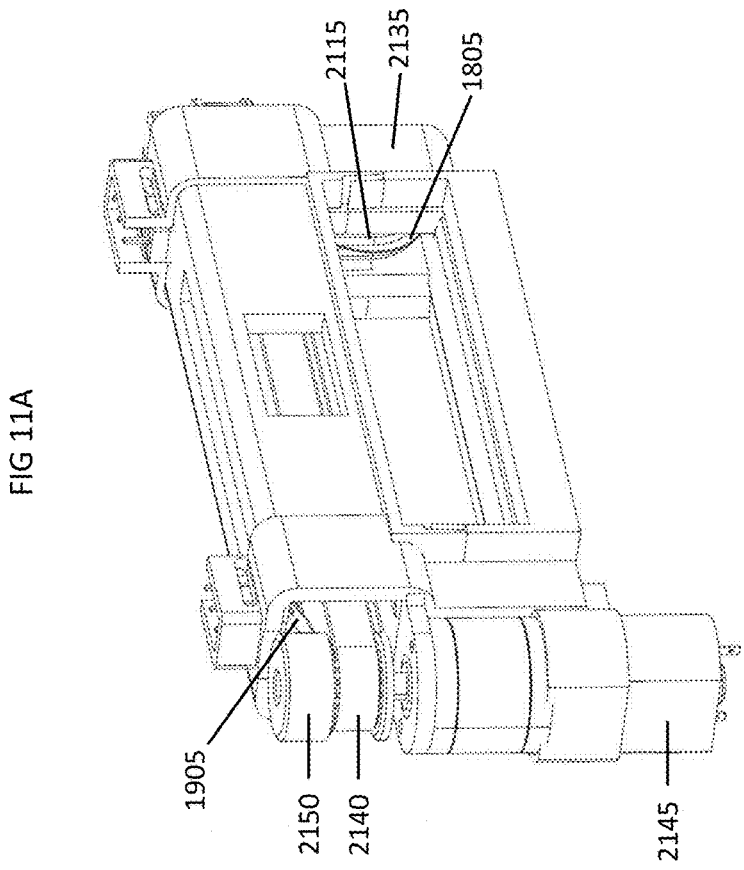
FIG 11A

FIG 16
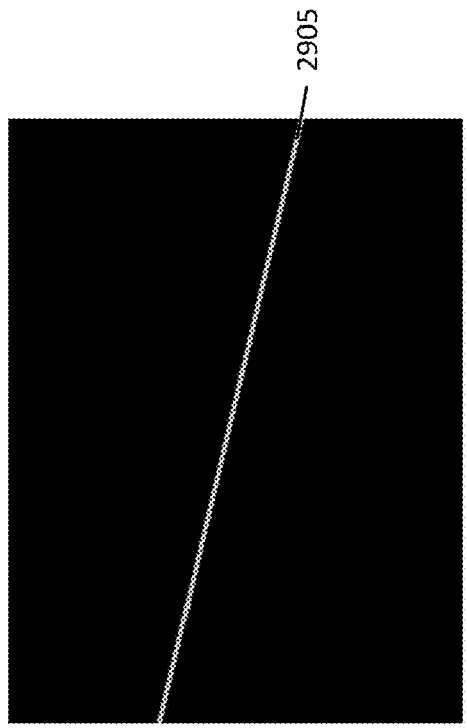
FIG 16C
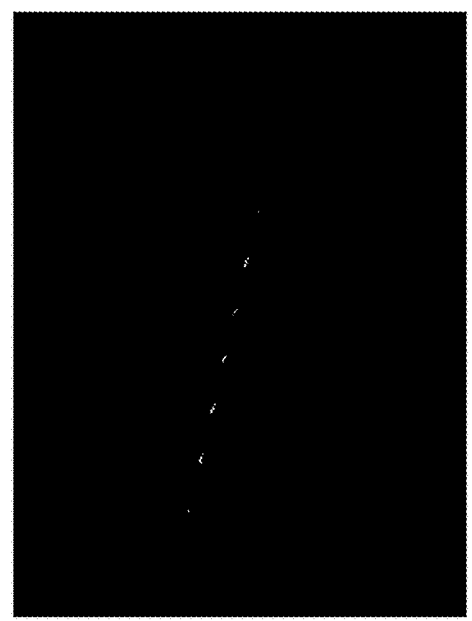
FIG 16D
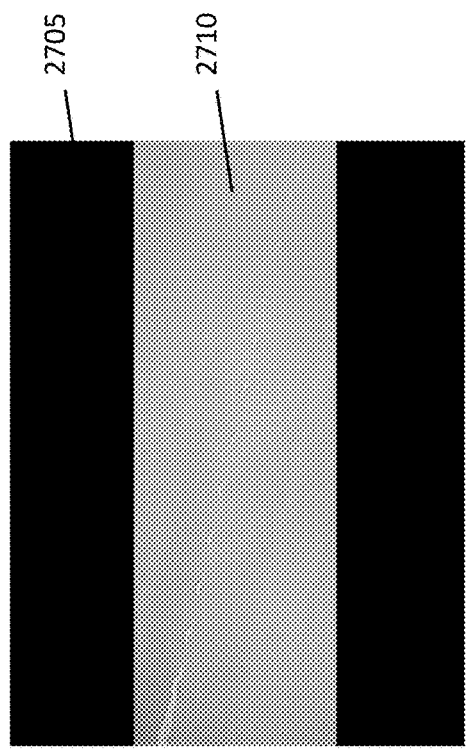
FIG 16A
FIG 16B

HEALTH MANAGEMENT SYSTEM

CROSS REFERENCE TO RELATED APPLICATIONS

The present application claims priority to U.S. Provisional Application No. 63/019,935, entitled "A TELEHEALTH PORTAL FOR THE COLLECTION AND COMMUNICATION OF HEALTH DATA AND MEDICATION COMPLIANCE," filed May 4, 2020, U.S. Provisional Application No. 63/091,223, entitled "A TELEHEALTH PORTAL FOR THE COLLECTION AND COMMUNICATION OF HEALTH DATA AND MEDICATION COMPLIANCE", filed Oct. 13, 2020, and U.S. Provisional Application No. 63/148,071, entitled "A TELEHEALTH PORTAL FOR THE COLLECTION AND COMMUNICATION OF HEALTH DATA AND MEDICATION COMPLIANCE," filed Feb. 10, 2021, which are herein incorporated by reference in their entirety.

TECHNICAL FIELD

This invention relates generally to a health management system for gathering and communicating certain health data related to a patient and data regarding their scheduled medications.

BACKGROUND

In an increasingly digital world, the rapid rise of Telehealth has necessitated new technological answers to previously, routinely held practices; pen and paper replaced by electronic forms, in-person meetings replaced by video conferencing, in-store purchases replaced by ecommerce and same-day shipping. Many activities are quickly migrating online, especially in the wake of the highly infectious and dangerous Coronavirus which disrupted the natural flow of the healthcare industry. Health care providers are now introducing and leaning upon new methods of administering the same level of care in an environment that no longer relies on a high level of close, interpersonal interaction.

Telehealth is broadly defined as the distribution of health-related services and information via electronic information and telecommunication technologies. It allows long-distance patient and clinician contact, care, advice, reminders, education, intervention, monitoring, and remote admissions. Telemedicine is sometimes used as a synonym or is used in a more limited sense to describe remote clinical services, such as diagnosis and monitoring. When rural settings, lack of transport, a lack of mobility, decreased funding, or a lack of staff restrict access to care, telehealth may bridge the gap as well as provider distance-learning; meetings, supervision, and presentations between practitioners; online information and health data management and healthcare system integration. Telehealth could include two clinicians discussing a case over video conference; a robotic surgery occurring through remote access; physical therapy done via digital monitoring instruments, live feed and application combinations; tests being forwarded between facilities for interpretation by a higher specialist; home monitoring through continuous sending of patient health data; client to practitioner online conference; or even videophone interpretation during a consult.

Telehealth is sometimes discussed interchangeably with telemedicine, the latter being more common than the former. The Health Resources and Services Administration distinguishes telehealth from telemedicine in its scope, defining telemedicine only as describing remote clinical services, such as diagnosis and monitoring, while telehealth includes preventative, promotive, and curative care delivery. This includes the above-mentioned non-clinical applications, like administration and provider education.

The United States Department of Health and Human Services states that the term telehealth includes "non-clinical services, such as provider training, administrative meetings, and continuing medical education", and that the term telemedicine means "remote clinical services".

The World Health Organization uses telemedicine to describe all aspects of health care including preventive care. The American Telemedicine Association uses the terms telemedicine and telehealth interchangeably, although it acknowledges that telehealth is sometimes used more broadly for remote health not involving active clinical treatments.

eHealth is another related term, used particularly in the U.K. and Europe, as an umbrella term that includes telehealth, electronic medical records, and other components of health information technology.

It is known in the industry that the 'home patient' is usually given little assistance in managing multiple prescriptions and inventories of medicines. According to some estimates, the average senior person is prescribed up to thirteen different oral medications that must be taken correctly at different times each day. These medications are typically delivered in bulk supply and must be sorted, managed, and taken correctly by the individual, leading to numerous errors and omissions, including failing to take the medications at the prescribed time, taking an incorrect dosage, misusing the medications, fatally combining medications, under-using the medications, or over-using the medications, collectively referred to as "non-compliance".

The costs associated with such non-compliance can be higher than costs associated with several major illnesses. Studies have shown that 10% of admissions to regular hospitals in the United States are due to non-compliance, and 30% of hospital admissions for people over the age of 65 are directly caused by non-compliance. Non-compliance causes 125,000 deaths per year—twice as many as are caused by auto accidents. Twenty-three percent to forty percent of nursing home admissions are due to noncompliance and inability to take medications at home unsupervised. According to estimates, nearly half of all prescriptions are taken incorrectly, contributing to prolonged or additional illness. People who miss doses need 3 times as many doctor visits as others and face an average of $2,000 more in medical costs per year.

The fact that the aging population continues to grow, as well as the average number of medications prescribed per person, these issues will continue to compound along with the associated costs.

Prescription drug regimens are increasingly important in health care treatment. A recent Center for Disease Control report concluded, that over the last 10 years, the percentage of Americans who used at least one prescription drug in the past month increased from 44% to 48%. The use of two or more drugs increased from 25% to 31%. The use of five or more drugs increased from 6% to 11%. The effectiveness of prescription drug treatment is largely dependent on the degree to which the medications are taken as prescribed, an area broadly referred to as medication adherence. Significant medication adherence challenges exist.

The economic cost of medication non-adherence is significant, today it is estimated these costs are more than $100 billion annually, which includes avoidable hospitalizations, nursing home admissions, and premature deaths.

When appropriately prescribed, administered and monitored, medications are a cost-effective way to help maintain health, recover from illness, or control symptoms of chronic disease. A proper medication regimen can cause a critical situation for a large number of people who have severe medical conditions. While remembering to take prescribed medications once or twice a day may seem simple, it is common to forget, or make a mistake. These mistakes leave patients missing a dose, or even cause them to take too much medication.

SUMMARY OF THE INVENTION

The invention described herein is an integrated health management system, apparatus, and method for the gathering and communicating of health data and data related to medication compliance and security.

A processor connected to a communications system and a memory. The memory stores a distributed database that is distributed across at least one of different physical locations, one or more processors located proximate to the processor, and a local network of interconnected processors.

A sensor data collection system, wherein the collected sensor data is responsive to the user and stored in the distributed database.

A pre-packaged tablet delivery apparatus configured to deliver pre-packaged tablets to a user. The delivery apparatus comprising an alignment guide, a processor modulated differential drive, a sensor for sensing a location and an orientation of the pre-packaged tablet, a cutter mechanism, and cutter mechanism control logic. The input alignment guide adjusts the pre-packaged tablets into the delivery apparatus. The processor modulated differential drive is used for the directional control of the pre-packaged tablets. The differential drive comprises a dual motor drive system with independent actuators. The sensor for sensing a location and an orientation of the pre-packaged tablet is used during a delivery wherein the sensed location and orientation of the pre-packaged tablet is used to modulate the differential drive based on at least one of a predetermined configuration within the processor and a dynamic configuration responsive to the sensed location and orientation. The cutter mechanism control logic is configured to monitor the sensed pre-packaged tablet location and orientation, then initiate a cutting sequence responsive to at least one of the predetermined configuration within the processor and the dynamic configuration responsive to determining an optimal sensed location and orientation. The control logic generates and logs a message into the distributed database responsive to the cutting sequence.

BRIEF DESCRIPTION OF THE DRAWINGS

A more complete understanding of the systems, methods, processes, and/or apparatuses disclosed herein may be derived by referring to the detailed description when considered in connection with the following illustrative figures. In the figures, like-reference numbers refer to like-elements or acts throughout the figures.

FIG. 5 depicts a rolled pre-packaged tablet strip with the suspension rod pre- and post-insertion to the roll for hanging in the containment area.

FIGS. 10A-C depict multiple exploded views of the rotary cutter blade, carriage, and blade suspension system.

FIG. 11A depicts the full cutting assembly in its idle position inside the assembly housing.

FIG. 11B depicts the camera, and pincher, positioned on the cutting assembly, with the blade in lateral motion across the cut surface.

FIG. 16A depicts an image from the internal camera showing the perforation in frame.

FIG. 16B depicts the perforation in frame after the image is passed through a histogram filter.

FIG. 16C depicts the perforation in frame after the histogram filter and a best fit line is applied to the image.

FIG. 16D depicts an image from the internal camera when the perforation is not in frame.

Figure 1:
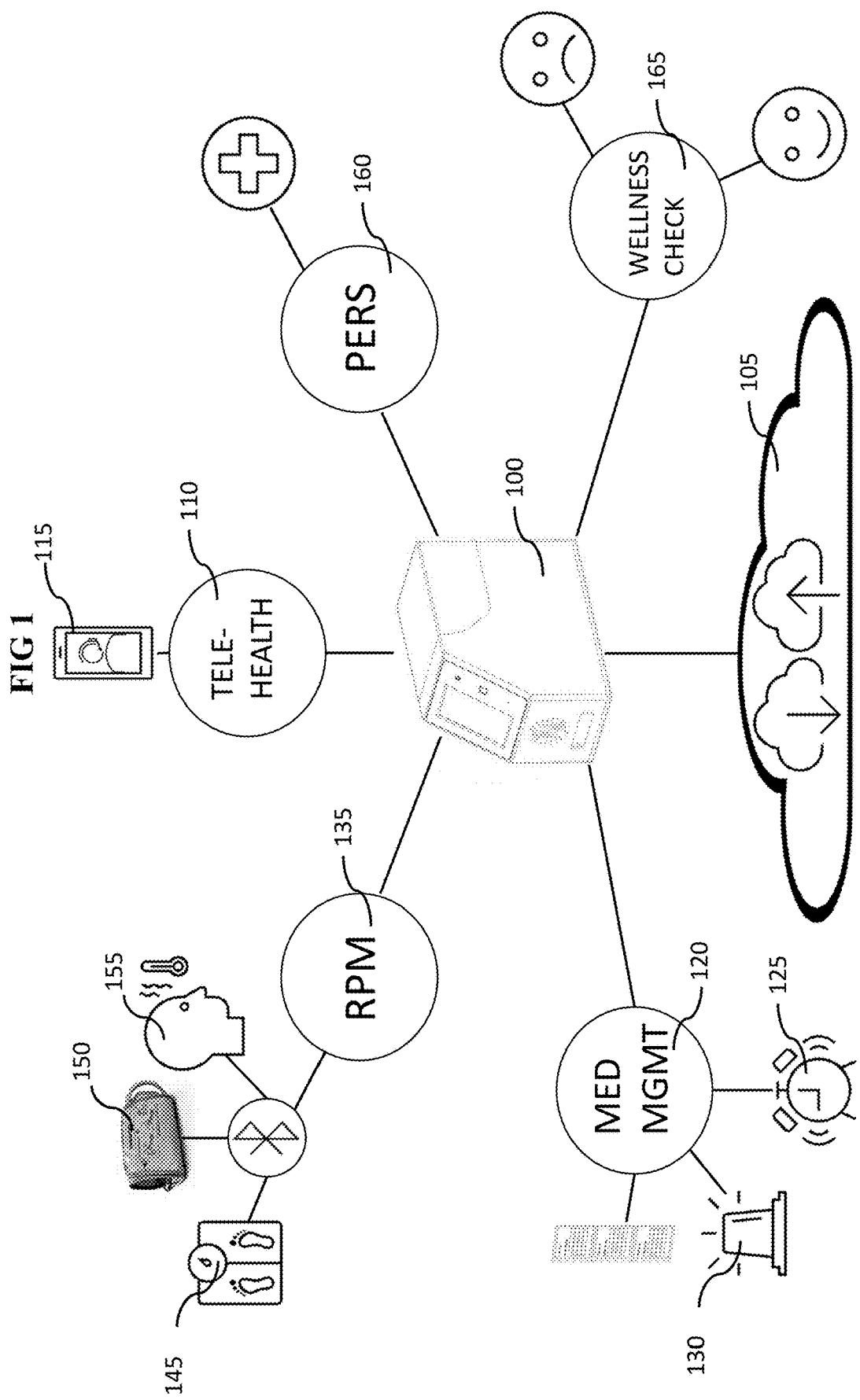
FIG. 1 depicts a summary of the HMS modules, with a centralized focus on the HMS hub device.

Elements and acts in the figures are illustrated for simplicity and have not necessarily been rendered according to any particular sequence or example.

DETAILED DESCRIPTION

So as to reduce the complexity and length of the Detailed Specification, Applicant(s) herein expressly incorporate(s) by reference all of the following materials identified in each paragraph below. The incorporated materials are not necessarily "prior art" and Applicant(s) expressly reserve(s) the right to swear behind any of the incorporated materials.

Aspects and applications presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Detailed Description or Description of the Drawings or claims is not intended to somehow indicate a desire to invoke the special provisions of 35 U.S.C. § 112, ¶6, to define the systems, methods, processes, and/or apparatuses disclosed herein. To the contrary, if the provisions of 35 U.S.C. § 112, ¶6 are sought to be invoked to define the examples, the claims will specifically and expressly state the exact phrases "means for" or "step for, and will also recite the word "function" (i.e., will state "means for performing the function of . . . "), without also reciting in such phrases any structure, material or act in support of the function. Thus, even when the claims recite a "means for performing the function of . . . " or "step for performing the function of . . . ", if the claims also recite any structure, material or acts in support of that means or step, or that perform the recited function, then it is the clear intention of the inventors not to invoke the provisions of 35 U.S.C. § 112, ¶6. Moreover, even if the provisions of 35 U.S.C. § 112, ¶6 are invoked to define the claimed examples, it is intended that the examples not be limited only to the specific structure, material or acts that are described in the preferred examples, but in addition, include any and all structures, materials or acts that perform the claimed function as described in alternative examples or forms, or that are well known present or later-developed, equivalent structures, material or acts for performing the claimed function.

In the following description, and for the purposes of explanation, numerous specific details, process durations, and/or specific formula values are set forth in order to provide a thorough understanding of the various aspects of exemplary examples. However, it will be understood by those skilled in the relevant arts, that the apparatus, systems, and methods herein may be practiced without these specific details, process durations, and/or specific formula values. It is to be understood that other examples may be utilized and structural and functional changes may be made without departing from the scope of the apparatus, systems, and methods herein. In other instances, known structures and devices are shown or discussed more generally in order to avoid obscuring the exemplary examples. In many cases, a description of the operation is sufficient to enable one to implement the various forms, particularly when the operation is to be implemented in software. It should be noted that there are many different and alternative configurations, devices, and technologies to which the disclosed examples may be applied. The full scope of the examples is not limited to the examples that are described below.

In the following examples of the illustrated examples, references are made to the accompanying drawings which form a part hereof, and in which is shown by way of illustration various examples in which the systems, methods, processes, and/or apparatuses disclosed herein may be practiced. It is to be understood that other examples may be utilized, and structural and functional changes may be made without departing from the scope.

Explanation of Terms

As an explanation of terms, within this document there may be multiple interchangeable terms used to describe a like component of the invention and does not necessarily insinuate a new meaning or component. Question of similar terms appearing for seemingly different aspects of the invention should be evaluated in context, and not assumed to be like components.

The term "Health Management System" or "HMS" encompasses the invention in its entirety. An HMS "module" defines a grouping of capabilities for a more specified remote health application.

The term "hub" or "HMS hub" describes the centralized apparatus operating within the system. This is most frequently referred to as the "hub" but may also be referred to as the "apparatus", the "box" or in some cases "device".

The "cloud service" or "backend" collectively refers to the functional operations conducted on a web-based service.

The front end of the "cloud service" is referred to as the "web app" or in some cases "admin web site".

The use of the word "medication(s)" in the context of the delivery apparatus disclosed herein should be assumed a place holder for "package contents", as the delivery apparatus system does not directly handle medications, but rather strip packaging packets with contents. In addition, the use of "medication" is relative or could mean "pre-packaged tablet" "pouch", "packet", or "package" since we are generalizing what is being delivered.

The use of the term "dispense" as used in the patent language is relative to "deliver" or "delivering" a strip package pouch as opposed to the clinical term "dispense" relative to actual handling of medicine.

In terms of commonly mentioned actors within the system, the "patient" or "user" refers to the person which the HMS hub has been issued to. The "caregiver" may be anyone who is configured as the patient's contact for regular health needs. The "remote support" entity is used as a general term for an actor in the system whose involvement supports fundamental functionality within an HMS module.

Discussion

In a discussion of the Health Management System, today health management and healthcare trends in technology driven by and as an extension of COVID-19's far-reaching impact across healthcare has globally affected healthcare technology for ever, including accelerating changes and dramatically demonstrating how nimble the healthcare industry can be. Healthcare data analytics, artificial intelligence, and telemedicine capabilities have massively expanded to support the pandemic response and recovery, a trend that will likely continue to propel healthcare technology.

Data and Analytics Are Increasingly Central to Health System Operations COVID-19 made the need to leverage data and advanced analytics central to many health systems. Expansion of those capabilities to meet the demand for real-time data or close to real-time data has been dramatic.

For example, hospital administrators are looking at their COVID-19 dashboards hourly and using data to update their business intelligence reporting tools. Previously, the most useful artificial intelligence applications and machine learning were likely predicting revenue cycle trends, with attempts for more sophisticated use, such as reading imaging with AI slow to respond or even stalled. Now, COVID-19 has compelled innovation to bring advanced analytics to the forefront of disease response, using predictive models to track the virus and estimate the risk of COVID-19 to patients with severe symptoms, enabling more effective treatment.

Health systems in 2021 are rapidly expanding their support for a digital workforce, including the chief information officer (CIO) role. The CIO is playing a larger role in an organization's strategy, risk management, and cybersecurity. The EHR and EMR Electronic Health and Medical Records have expanded and will likely continue to evolve with digital and voice assistance and natural language processing. With such clinical IT developments, including augmented reliable and wearable technology so that patients can make decisions in real-time with real data, the digital workforce and CIO roles stand to continue to grow.

Telemedicine has evolved as a need to keep people in their homes, this evolution breaks the disciplines of care down into target groups of care givers as opposed to the need for a trained doctor to be the only person able to meet the needs of remote care. These new segments fall under what is generally referred to as Telehealth; these include such remote services as:

Telenursing refers to the use of telecommunications and information technology in order to provide nursing services in health care whenever a large physical distance exists between patient and nurse, or between any number of nurses.

Telerehabilitation (or e-rehabilitation) is the delivery of rehabilitation services over telecommunication networks and the Internet. Most types of services fall into two categories: clinical assessment (the patient's functional abilities in his or her environment), and clinical therapy.

Telepharmacy: The delivery of pharmaceutical care via telecommunications to patients in locations where they may not have direct contact with a pharmacist. It is an instance of the wider phenomenon of telemedicine, as implemented in the field of pharmacy. Telepharmacy services include drug therapy monitoring, patient counseling, prior authorization and refill authorization for prescription drugs, and monitoring of formulary compliance with the aid of teleconferencing or videoconferencing. Remote delivery of tablets by automated packaging and labeling systems can also be thought of as an instance of Telepharmacy. Telepharmacy services can be delivered at retail pharmacy sites or through hospitals, nursing homes, or other medical care facilities.

Telehealth Is Here to Stay, it has become the modern form of health care delivery. Telehealth breaks away from traditional health care delivery by using modern telecommunication systems including wireless communication methods. Traditional health is legislated through policy to ensure the safety of medical practitioners and patients. Consequently, since telehealth is a new form of health care delivery that is now gathering momentum in the health sector, many organizations have started to legislate the use of telehealth into policy.

COVID-19 accelerated an urgent need for telehealth to care for patients outside of the clinic or office setting and offset financial losses due to reduced ambulatory visits. According to a McKinsey study, the number of patients using telehealth increased from 11 to 46 percent in 2020, with growth likely to continue. McKinsey predicts telehealth could account for 20 percent, or $250 billion, of U.S. healthcare spending soon.

Though the transition towards expanded telehealth is in motion (including policy changes around accessibility and reimbursement), healthcare technology will still need to adapt to accommodate the continuing shift. Health systems need greater integration with existing technology platforms and strategies to address cybersecurity and privacy concerns. In this way, telehealth is another area that will increase demands on the digital workforce and healthcare CIOs.

The current state of the health and wellness market demands a system apparatus with which several issues with existing "home health" systems are adequately addressed. As previously stated, these issues commonly revolve around the home patient being generally disconnected from help in a multitude of health-related situations, and a lack of information collection necessary for adequate health care.

An illustrative overview of the disclosed invention is depicted in FIG. 1, where the Health Management System (HMS) comprises the HMS "Hub" 100 and the various modules of the HMS, essentially illustrating the capabilities of the modular system with a centralized focus on the Hub. The system provides an adaptive and remote solution for several remote health needs, the first being medication management 120, featuring a delivery apparatus, medication reminders 125, and adherence alerts 130. The second module provides remote patient monitoring 135, featuring multiple health vital measuring devices, examples including remotely connected scales 145, blood pressure devices 150, or temperature reading devices 155 to name a few. The third module being General Telehealth communications 110, primarily addresses remote health communications between the user and a health professional 115. The fourth module being the Personal Emergency Response System (PERS) 160 featuring 24-hour remote support for health emergencies. The fifth module being wellness checks 165 featuring routine health related surveys to obtain a regular source of patient feedback of their self-evaluated condition.

These hub modules, as depicted share at least one connection with the centralized hub 100 and therefore, the cloud interface 105. While each module features unique functions and capabilities, the modules collectively share a reporting function hosted by the cloud interface, or "backend". The hub modules are provisioned to work in any combination, making it easy for any organization to adopt for targeted goals. Along with the modular hub design, the integrated reporting aspect of the invention is also designed to be customized per use case. The reporting can be edited to provide select data so that feedback is streamlined and succinct.

Figure 2:
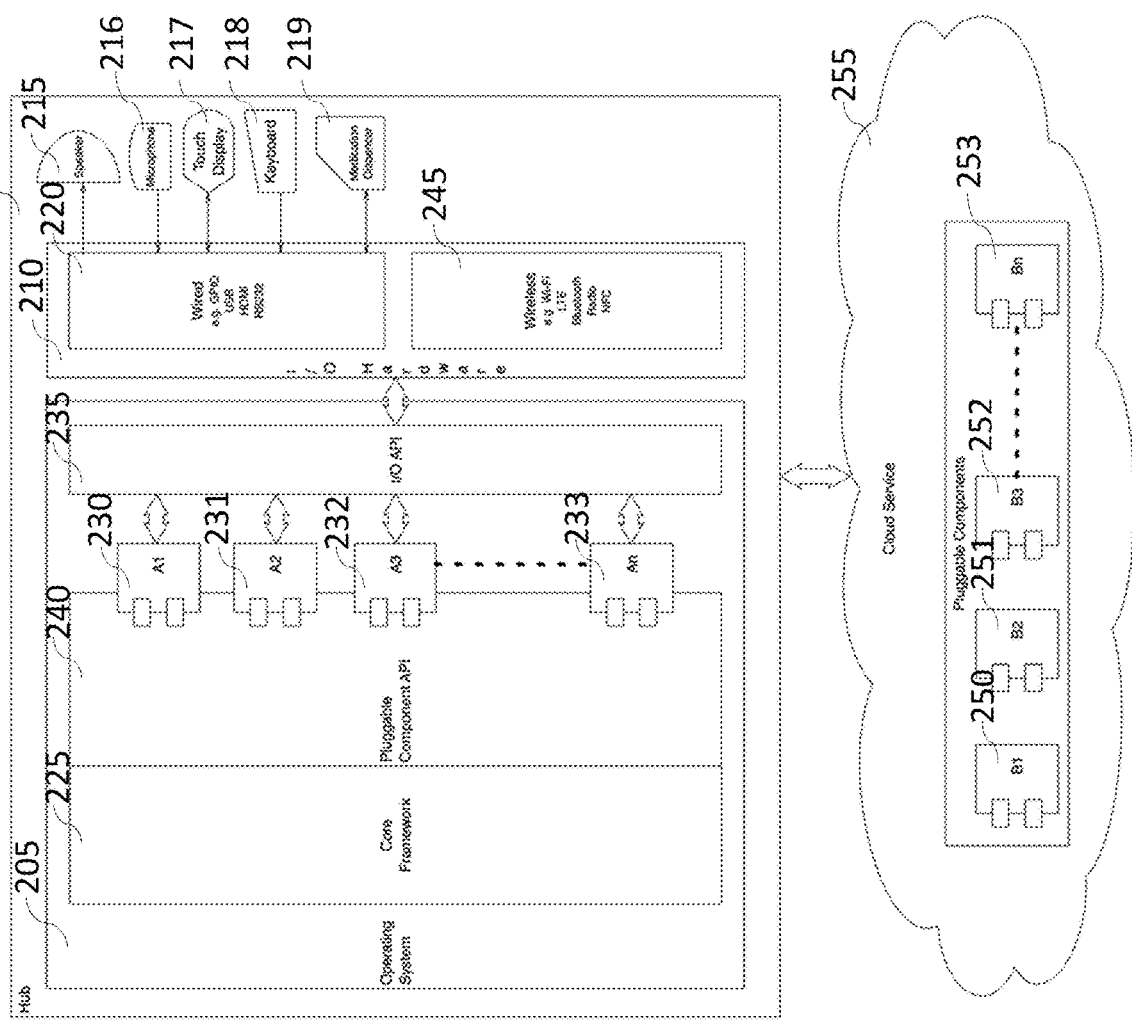
FIG. 2 depicts the high-level architecture of the HMS logic framework.

FIG. 2 depicts the network topology of the HMS, wherein the Hub 200, comprising a computer and operating system 205, and I/O hardware 210. Various hardware devices, such as a speaker 215, a microphone 216, a touch display 217, a keyboard 218, and delivery hardware 219 are integrated into the Hub using wired I/O hardware interfaces 220.

The Hub core framework 225 manages the boot process, local data storage, cloud web service communication, access security, and new business logic deployment and also acts as a host for an extensible number of business logic components depicted as A1 230, A2 231, A3 232 thru An 233 by providing a common pluggable component API 240. Linking to these components is dynamic and can be achieved using DLL's, OSGi, shared objects, or other technologies.

Each component (A1, A2, A3 thru An) represents an atomic function. That is, a component can execute on its own without reliance upon another component. For example, A1 230 could represent the medication management module and A2 231 could represent the PERS module.

Each component has access to an I/O API 235 which is an abstraction of wired 220 and wireless 245 device interfaces.

Each component has a corresponding component (B1 250, B2 251, B3 252 through Bn 253) in the cloud 255. The cloud components are responsible for hub component configuration properties, reporting, interfacing to 3rd party services, and other functions.

Figure 24:
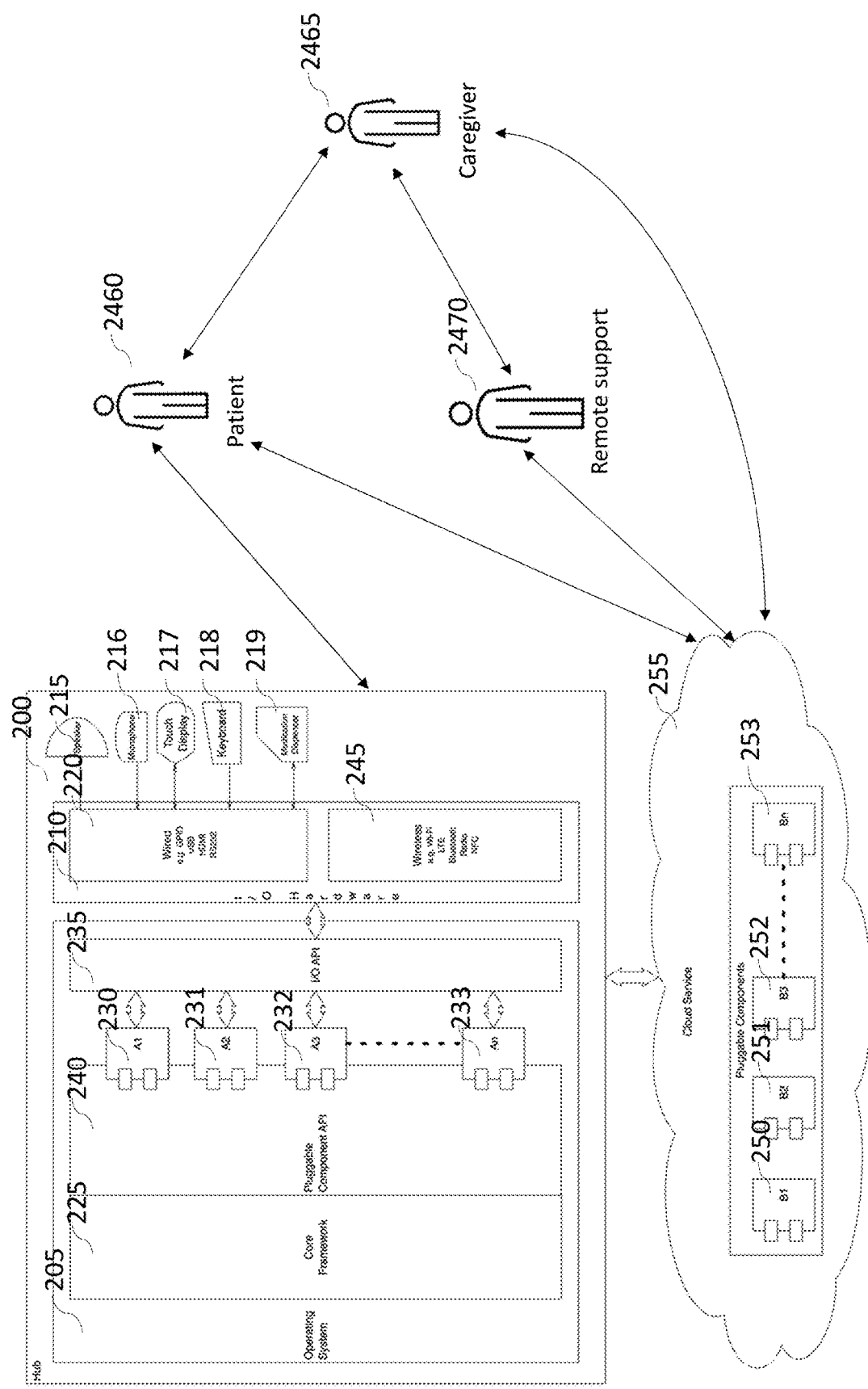
FIG. 24 depicts process pathways for the HMS module' connectivity relative to the hub, cloud service, and some common actors.
Figure 25:
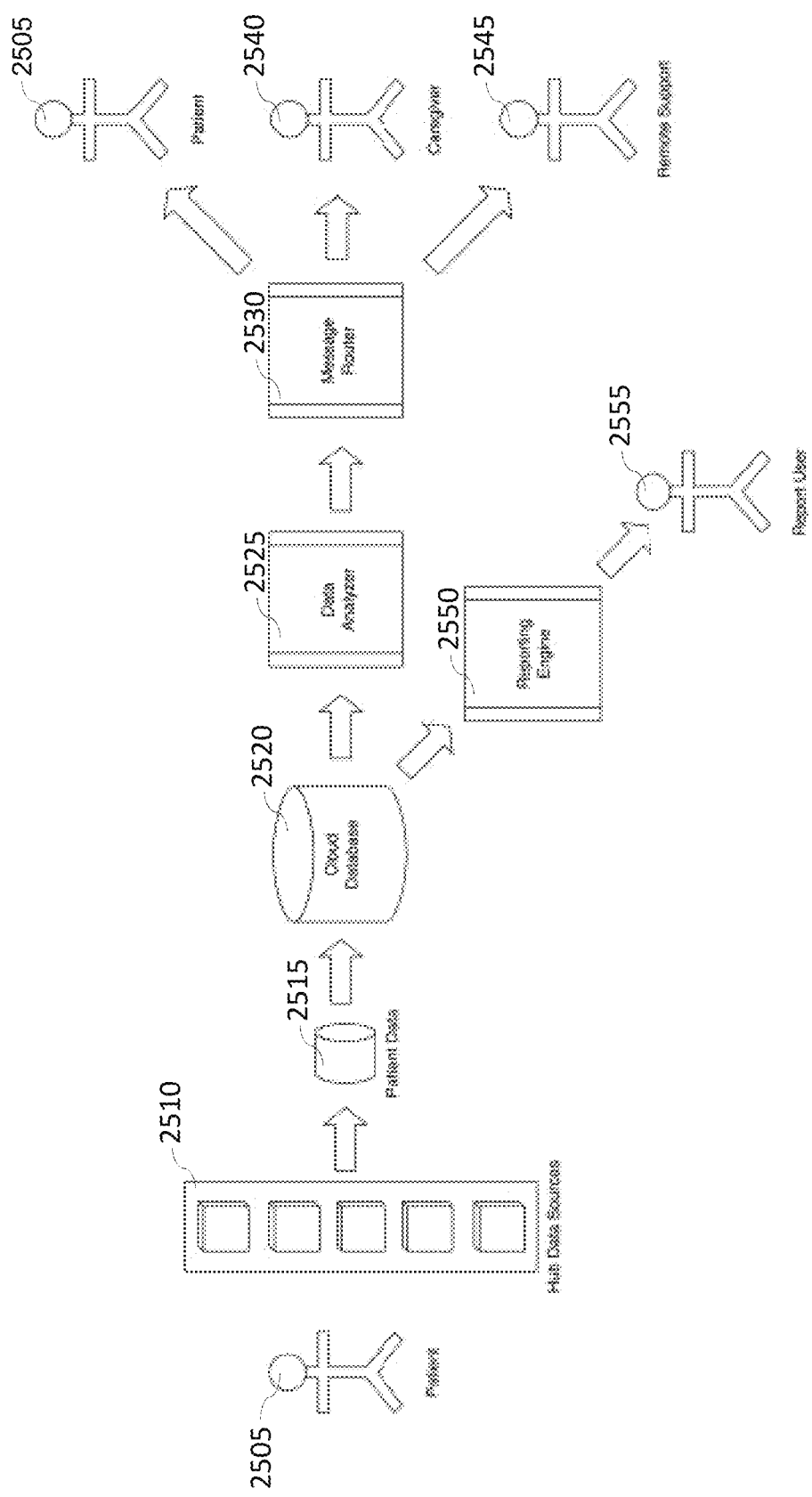
FIG. 25 depicts the patient data pipeline.

In one example, the patient data pipeline is shown in FIG. 25. Data sources 2510 can be modules that include hardware devices. Examples of hardware devices are heart rate and blood pressure monitors, PERS, or delivery apparatus. Data sources can also be pure software modules, such as the wellness app. Hardware devices are connected to the hub, either wired, see FIG. 24 220 or wirelessly, see FIG. 24 245.

Data sources generate patient data 2515 upon interaction with the patient 2505, utilizing the appropriate hub pluggable component, see FIG. 24 230-233. The patient data is sent from the hub to the cloud service, using a secure web service call. The patient data is then stored in a secure database 2520.

A reporting engine 2550 allows an authorized user 2555 to pull detailed and aggregated reports.

Upon new patient data becoming available, the data analyzer 2525 examines the new data, possibly in combination with historical data, and evaluates if there is an out of tolerance situation. In this case, an exception message is created and pushed to the appropriate service, patient 2505, caregiver 2540, and or remote support 2545, with the message router 2530, for remedial action to be taken.

Figure 3:
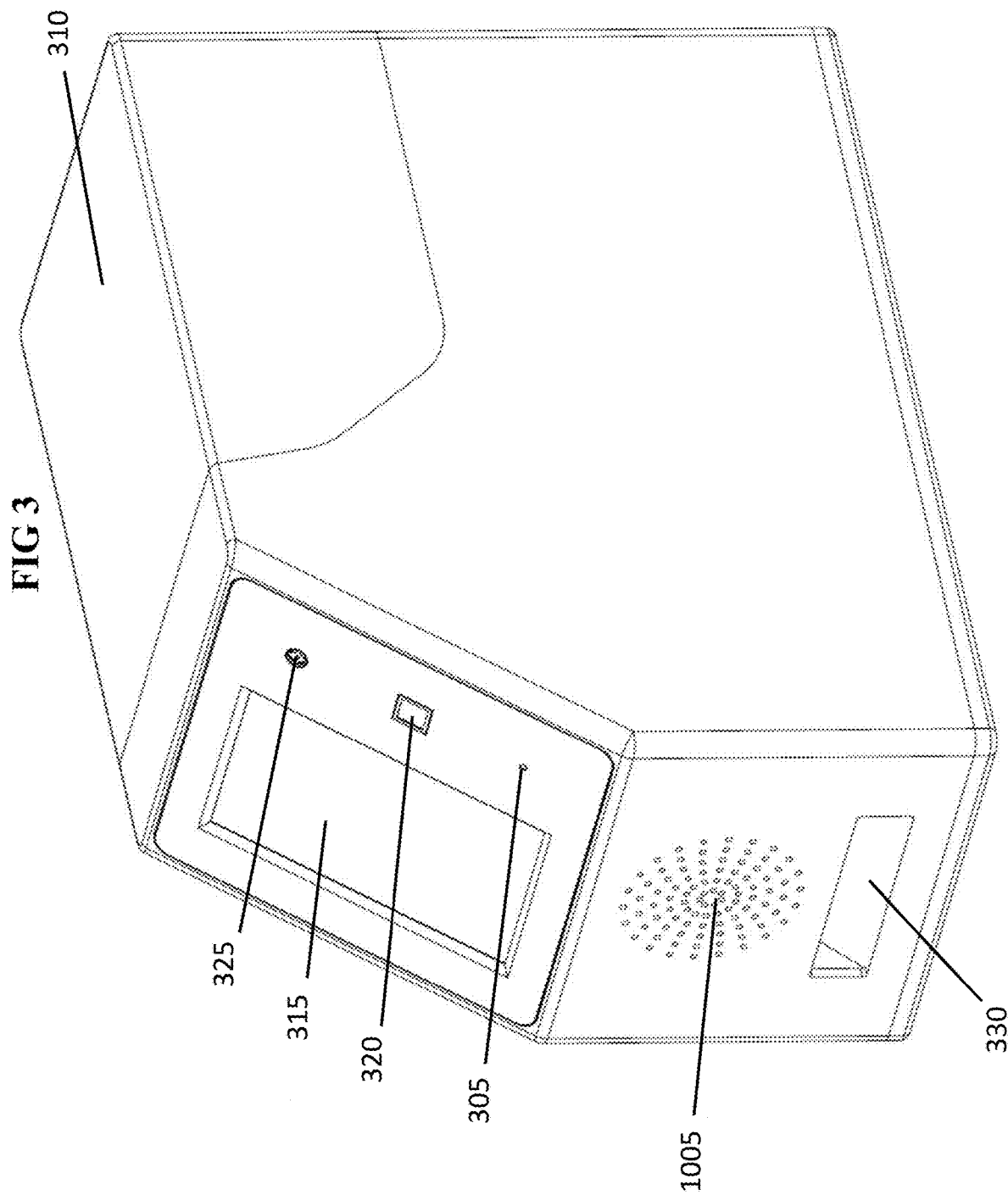
FIG. 3 depicts one example of the hub device from an external perspective, complete with top access lid.

FIG. 3 depicts one example of the physical HMS hub. The hub will be the patient/user centralized interface for the HMS modules. The physical hub is equipped with a touch screen 315 for interacting with many of the modules as further described in sections of this disclosure. The speaker 1005 and microphone 305 allow for two-way audio communication, either in live communications, or automated processes, such as reminders or notifications to the patient. 310 shows the access lid to loading pre-packaged tablet strips into the hub for delivery, and 330 shows where those pre-packaged tablets are delivered. The exterior camera 325 enables visual features for communications and in some examples, user authentication processes in the form of facial recognition. The external camera in some allowable conditions, can be deployed with deliver events to as a means to capture photo or video confirmation that the delivery of a pre-packaged tablet was successfully taken by the user. Biometric user authentication may also be accomplished through the use of the integrated fingerprint reader 320.

This rapid rise of Telehealth has health care providers now introducing and leaning upon new methods of administering the same level of care in an environment that no longer relies on a high level of close, interpersonal interaction. The current state of the health and wellness market demands a Health Management system that supports many and hopefully all of the needs recognized during the pandemic with a focus the home patient being generally disconnected from help in a multitude of health-related situations. The invention disclosed provides an adaptive and remote solution for medication management, remote patient monitoring, wellness checks, emergency response, and general telehealth.

In a further discussion the Medication Management Module as introduced previously, there is a need for an airtight medication management system for the home patient. This requires a tightly managed package delivery system, specifying the date and time the meds are to be taken, containing all the pills for each individual time, all while being monitored. Such a prepackaged and managed group of medications would relieve the patient from having to remember which pill is to be taken at which time. Prepackaging a series of pills and delivering them in an individual package is done at the present time in a manual manner. As an example, in an institutional model like a hospital, such prepackaging is done at the hospital pharmacy, if the patient is required to take several different pills at different intervals, the hospital pharmacist will take the individual pills from the storage containers and place them in individual packages with the patient's name and time for administration written on the package. Each package may contain one or more pills depending on the time of the day and the various prescriptions for that patient. For example, if a patient has four prescriptions, two of which require a pill four times a day, one of which requires a pill twice a day, and the fourth of which requires a pill every other day, the individual packages prepared may contain anywhere from one to four pills, depending on the time of day or day itself.

In terms of labor and potential points of failure, controlled delivery systems and methods would greatly improve the current state of the art.

Today, companies like CVS and Amazon's PillPAK, presort medications to a patient in medication strip packaging, these come marked with the medications it contains, and the date and time the medications are to be taken.

Figure 4:
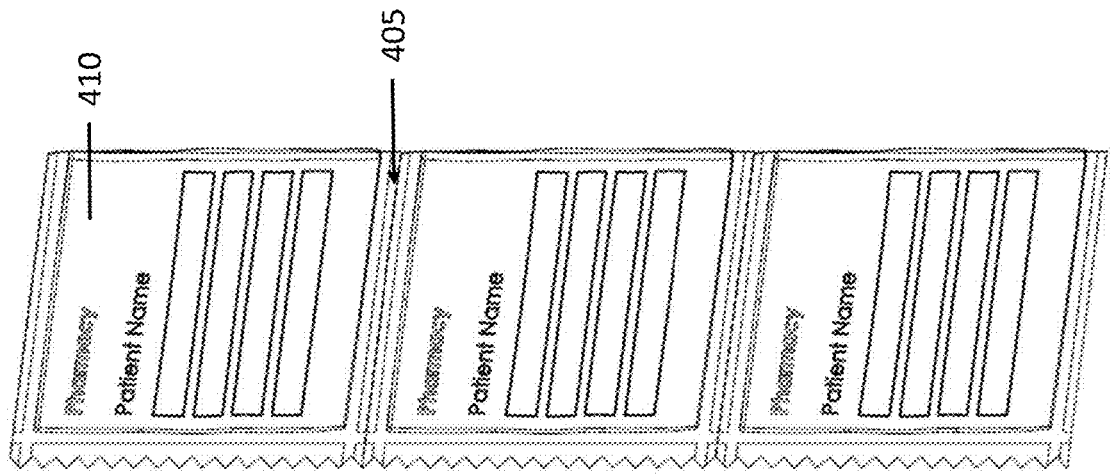
FIG. 4 depicts a section of a pre-packaged tablet strip representative to those that are fed through the HMS device.

The packaging of these universally available pre-packaged tablet strips 410 depicted in FIG. 4, vary between companies, and have been observed to vary even within a single company. Observed variations include the level of transparency of the plastic wrapper material, accuracy and thoroughness of the perforation between packs on the prepackaged tablet strip 405, and the length and height of each package. While these variances are anticipated between different companies, variances within a company have also been observed due to machine manufacturing tolerances, as well as the contents of the package manipulating the overall shape and size.

The variability observed in these pre-packaged tablets has made development of an agnostic delivery system unpopular, as is illustrated by the review of prior art. Provided within this Medication Management system are delivery apparatus which address the variances and provide the functional capabilities required to deliver non-specific pre-packaged tablet strips.

The medication management module comprises the physical delivery apparatus of the hub and the various reminding, alerting, and reporting processes that accompany a deliver event.

Core aspects of a medication management process include the following; a deliver event is initiated by a patient's medication schedule, the event customized by the delivery settings. The medication schedule initiates at least one reminding sequence, wherein a patient's responsiveness to the reminding sequence initiates delivery, and wherein a lack of responsiveness initiates an alerting process. Portions of data may be collected throughout the deliver event to aid in general medication adherence reporting or analytics. This data includes but is not limited to, delivery times as comparable to schedule, the amount of reminding required for patient action, and number of alerts sent before caregiver action.

In an overview discussion of Medication Management, after the initial HMS hub configuration (depicted in FIGS. 17 and 19, and discussed in later portions herein), the hub will prompt the pre-packaged tablet loading procedure. The device is loaded with a non-specific pre-packaged tablet strip by either a caregiver or by the user/patient. Upon loading, the device will compare the pre-packaged tablet strip with the configured medication schedule pulled from the cloud interface configuration. In some examples, the identifier on the manufacturer box containing the pre-packaged tablet strip is scanned prior to loading. This can provide details such as contents, schedule dates and schedule times to compare against. Another method is to run the entire pre-packaged tablet strip through the delivery apparatus, cataloging the information contained on the pre-packaged tablets and comparing against the configured schedule. A third method relies on manufacturer accuracy and compares schedules by confirming the first pre-packaged tablet contents, delivery time, and date are correct, and assumes validity of the remaining strip.

When the initial loading and setup are complete the hub displays an idle screen wherein the "next medication" time is displayed in some examples. If enabled, the backend may define a window of time within the schedule wherein a medication can be delivered early, within a certain number of minutes before the prescribed scheduled medication time. If this functionality is enabled, the idle screen will provide a "Deliver" button which can be utilized at any time within that window to retrieve medication early. If early delivery is not enabled, at the prescribed medication time, the touchscreen on the front of the device displays on-screen instructions to deliver the scheduled medication and begins to remind the user by way of a visual reminder displayed on the device's touchscreen. If the user does not interact with the device by following the on-screen instructions, after an amount of time defined by settings on the backend, the device, in addition to the visual reminder, begins to play an audible tone designed to draw attention to the device. If there continues to be no interaction with the device, the system will generate a phone call to the patient phone, reminding them of the medication.

At any point in time, if the user interacts with the device to acknowledge reminders, further reminders are disabled and the device proceeds to an optional user authentication step and upon success, the delivery sequence. If all reminder attempts are unaddressed, the system will send an alert to a caregiver and the medication is now considered late or missed. If a medication is late or missed, the system may instruct the user to contact their caregiver for instruction, dispose of the meds, or in some examples, may allow the user to deliver the medication for use if this meets the criteria of their medication schedule, and the type of medication.

In other examples, the device may contain an area where the 'missed' medication will be delivered and stored if it is determined the patient should not be allowed to take the medication after is it a certain number of minutes past the medication time.

Reminders are an important aspect of the medication management module. A system of reminder escalations is implemented to encourage a patient to swiftly respond to the apparatus when a scheduled medication time has approached. In this example there is a multitude of reminder styles which are consecutively deployed in an order which is configurable in web app delivery settings. One reminder style is a visual indication on the device, wherein the device screen may flash, or display some combination of animations and text which grab the attention of passersby to indicate that action is required. A second reminder style is an audible indication. Audible reminders may alert the patient that action is required through an audio file which may include any number of urgent tones, music, or even voice recording of a loved one reminding them to take their medication on time. A third reminder style would be an SMS and/or phone call sent to the patient's phone as a reminder of the scheduled medication.

In a discussion of External Medication Reminders, in some examples, the patient's medication schedule may include medications external to the strip packaging housed within the device. This might include refrigerated medications, liquid medications, or as-needed medications. In this example, a reminder will be provided to the patient, like other reminders, alerting the patient to take medications and provide an action to confirm that a medication has been taken.

Auxiliary medications, in some examples are accompanied by accessory medication management hardware and software. Examples of this include connectivity with Bluetooth or network connected devices such as smart medication containers, or smart refrigerators, which can communicate with the hub.

Medication management alerts and more specifically Care Giver Alerts are generated for multiple reasons. In terms of medication adherence, following at least one form of reminder procedure, an alert may be sent if the device has not reported a "sufficient action" from a patient regarding scheduled medications. In some examples, the "sufficient action" may be defined by configurable device settings such as "alert if visual and audible reminders have been left unaddressed" or "alert if 30 minutes have passed the scheduled medication time without action".

In some examples, actionable requests can be pushed to the caregiver depending on the apparatus settings. These requests include delivery approval for meds that fall outside of the expected delivery window. For example, if a patient is late to the deliver event, there exists a threshold that, when passed, will label the medication as "missed". If the medication has been missed, and a patient tries to deliver the medication, a caregiver can choose to approve or disapprove the delivery, using their knowledge of the type of medication and the patient's care plan.

The device communicates with the cloud service to send alerts via at least one of a SMS text, email, or phone call using a scripted voice message directly to a caregiver or other patient advocate configured to the device for a given patient.

Alerts may also be generated for general hub related reasons. Component status alerts may be sent to indicate situations such as loss of power, network connectivity, a reload of medication, box tampering, low battery, mechanical failure, or any other alerts relating to the overall operation of the apparatus. This allows a remote support entity to monitor issues that may arise with the device and remedy the situation to ensure continued health management services.

Figure 20:
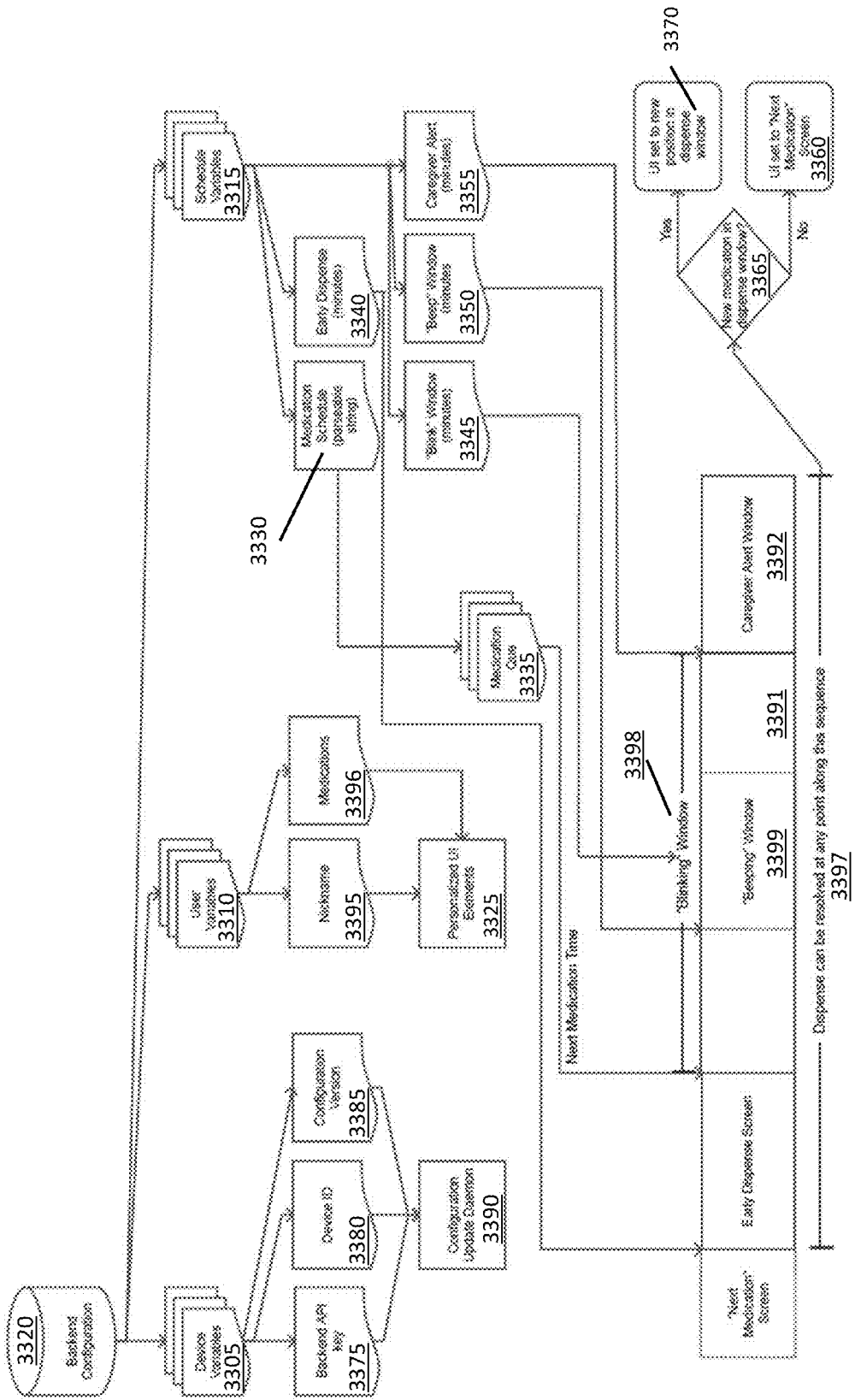
FIG. 20 depicts a flowchart for the system variables, with emphasis on delivery event functional architecture.

Delivery Event Architecture, FIG. 20 depicts one example of a delivery event architecture wherein hub settings which are transcribed from the cloud interface/backend are called on as the framework building blocks of a customized delivery procedure. Three main categories of variables are depicted: device variables 3305, user variables 3310, and schedule variables 3315, which are all configured on the administrative backend (cloud interface) 3320 and have some control of the behavior of the hub. Device variables 3305 are used to identify the hub during communications with the backend. These variables include the API key 3375 to enable communications between the hub and the backend, the configuration version 3385 to identify the last configuration of the hub, and the device ID 3380 for establishing a unique pathway between the device and patient account. The API key 3375, device ID 3380, and configuration version 3385 variables are collectively referenced when deploying the configuration update daemon 3390 which checks the backend for any changes to account settings of any kind and implements them onto the device.

User variables 3310 are used to personalize the hub to the user. A few of these variables include the patient name/nickname 3395, and the patient medications 3396. These user variables, and many which are not depicted in the figure for simplicity, drive the personalized UI elements 3325. Some user variables of mention not depicted in FIG. 20 include impairment variables, authentication variables, and contact variables which are further described in sections following.

Schedule variables 3315 are used to determine how and when the hub performs actions related to delivering medication. Collectively, these schedule variables define the entire delivery window 3397 which illustrates the total available window wherein a medication can be delivered. In some examples the medication schedule 3330 is passed to the device as a single string which defines the schedule on a weekly basis, with a schedule resolution down to hourly increments. This string is parsed as an array of timestamps wherein the device then iterates through the timestamps and generates medication ques 3335. The early delivery window 3340 is a time during which a patient can deliver the next medication prior to the arrival of the actual scheduled time. Once the scheduled time has been reached, the device processes a series of escalations to remind the patient. As an example, FIG. 20 illustrates escalating reminders that begin with visual reminders, which escalate to the addition of audible reminders and then escalate to a reminder sent directly to the patient phone (SMS/phone call). The "Blink" window variable 3345 will indicate when a patient has entered the reminder sequence and is input as a variable duration of minutes as depicted by "Blinking" Window 3398 in the reminder timeline. Within the "Blinking" Window 3398 there is a "Beeping" Window 3399, which is defined by the duration set in the "Beep" window variable 3350, where the device uses its audio system to remind the patient, which is immediately, or close in time, followed with an automated reminder call to the patient, and defines the start of the final reminder window 3391. After the "Blinking" window 3398 expires, indicating all escalation reminders have deployed, a Caregiver Alert window 3392 follows. This window is defined by the minutes input as the caregiver alert variable 3355. The caregiver alert variable 3355 is the amount of time after the full escalation of reminders have concluded where an alert is sent to the patient caregiver, to prompt their attention of a missed medication. In the Caregiver Alert window 3392, the medication is considered "late", the caregiver is alerted, and the patient may be encouraged to check with their caregiver before delivering and administering the medication.

At any point within the 'blinking' window 3398 the patient can resolve the delivery operation and the device will move to the logic block 3365 wherein the next medication que is evaluated, and if the next que falls within the next delivery window, the device returns the appropriate user interface within the reminder sequence 3370 or if not within the delivery window, returns to the idle "next medication" screen 3360.

Adherence Reports are responsive to the various combination of medication management data events, adherence reporting data is compiled on the backend, and viewable as a report on the web application. As each delivery event occurs on the device, the data is stored locally for a temporary amount of time until packets of data are transmitted to the database on the backend.

This data may then be selectively utilized for fully customizable charting or reporting for evaluation of the patient's medication adherence.

In some examples, the escalating reminders and alert system dictate the "labels" of a delivery event and may aid to indicate adherence ability. As one example, a delivery event label may include one of "early", "on time", "late", or "missed" depending on when, within the escalating reminder and alert system, the medication was delivered. Adherence reports consider how frequently a patient requires caregiver alerting or intervention, or how far the reminder system must progress before a patient typically responds.

In other some examples data compiled is additionally used in evaluation of device status and caregiver interactions as well, which is further mentioned in other parts of this disclosure.

Delivery Apparatus Overview. Disclosed herein are physical systems to support the delivery of universally available pre-packaged tablet strips. The discussion following explains the multiple sub-apparatus within the apparatus to support the variability in pre-packaged tablet strips previously mentioned.

The operation of the mechanical and electrical assemblies of the delivery apparatus utilizes at least one of a predetermined configuration within the processor and a dynamic configuration responsive to the sensed location and orientation of the pre-packaged tablet within the delivery channel.

Depicted in FIG. 5 is a rolled strip 705 supported axially by an input orientation guide comprising a set of concentric rods 710 which slot into an input alignment guide 635 on each wall and relieve the driving motors from additional friction and weight that can occur between the holding area and the rolled strip when large quantities of packs or larger weight packs are loaded into the apparatus. These support rods are simply pushed through the roll as most manufacturers send these strips pre-coiled in a box. While this support method provides an additional layer of support to the driving motors, other examples for loading are also supported with the system components disclosed herein. Due to the orientation system and delivery capabilities, no extraneous support is required for the pre-packaged tablet strips to be loaded. A pre-packaged tablet strip can be placed into the containment area as a loosely placed coil, or in any general orientation without the supports illustrated. In some examples, medication loading is handled by a caregiver, and access to the medication through the access lid is restricted by a locking assembly.

Figure 6:
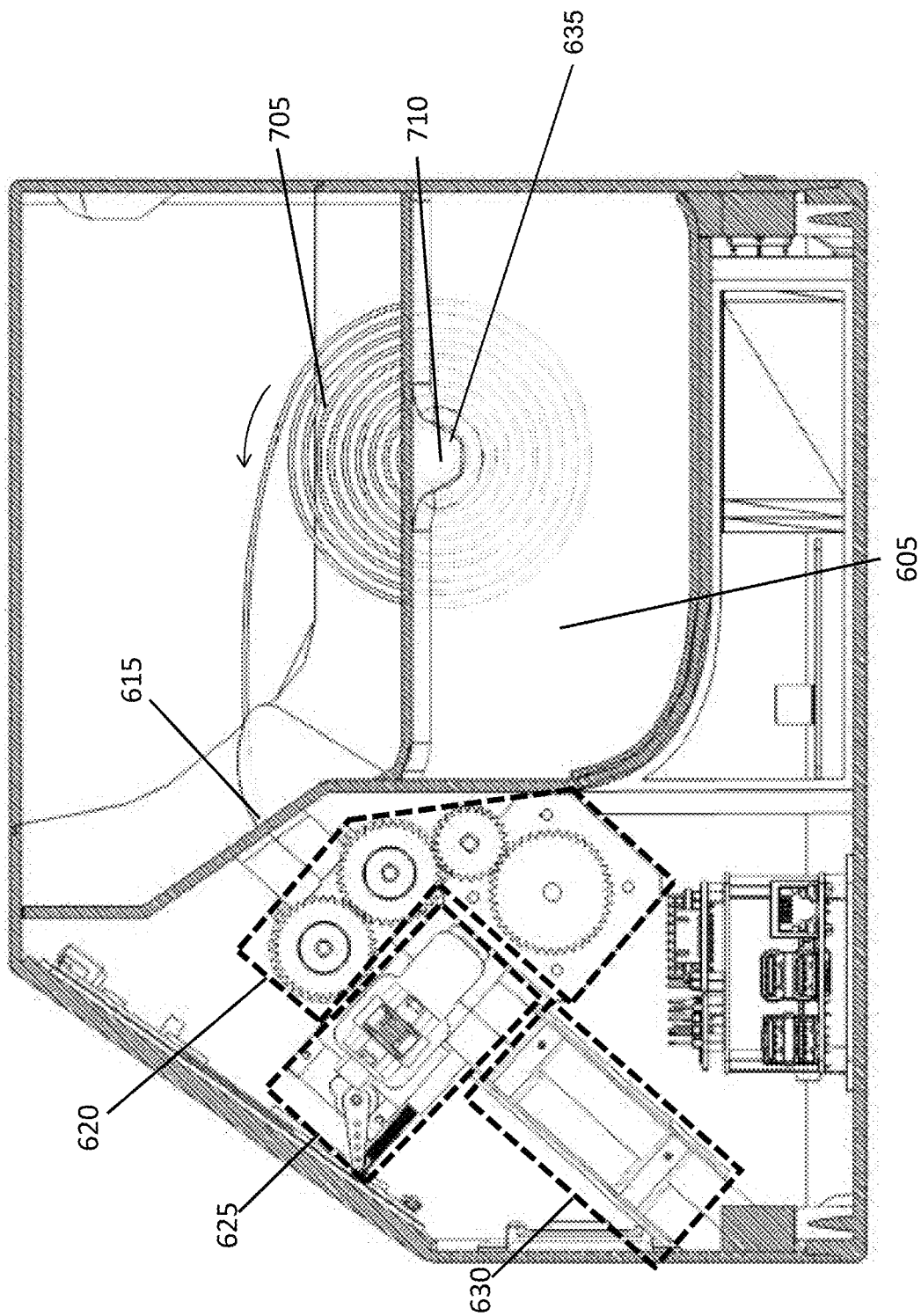
FIG. 6 depicts a side perspective view of the loaded hub with an overview of the delivery apparatus.

FIG. 6 depicts a side perspective of the collective delivery apparatus. The pre-packaged tablets, such as illustrated with respect to pre-packaged tablet strip 705 is shown loaded into the containment area 605 on the support rod 710, with the leading edge of the strip being pulled into the start of the pre-packaged tablet delivery apparatus or the delivery apparatus 615. Moving along the channel is the processor modulated differential drive 620, followed by the cutting channel assemblies 625 and sensor 630.

Figure 7:
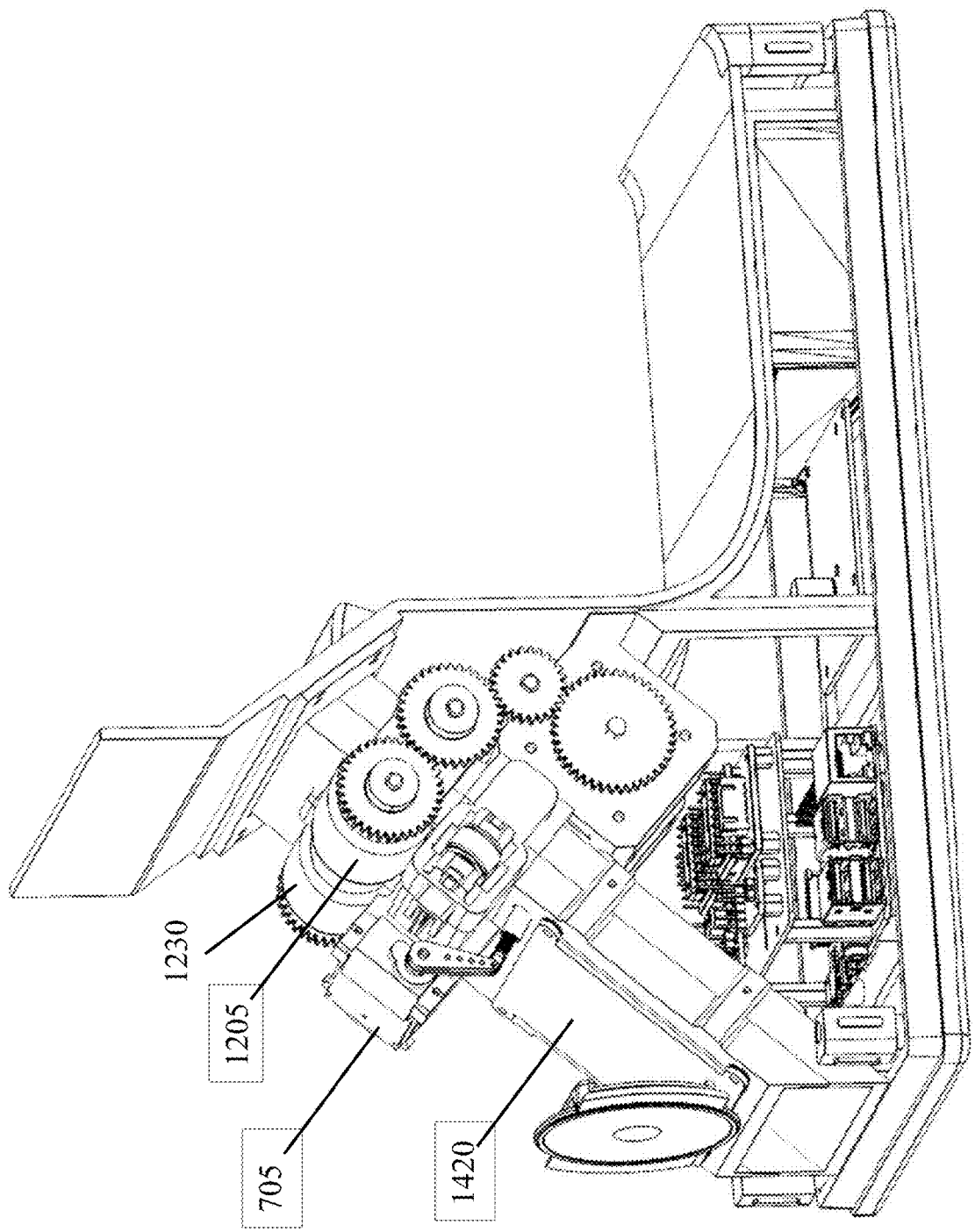
FIG. 7 depicts the device with side walls and lid removed to show the arrangement of delivery apparatus.

FIG. 7 depicts an isometric view of the collective delivery apparatus. This image shows a more clear depiction of the placement of independent actuators 1205 and 1230, internal camera 705, and sensor boards 1420.

A Processor Modulated Differential Drive is disclosed. In a previous example, the drive system consisted of a pair of actuators which were each set on a rod shaft, controlled with a single stepper motor. The actuators ran the width of the inside channel and applied even pressure along the leading edge of the packaging which caused the actuators to pull the packaging into the channel at whichever angle the packaging was inserted. The angle of approach was maintained as pill packs were continually pulled in which left a lot of room for user error.

In some examples, the actuators of the differential drive are two pairs of rollers, positioned to drive the left and right sides of the pre-packaged tablet pack.

Figure 8:
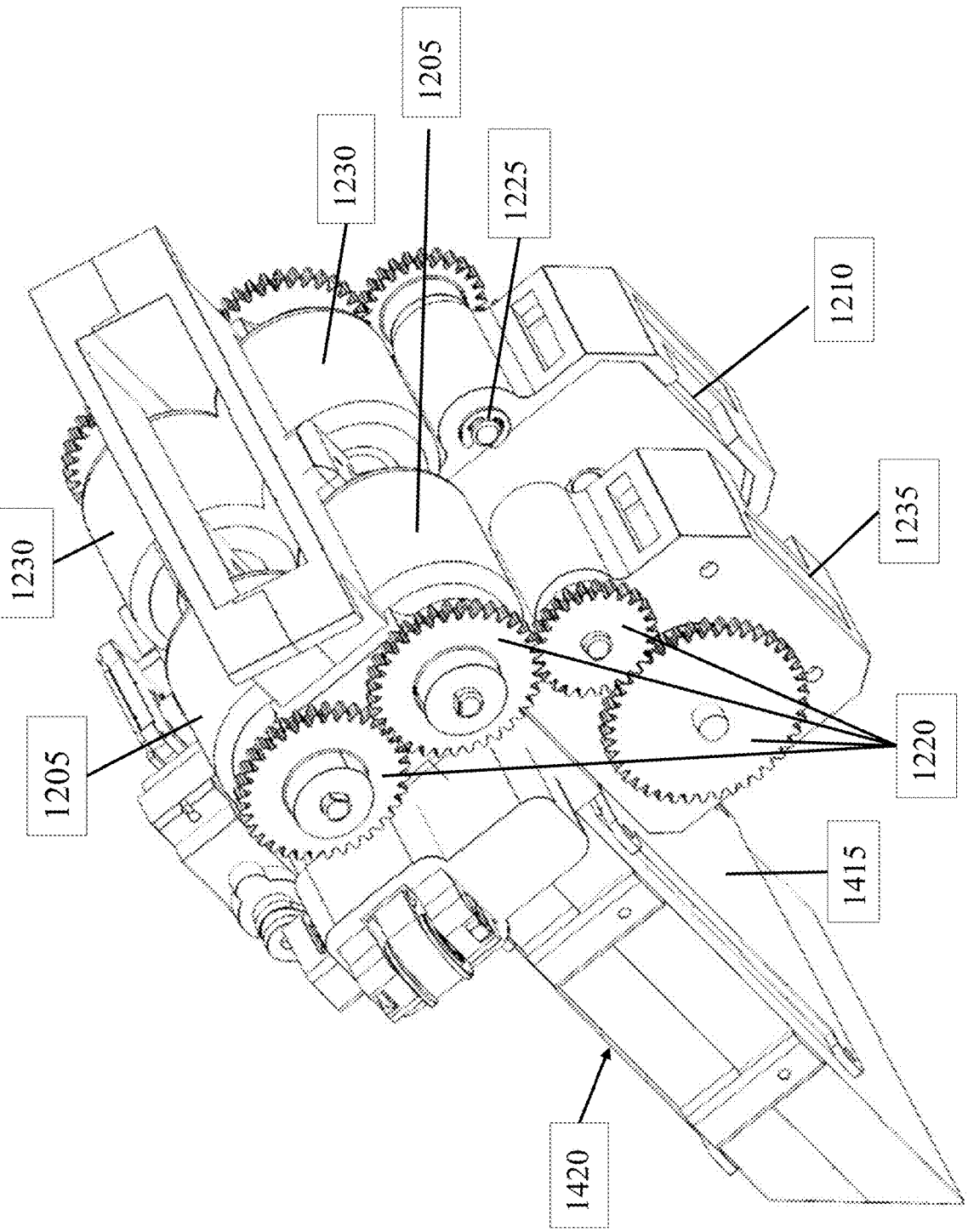
FIG. 8 depicts an isometric view of the dual motor drive system affixed to the channel.
Figure 9:
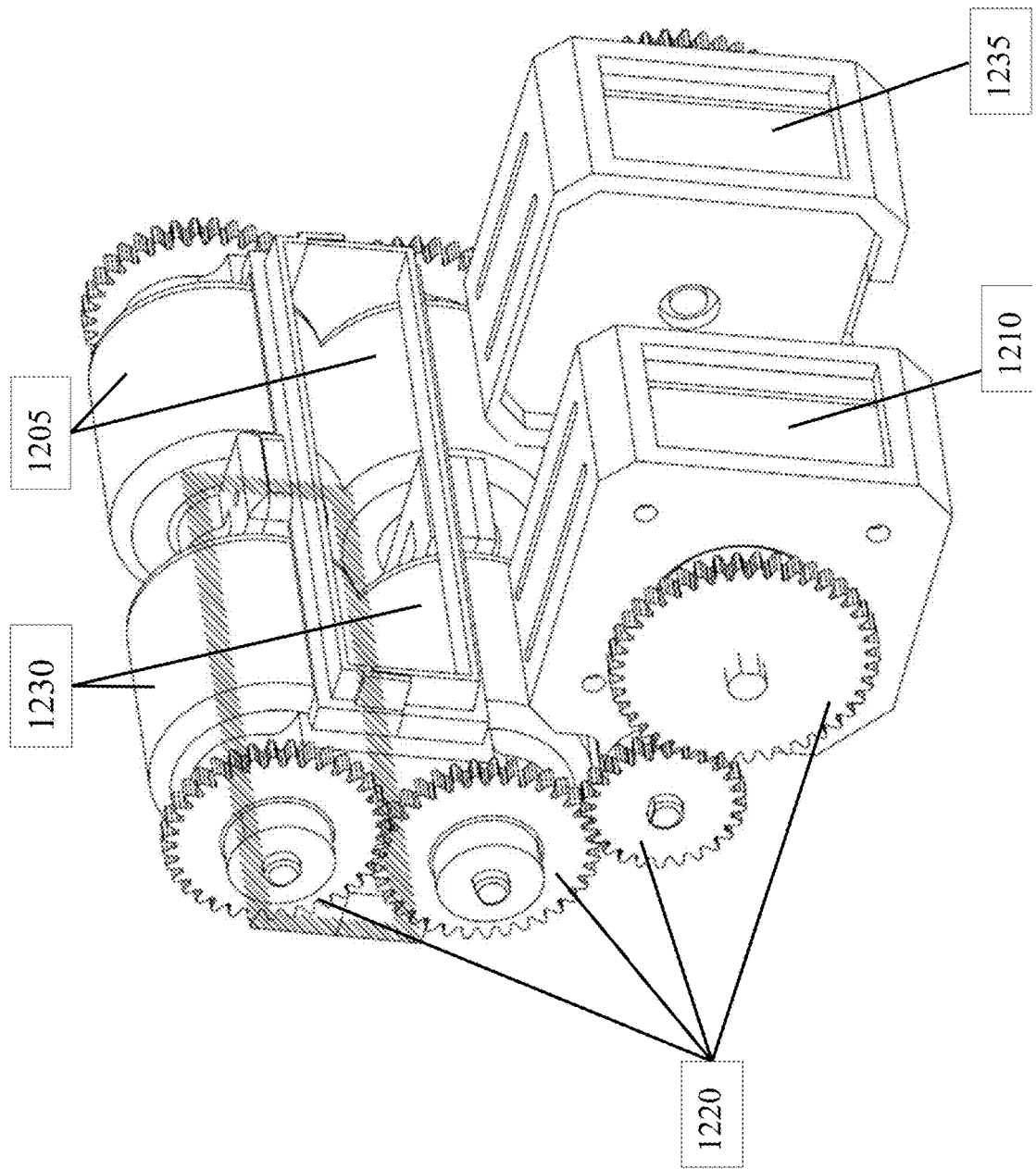
FIG. 9 depicts the dual-motor drive assembly isolated from the delivery channel to show the split-design and gearing of the system.

As most clearly depicted in FIGS. 8, and 9, a processor modulated differential system is deployed, consisting of two pairs of actuators 1205 1230 assisted by oil-infused bearings, each actuator set individually controlled by a stepper motor 1210 1235 on either side of the packaging, maintains the orientation of the packaging as it is loaded and pulled into the channel. Depicted in FIG. 8, as the system receives location feedback from a sensor array, comprising two sensor plates 1415 1420, each side of the packs is moved by the corresponding stepper motor 1210 1235 backward or forwards to maintain the correct loading angle. Correct orientation greatly reduces the risk of jamming errors.

The advantages of using stepper motors to drive this assembly include the ability to move the packaging either in very small increments or continually both backward and forward. Two stepper motors versus a single motor increase the amount of torque (pulling power) on the packs. The motors were selected with high torque, low heat output, and overall quality in mind.

The gear assembly 1220 ensures a 1:1 ratio while the hard material maintains rigidity and consistency. The characteristics of size, tooth count, pitch, to name a few, were selected to match the torque output of the motor to maintain/increase the mechanical advantage of the gearbox as well as the rotational speed of the actuators.

The material of the four actuators 1205 1230 can be selected based on the amount of friction (grab) necessary to pull the strip packaging through the device. The inner and outer diameters of the foam were chosen to provide enough overlap between the top and bottom actuator to maintain a grip on the bag. The open-celled foam provides a large amount of deflection, due to its texture, needed to overcome larger pill sizes and shapes. Oil-infused bearings were placed over the rod shafts to smooth the movement and decrease friction points. Keyed shafts, set screws, and retaining rings 1225 were implemented at the ends of the actuators to ensure the overall rigidity of the assembly.

Initial loading begins with both stepper motors 1210 1230 turning in unison until the leading edge of the strip packaging reaches the sensor array 1415 1420 at which point the feedback from either side directs the continued rotation of the stepper motors 1210 1230 to obtain optimal orientation and location for the cut to be made.

Figure 13:
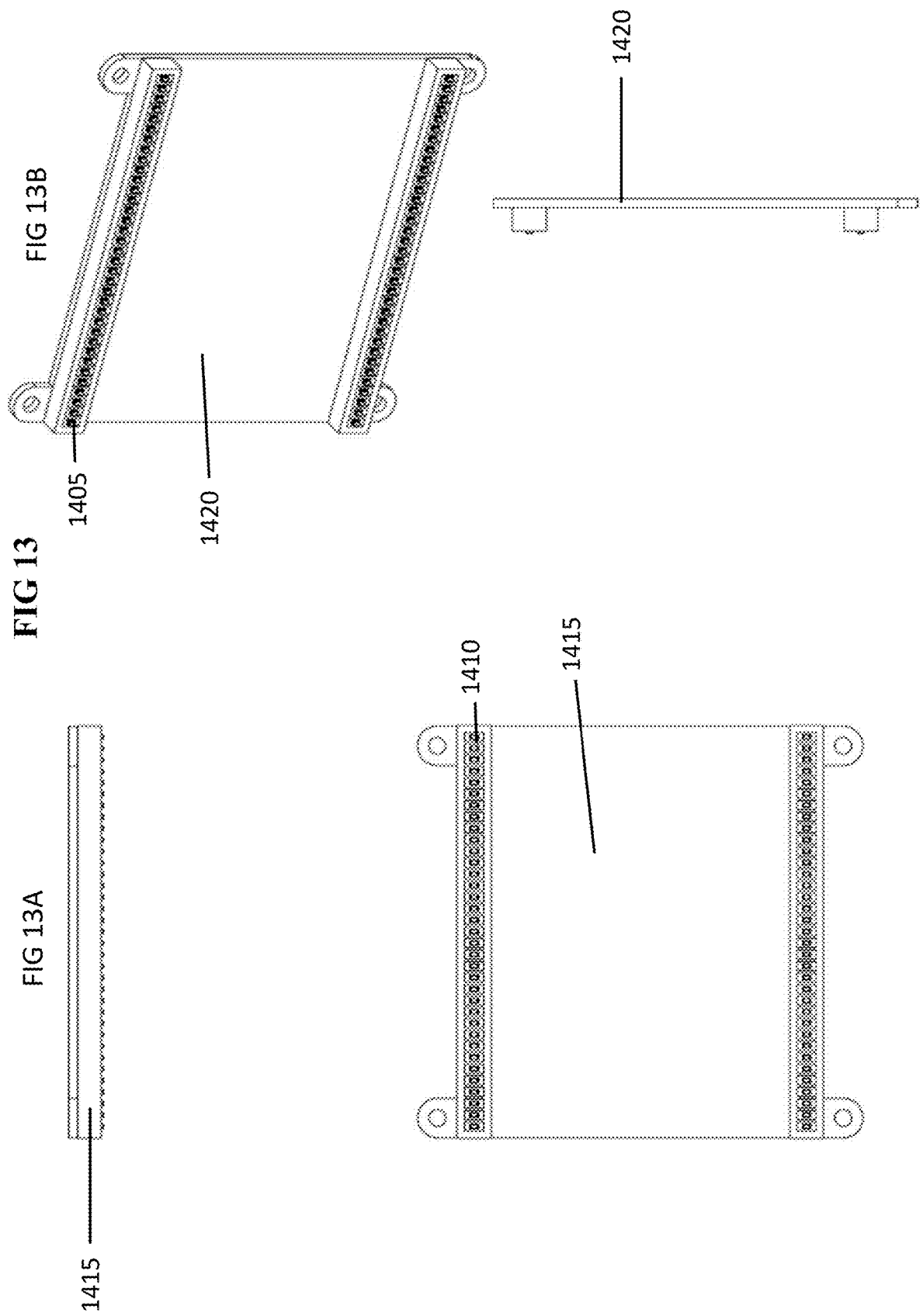
FIGS. 13A and 13B depict the top and bottom boards that collectively make up the sensor array.

A Sensor for Sensing a Location and an Orientation is disclosed where the sensor operates to evaluate the location and orientation of the leading edge of a pre-packaged tablet as it travels through the delivery apparatus. Software algorithms run by a processor are used to continuously align the pre-packaged tablet's sides parallel with the length of channel. This assembly is primarily composed of a sensor as depicted in FIG. 13, the sensor comprising two sensor plates 1415 1420 and thirty-six photo diode 1405 and photo transistor 1410 pairs. The system is designed to operate on a wide variety of packaging widths and heights. The medication within an individual pack can affect the height of the pack based on the size of the capsulated pill(s). The more height in the bag, the more pinched together the ends of the pack become and can result in a random variance from pack to pack. The design of the sensor array takes the variance into account by maintaining an accuracy with a deviance of only a few millimeters because of the number of sensor pairs built in.

Figure 14:
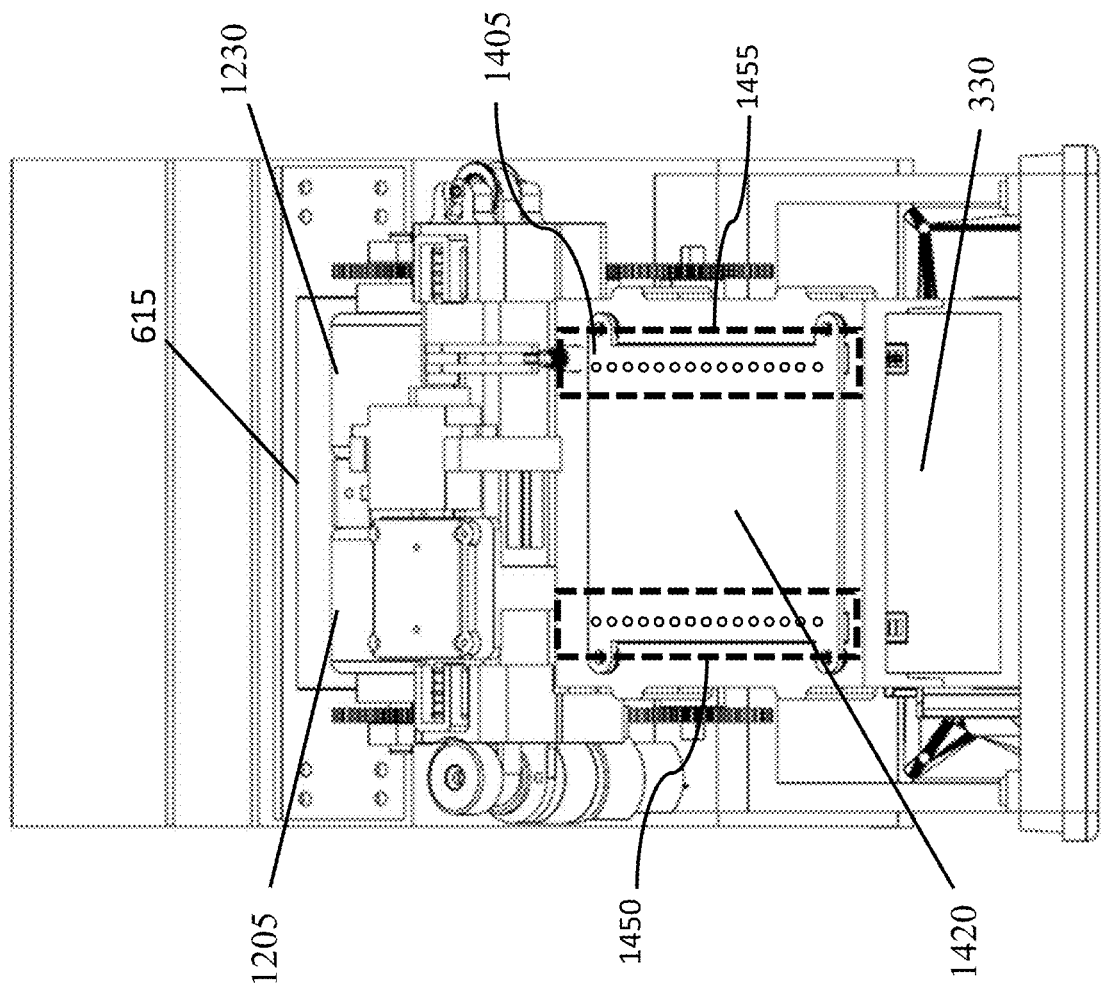
FIG. 14 depicts the mechanical components of the processor modulated differential drive delivery system, specifically illustrating placement and function of the sensor array.

Depicted in FIG. 14, the sensor pairs are positioned in linear tracks, along the left and right sides of the sensor plates, wherein the top sensor plate 1420 in some examples houses all the photo diodes and the bottom sensor plate (1415 best depicted in FIG. 8) houses the transistors to detect the diode signals.

As a simplified example, and from the perspective of FIG. 14, as a pre-packaged tablet strip progresses through the delivery apparatus from the channel inlet 615, to the channel outlet 330, it travels between the top sensor plate 1420 and bottom sensor plate 1450 progressively blocking the photo diode 1405 signals from their paired transistors underneath.

If the leading edge of the pre-packaged tablet strip is aligned, the left 1450 and right 1455 tracks of sensor pairs will break signals uniformly as the strip progresses. This typically won't be the case, and misorientation will be detected by uneven signal breaks as bulky medications can cause misorientation of the strip while delivering. When misorientation is detected the orientation software algorithm will command corrective controls to be carried out by either the left 1205 or right 1230 actuators, while continuing to measure the movement of the front edge.

Figure 22:
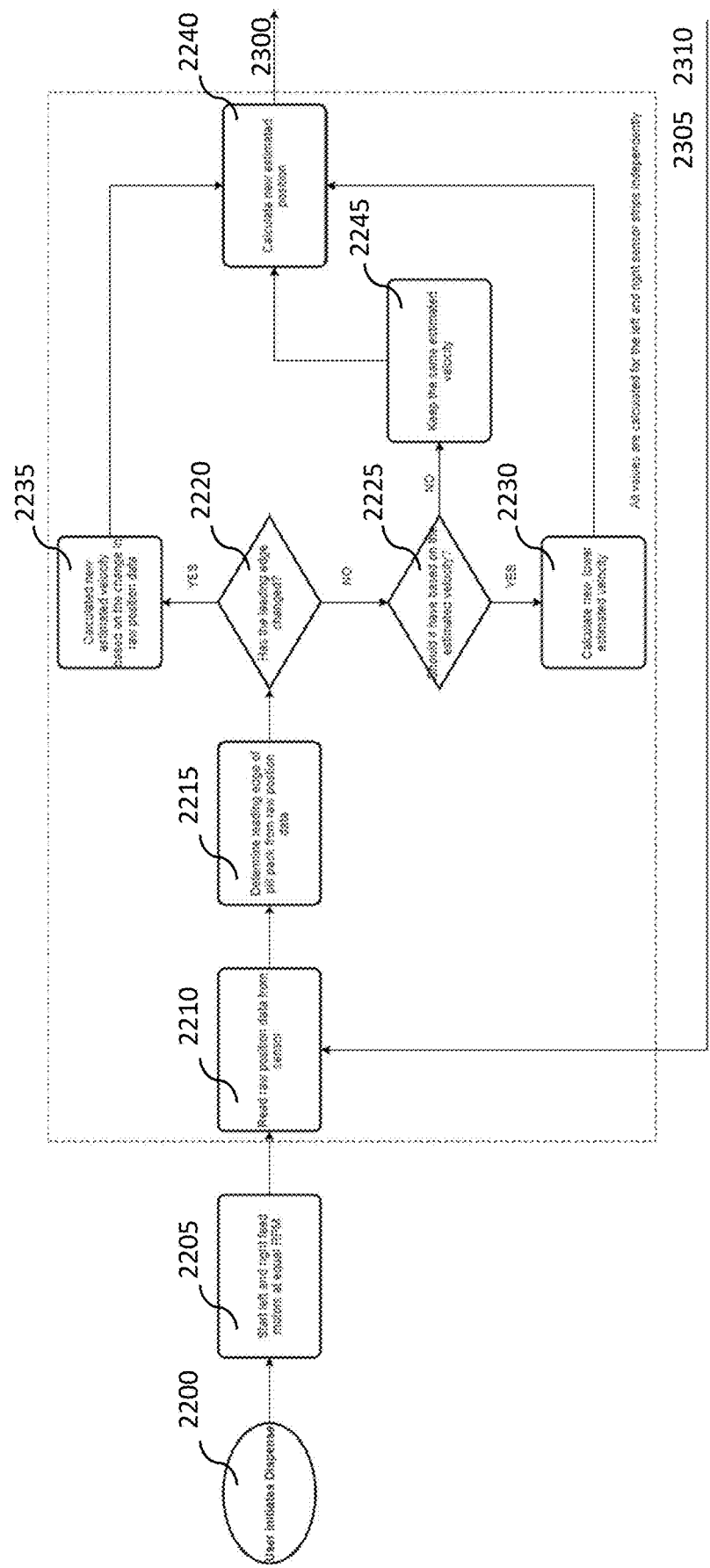
FIG. 22 depicts a logic flow of the delivery hardware and software systems.

In one example, depicted in FIGS. 22 and 23, the sensor operates as follows, at the start of a delivery sequence 2200 both stepper motors begin turning at an equal RPM 2205. A microcontroller cycles through each of the thirty-six pairs of photo diodes and photo transistors on both sides of the sensor plates at a rate of 10 kilohertz. The total time to complete a full sweep of all 72 sensor pairs is 3.6 ms. The microcontroller continuously accumulates that data into two five-byte packets which are broadcast upon a read request over the I2C bus. A processor reads from the microcontroller 2210 once per millisecond and builds the location data into a text string of ones and zeros representing the status of all the beam break pairs (photo diodes and photo transistors). A zero indicates that something is obstructing the beam and a one indicates no obstruction. A processor uses the string of ones and zeros to determine the location of the leading edge 2215 on both sides of the sets of photo diodes and transistors of whatever is passed along the sequence of photo diodes and transistors. The location of the leading edge can be updated based on the microcontroller's information at a rate of one kilohertz. As the location of the leading-edge changes 2220 from one sample to the next, the estimated velocity of the bag is calculated by recording the time lapse in between each location change 2235. The velocity is used to predict when the next set of beam breaks should trigger 2240 and when combined with the stepwise location information extrapolates a smoothed-out location curve. Both stepper motors run at full speed or a one per-unit (PU) rotations per-minute (RPM) rate at startup. The velocity estimation predicts the remaining time needed to reach the next stepwise location point and the motors maintain that velocity 2245 until the system determines that the bag is either stuck or has reached the next stepwise location. If the bag does not reach the next point but was expected to based on the last estimated velocity 2225 the system dynamically adjusts the estimated velocity. If the bag gets stuck and never reaches the next stepwise location point the estimated velocity decays to zero 2230. Depicted in FIG. 23, as the bag travels towards the target setpoint 2300, if a difference exists between those predicted locations on each side of the beam pairs and one side starts leading the other 2305, the system decreases the PU RPM of the leading side motor proportional to the amount of difference that the system detects 2310 before continuing to read the raw location data 2210. In summary, the stepwise location information is translated into a velocity, then the velocity plus its last detected, real location is used to determine its estimated location, lastly, the system runs the estimated location information through a simple rolling average filter to smooth out any kind of noise jumps. If the sensor sees a mismatch between the leading-edge locations of either side of the pill pack it tries to correct it by slowing down the feed motor 1210 1235 on the leading side.

Figure 15:
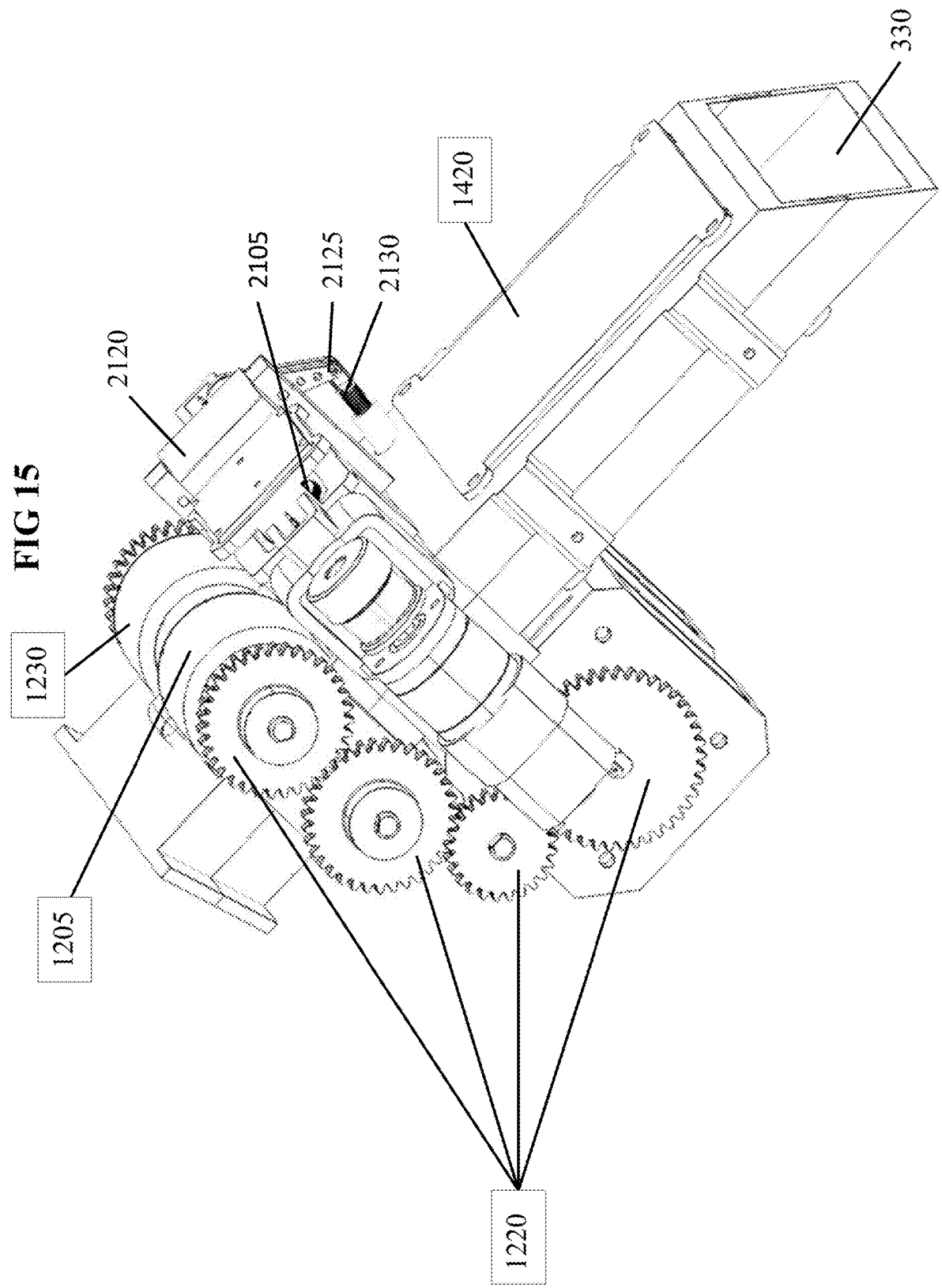
FIG. 15 depicts the pincher assembly extended into the channel, in an active cut position.

Perforation Detection is depicted in FIGS. 11B, 14, and 15, the internal camera 2105 and lighting system are used to obtain optimal orientation and location for the cut to be made. The orientation sensor array is programmed to work with the processor modulated differential drive and with cutter mechanism control logic to deliver the lead pack to the target setpoint so that the cutter mechanism 2115 will make its cut directly on the perforated line of a pre-packaged tablet 405, depicted in FIG. 4, which marks the end of one pack and the start of the next pack. The cutter mechanism control logic is configured to monitor the sensed pre-packaged tablet location and orientation feedback from the orientation sensor array, to initiate a cutting sequence responsive to at least one of the predetermined configurations within the processor and the dynamic configuration responsive to the sensed location and orientation, and to generate and log a message into the distributed database responsive to the cutting sequence. Depicted in FIG. 23, once the leading-edge of the pill pack reaches the target setpoint 2300, the dual motor drive system 1210 1235 is shutdown 2315, the cutting surface is illuminated to generate proper lighting conditions, and the fine-positioning camera 2105 captures a single image. The image is then analyzed by software to determine the location and angle of the pill pack perforation 2320. If no perforation is detected the dual motor drive is used to make a series of location adjustments, with the camera 2105 attempting to identify perforation marks between each adjustment, until, the perforation is found, or the series of location adjustments is exhausted.

Perforation Detection is depicted in FIGS. 11B, 14, and 15, the internal camera 2105 and lighting system are used to obtain optimal orientation and location for the cut to be made. The orientation sensor array is programmed to work with the processor modulated differential drive and with cutter mechanism control logic to deliver the lead pack to the target setpoint so that the cutter 2115 will make its cut directly on the perforated line of a pre-packaged tablets 405, depicted in FIG. 4, which marks the end of one pack and the start of the next pack. The cutter mechanism control logic is configured to monitor the sensed pre-packaged tablet location and orientation feedback from the orientation sensor array, to initiate a cutting sequence responsive to at least one of the predetermined configurations within the processor and the dynamic configuration responsive to the sensed location and orientation, and to generate and log a message into the distributed database responsive to the cutting sequence. Depicted in FIG. 23, once the leading-edge of the pill pack reaches the target setpoint 2300, the dual motor drive system 1210 1235 is shutdown 2315, the cutting surface is illuminated to generate proper lighting conditions, and the fine-positioning camera 2105 captures a single image. The image is then analyzed by software to determine the location and angle of the pill pack perforation 2320. If no perforation is detected the dual motor drive is used to make a series of location adjustments, with the camera 2105 attempting to identify perforation marks between each adjustment, until, the perforation is found, or the series of location adjustments is exhausted.

Figure 23:
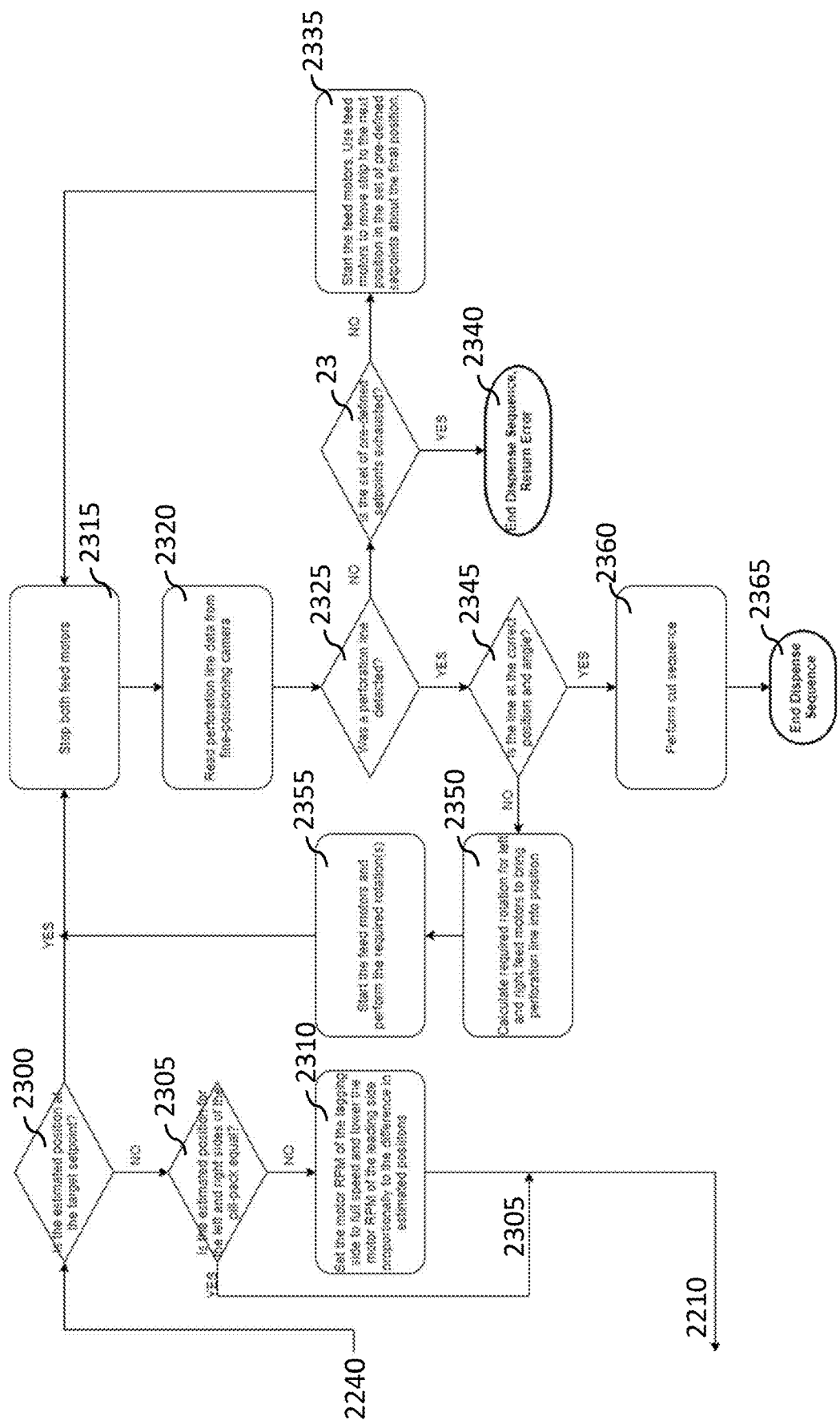
FIG. 23 depicts a logic flow of the delivery hardware and software systems.

In an example, depicted in FIG. 23, when the sensor array sweep finishes its orientation pass, the perforation is visible to the camera positioned over the cutting channel. The camera and LEDs are powered off while the sensor array sweep is in process. Once the leading-edge of the bag reaches the target setpoint 2300, the motors are shut down 2315 and the processor signals the camera to begin its algorithm 2320. The LEDs power on illuminating the cutting surface to generate proper lighting conditions and the camera captures a single image which is passed through a series of filters to extract data points that allows the system to make the final orientation adjustments. The camera attempts to identify perforation marks 2325 between each adjustment. If no perforation is detected, the feed motors make a series of location adjustments 2325 until the perforation is found or the series of location adjustments is exhausted 2330. If no perforation is found after adjustments are made, the device ends the delivery sequence and returns an error notification 2340. Under normal circumstances where a perforation line is detected, the sequence of operations is as follows. Depicted in FIG. 16A, a black mask 2705 is drawn over the image areas above and below the perforation where the channel is obstructing the camera. The remaining bar 2710 of the image is converted to grayscale to remove any colored light and then, as depicted in FIG. 16B, the image is passed through a histogram masking filter. An additional black mask is applied anywhere that the light level does not exceed a set threshold. At this time, as depicted in FIG. 16B, all that remains is a binary image of the brightest points, which is where the LED light is shining through the perforations in the bag. The simplicity of this approach is beneficial because it also summarily removes all the text on the bag that appears in the single image capture by covering it with the additional black mask applied during the histogram filter stage and removes the possibility of the text throwing off the rest of the orientation algorithm. A fast-feature detection algorithm, available within the OpenCV module, is applied after the histogram masking filter which looks for 'corners' by finding contrasting edges in the image. The contrasting edges are indicated by a bright spot (white pixels) surrounded by dark spots (black pixels). The fast-feature detection passes over the entire image finding all these 'corners', marking them, and filling up an array with the (x,y) coordinates of the corners. The coordinates are then used to populate a scatterplot graph which leaves a dotted line that represents the bag perforation. After the previous filtration steps, the only spots of light that remain are caused by the LED light shining through the perforation. Depicted in FIG. 16C, a straight angle line best fit 2905 is applied to the dotted line to find the average angle of the dotted line. The best fit line returns the y-position, starting on the left, and the angle of the line. The real location y-coordinates for each of the sides of the bag are extrapolated from the best fit line by extending it to the edges. The angle of the line and the y-locations are used to instruct the dual motor drive system to correct any remaining misorientation 2350. After all necessary corrections are made 2355, the cut sequence initiates 2360 and the delivery sequence ends 2365.

In one example, the processor may be represented by but not limited to a Raspberry Pi 4.

In another example, modern Convolutional Neural Networks (CNN) research of lane detection for vehicles is leveraged to calculate a location and angle of bag perforations 305 regardless of the manufacturer. CNNs are traditionally adequate at object detection, but poor at giving pinpoint spatial and location information. The new Spatial CNN (SCNN) method makes up for these shortcomings in a computationally efficient manner. A large training set is used to train the CNN on pre-marked splines indication perforation with which the location and angle of bag perforations created by any manufacturer can be identified with high accuracy. A CNN in conjunction with a camera 2105 and lighting solution allows other features comprising bag reel damage detection, medication detection within the bag, and text-extraction from the bag labeling, to name a few, to be implemented in other examples A Rotary Suspension Cutter Mechanism is depicted in FIG. 11B, at the start of the cut sequence, the pinching mechanism is engaged to ensure no movement of the pre-packaged tablet strip at the start of the cut. (The pinching mechanism in its current design is located offset toward the non-motor side of the cutting channel right below the cut line to maintain ample tension for the start of the cut). The pinching mechanism comprises a single servo motor 2120 and a lever arm 2125 with a hinged metal rod 2130. When engaged, the metal rod 2130 is lowered into the main medication channel to provide pressure onto the pre-packaged tablet strip just below the cut location. The end of the rod includes a spring-loaded tip of rubberized material 2510 for grip. The added spring 2515 is adjustable for tension, allowing ample pressure onto the pre-packaged tablet strip while allowing some travel. Outside of the cutting sequence, the metal rod 2130 shall be lifted entirely out of the main channel to prevent blockage.

Figure 12:
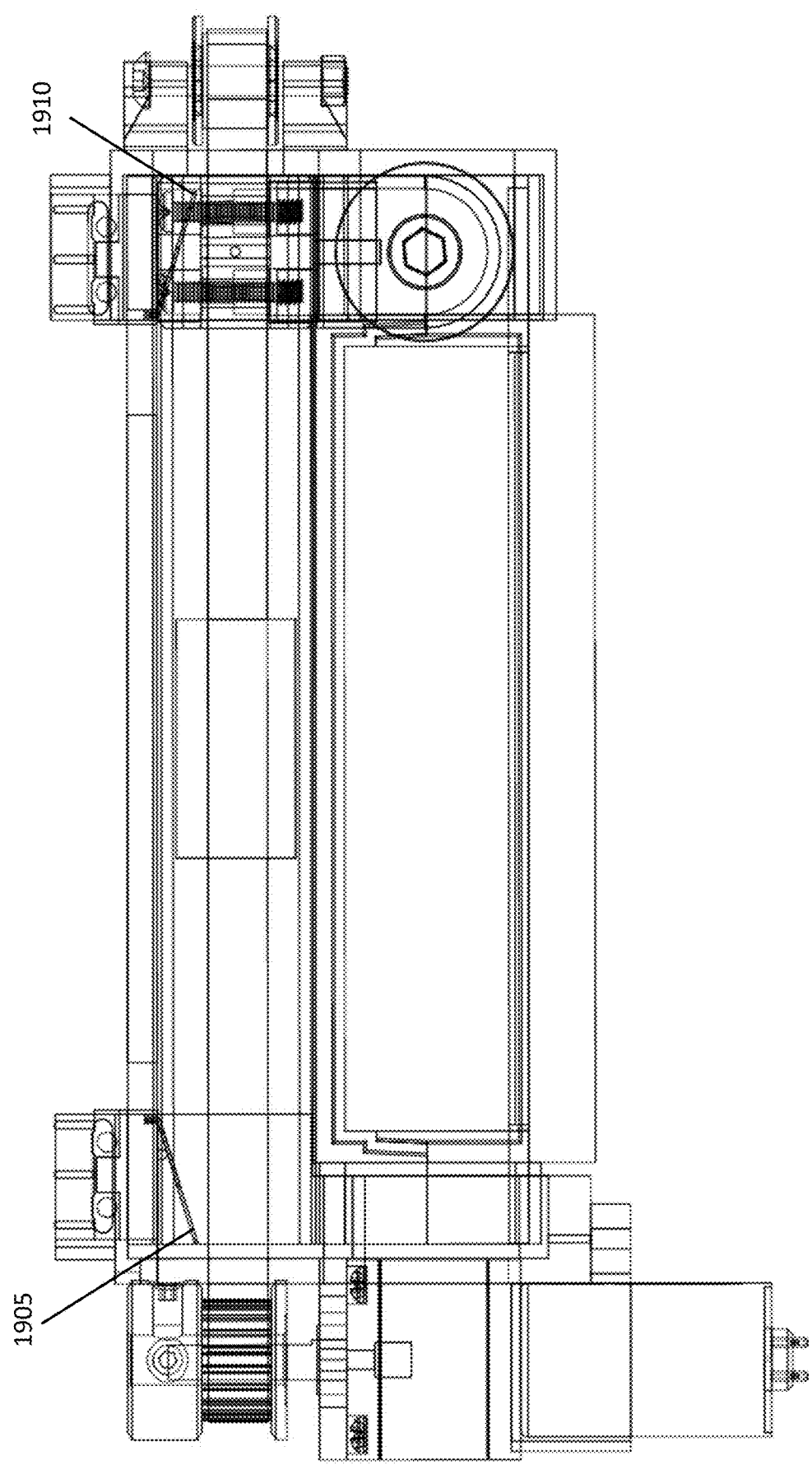
FIG. 12 depicts the cutting assembly with all hidden lines revealed to show clarity of the internal structure of the cutter mechanism, specifically the limit switches housed within.

Depicted in FIG. 10, the cutting mechanism includes a rotary blade 1805 housed within a carriage assembly (shown in two parts as 1810 and 1815). A suspension system assists the rotary blade 1805 by using two compressible springs 1820 1825 to relieve downward force of the blade and prevent jamming/stoppage. The compression force of the dual springs 1820 1825 provides even, downward pressure to the cutting surface. Two adjustable screws 1830 1835 are used to control the amount of tension in the springs 1820 1825 and vertical travel distance of the rotary blade 1805. The rotary blade 1805 cuts against a self-healing cutting mat commonly made from layers of PVC or Polypropylene (PP) which gives slightly to the force of the blade. The texture and non-rigidness of the surface decreases the pre-packaged tablet movement as it is being cut as well as wear on the rotary blade 1805. A rotary blade 1805 is used to make a clean straight edged cut across the intended perforations 405. The rotation of the blade 1805 as opposed to a stationary blade allows it to glide evenly across the surface of the bag versus creating a pushing action on the bag. Depicted in FIGS. 11A and 11B, the carriage 2115 is driven from the carriage housing area 2135 by a belt 2140 using a DC motor 2145 and toothed gear 2150 on one side of the channel and an untoothed idler pulley 2155 on the other. *Advantages of a belt/pulley system versus gears/a linear rail are, the use of the DC motor 2145 allows for faster cutting speeds, lower cost, noise reduction, and space saving. Depicted partially in FIG. 11 but most clearly in FIG. 12, installed at each end of the cutting channel are limit switches 1905 and 1910. As the carriage 2115 reaches an end of the cutting channel, it physically depresses the corresponding switch 1905 at that end of the cutting channel. Switches work in conjunction with a 2 Way DC Motor Driver Module (H-Bridge circuit) to control DC motor 2145 function. Once the limit switch 1905 is triggered, the motor 2145 reverses direction. The cut is completed when the carriage 2115 re-enters the carriage housing area 2135 and triggers the other limit switch 1910. Each end of the cutting channel extends beyond the main channel where the pre-packaged tablets travel when not in use.

In other examples, the width of cutting channel is expanded. Optimization can be achieved by creating carriage housing areas on each side of the channel, eliminating the need for travel in both directions, decreasing cut speed, motor use and noise, blade wear, and cutting mat wear.

"Remote Patient Monitoring" (RPM) can be described by some as including a broad number of services. As described in this section, it shall relate specifically to data collection and analysis from additional devices that are utilized for measuring general health vitals. This is different from other modules such as medication management, as described in other parts of this disclosure, and is also different from wellness checks and telehealth capabilities, but it should be understood that the combination of these distinctly discussed "modules" may be used in coordination with one another for what may be generally defined by some as "patient monitoring".

RPM devices are connected to the disclosed hub as depicted in FIG. 24 to provide additional forms of health data about the home patient. The patient 2460 would initiate contact with one of the RPM devices, which are either integrated into the hub as wired hardware 220 or as wirelessly connected hardware 245. The RPM device, being prompted would interact with the hub pluggable component API 230 designated for the RPM module. The data collected is held briefly by the hub's local storage within the core framework 225 before being passed to the cloud service 255. The cloud service accepts this data through the cloud pluggable component 250 designated for the RPM module wherein the data is analyzed across a set of metrics set for the data type, and depending on that analysis, is either stored for request driven reporting, or will additionally prompt an event driven alert that is pushed to a remote support entity 2470. In some examples the remote support entity will deploy the caregiver 2465 to intervene if there may be reason for immediate concern, wherein the caregiver would then make contact with the patient 2460.

Examples of these devices include a device to measure a patient's blood pressure, blood oxygen levels, heart rhythms, weight, temperature, oxygen levels, or any vitals commonly used to evaluate a person's general health status. Many of these health vital devices exists today with built-in Bluetooth or other wireless connectivity. In some examples this would allow the hub to wirelessly communicate with and aggregate the data from the additional device in real time. In terms of interface integration, additional devices will contain an existing user interface through an external app, website, or on the physical device itself. In this case, the disclosed system collaborates with additional devices by utilizing the hub external API(s) and configuring pathways for a multitude of systems to translate data into a format compatible with the system and usable for the event driven and request driven data reports.

The Telehealth communications module enables a wide variety of remote interactions for the home patient. These frequently include Nurse consultations, Counseling sessions/psychology treatments, guided physical therapy, or any other health services where non-contact interaction does not impair the treatment method.

A health care professional (HCP) may benefit from telehealth and the frequent contact with a patient it provides due to the apparatus' WI-FI and cell connectivity. Additional benefits include an increased ability to reach the underserved.

In some examples, the patient uses the device's microphone 205, speaker 1005, and touchscreen 215 depicted in FIG. 3 to connect with a health care professional on a secure video call from the patient's home. Communications between a patient and a primary care physician can include follow-up appointments, to ask/answer questions about test results, or to discuss any other health related concerns they might have. These communications are enhanced by the hubs ability to provide video conferencing, giving the same personal level of care that an in-person meeting offers. The functions of the telehealth communications module are greatly enhanced when used in combination with the capabilities of the Medication Management module, Remote Patient Monitoring module, and Wellness Check module. In the case where a patient uses telehealth.

In some examples, a Personal Emergency Response system (PERS) module may be integrated into the wellness system described herein. Execution of this function may be conducted similarly to other alerting processes disclosed, adapted to meet expectations of an emergency situation as necessary. The PERS may be implemented physically into the apparatus, as a separate accessory, or some combination thereof.

Integration of a PERS module allows the patient to call for emergency response at any time. One example of the PERS module when a user hits the PERS button, connected to the hub as either wired hardware 220 or a wirelessly connected piece of hardware 245 (such as frequently worn PERS pendants). In either case, the button sends a radio signal to the PERS hardware board within the apparatus, this hardware board comprising a radio receiver, a microcontroller, and a cellular network module. The PERS hardware board would initiate a 2-way voice call to a remote support center 270, over a connection such as VOLTE or VOIP. The microcontroller of the PERS hardware board will then notify the hub of the event. The hub will then log the PERS event to a local data storage. The hub would then display a cancellation button on the digital display to allow the user to cancel the distress call in the event the call was made in error. If the call is not cancelled, a two-way conversation will commence between the patient and a remote support person 270 who will arrange immediate help for the distressed patient 260.

In some examples, Wellness Checks Module is an implemented of the HMS. Wellness checks as described in this section relate specifically to an interactive, personally designed questionnaire presented to the patient.

A wellness check presents the patient with one or more questions, typically repeated over a certain amount of time which would provide pertinent information about the health and wellness of the patient. These inquiries and their responses may aid in evaluating things such as a patient's reactivity to a medication, post-surgery status, mental health, or status of a chronic condition without the need for frequent clinical appointments.

The implementation of the wellness check module as a component of the HMS can be visualized in FIG. 24 wherein the system cloud service 255 sends one of a personalized or generic style wellness check survey to the hub 200. In some examples, the style of survey will depend on the health history of the patient and be assigned to the patient by a person depicted in the figure as a "remote support" person 2470. The wellness check is pushed to the cloud pluggable Wellness Check API 251 to the Wellness Check API within the hub 231. The hub then displays the health questionnaire on the touch display 217 where the patient will provide input to the survey.

In some examples, wellness checks provide the patient a set of simple questions wherein each consecutive question in the set is affected by the response of the previous. Once all questions stored within the patient's wellness check survey have been addressed it is sent back to the cloud service where the patient input may be evaluated by a remote support entity 270. This evaluation may be done automatically or manually. In some examples these wellness checks may include questions which have a built-in mandatory support action, or event driven message 2530 as depicted in FIG. 25. An example of this would be a severe response received from a patient taking a new antidepressant medication, or a patient who is on observation after major surgery. Like other "modules" discussed, the collective results become a valuable reporting tool for additional clinical or caregiver interpretation.

HMS Data Collection is the patient data pipeline is shown in FIG. 25. Data sources 2510 exist in each HMS module, and are collected from at least one of a hardware component and a software component. Examples of hardware components are heart rate and blood pressure monitors, the PERS button, or delivery apparatus. Data sources can also be pure software components, such as the data collected from Wellness Checks.

Data sources generate patient data 2515 upon interaction with the patient 2505, utilizing the appropriate hub pluggable component 230-233 shown in FIG. 24. The patient data is sent from the hub to the cloud service, using a secure web service call. The patient data is then stored in a secure database 2520. A reporting engine 2550 allows an authorized user 2555 to pull detailed and aggregated reports.

Upon new patient data becoming available, the data analyzer 2525 examines the new data, sometimes in combination with historical data, and evaluates if there is an out of tolerance situation. In this case, an exception message is created and pushed to the appropriate service, with the message router 2530, for remedial action to be taken. An example of an out of tolerance situation could be a blood pressure reading that lands above a maximum threshold value. Another example could be the time a pre-packaged tablet is delivered is outside of the threshold for being "on time".

The Data Management Architecture of the implemented will follow some common IoT device and data management architecture principles. The first of these principles is security spanning over the application lifecycle in general including the development, deployment, and maintenance of the application.

The second principle is scalability which handles the changing needs of an application within the confines of the infrastructure, matching resource capacity to the demand.

The third principle is extensibility, where through the addition of new functionality or through modification of existing functionality, the application may be leveraged across adjacent industries. This principle involves utilizing an application programming interface (API) capable of providing third party services and applications that encourage the overall extensibility of the back-end operations, and the invention as a whole.

The fourth principle is recoverability. This principle encompasses the anticipation of any failures, at all levels and to recover from any failures.

Figure 26:
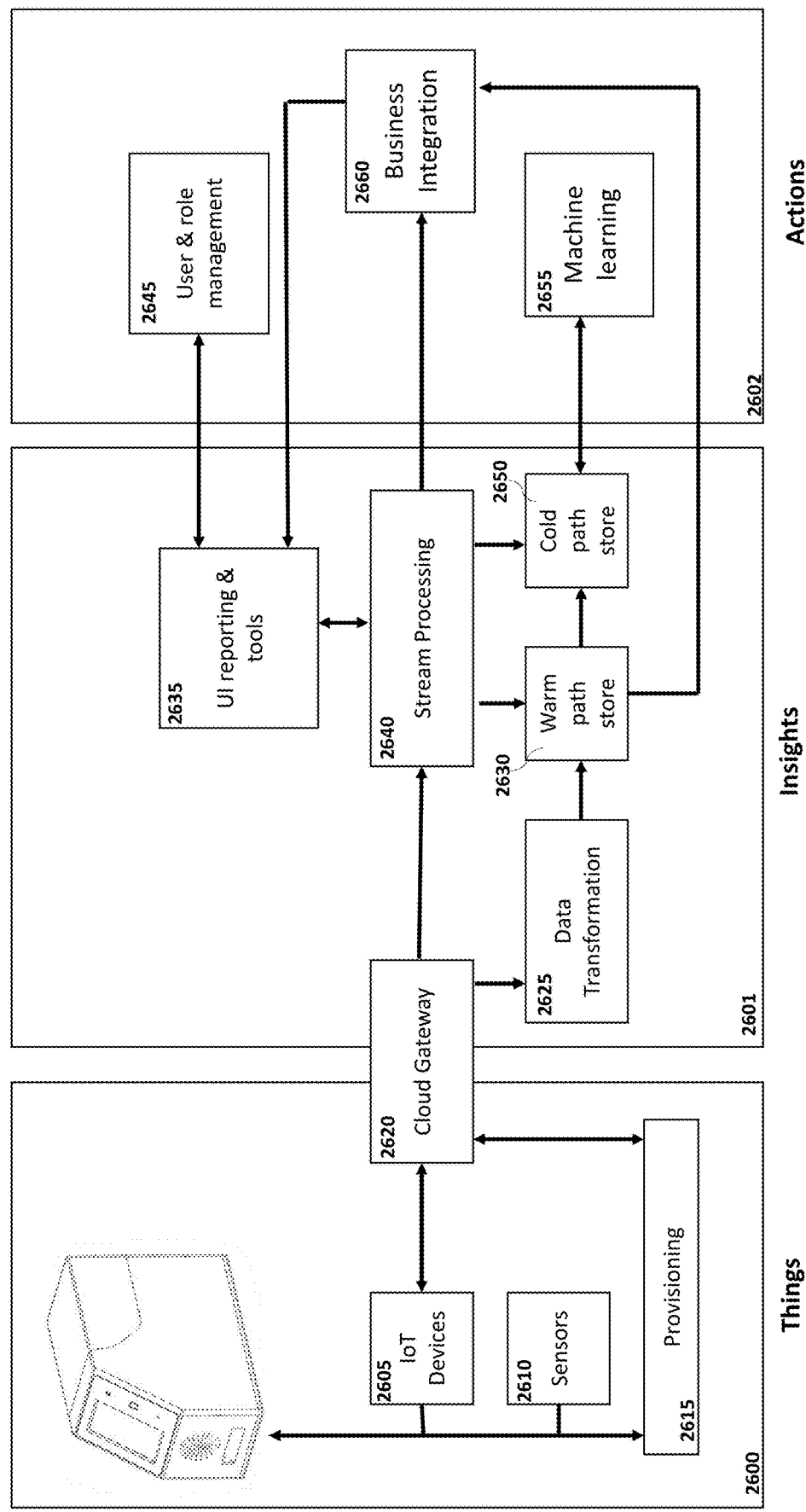
FIG. 26 depicts an architecture for data management.

The fifth principle is manageability and configurability, where the architecture is designed to be cost-effective to develop, operate, support, and manage. This framework is organized into three categories, as seen in FIG. 26. These modules include Things (2600), Insights (2601) and Actions (2602).

The "Things" module represents a broad array of data enabling devices (2605) and sensors (2610). Our architecture includes one or many FDA certified application server(s) following a unique, custom built Integrated Modular Architecture. Each application is hosted in the application server or servers runs in a protected, sandboxed, virtual environment and is, itself, uniquely and independently certified at a level of certification required for a defined use case. That means that the integrated modular architecture is capable of hosting multiple workloads with various levels of regulatory requirements. These workloads can include health care partner applications, data services, telehealth partners, APIs, EMR (Electronic Medical Record) gateways or applications such as EPIC or CERNER and other applications requiring HIPAA and FDA regulatory compliance.

The bulk provisioning layer (2615) handles device management and provisioning and is integral to the architecture's security, deployment, and high availability & disaster recovery capabilities. Connecting the "Things" module (2600) and the "Insights" module (2601) is a Cloud Gateway (2620) which acts as an interphase.

The insights module (2600) represents the messaging layer. This is also a common messaging architecture. The Insights module (2601) connects to the Things layer (2600) through the messaging and cloud gateway (2620). The Cloud Gateway securely handles data and logic pathways and mechanisms. Data is forked into two pathways. The first one is Data Transformation (2625) which handles data discovery, data mapping, code generation, code execution, data association and data review functions all handled primarily in a batch mode. Once transformed, data is initially routed to a Warm Path Store (2630). The Warm Path Store (2630) is the core of the insights layer as it is the reference data set to be leveraged by our business integration (2660) in the Actions layer (2602) and generates real-time actionable analytics.

Actionable data is then available and presented through the UI Reporting & Tools module (2635) to users across broad areas of responsibility: a home health provider managing a panel of patients, a hospital administrator managing and supervising a team of home healthcare providers, a compliance director managing Medicare and Medicaid reporting and audits, or a customer service manager tracking patient outcomes and experience.

Further communication to the various stakeholders is the second data path from the Cloud Gateway (2620), called Stream Processing (2640) which acts as a listening system. As the name implies, this is a data stream that reports system states which are mapped against pre-determined variances and the rules that trigger notifications when these variances are exceeded. The processed streams, events, transformed data and any registered user intervention through the User & Role Management component (2645) is then made available indefinitely in a Cold path store (2650) which becomes the permanent data repository and the source data leveraged to train AI and Machine learning modules (2655). This is the module that alerts home health providers, and if opted in, familial care givers via dashboards, texts, and other prompts to intervene.

The actions module (2602) contains standard aspects such as the user management, which allows for the common roles-based activation and de-activation of various levels of data and access. Another aspect is that the action module accounts for processed and packaged data to be delivered to applications via an application program interface (API).

The message framework also follows a traditional architecture. The modular architecture enables a Data Pipeline and an Integration Message Broker. The Data Pipeline handles the reporting of all data, including the state exception data, as well as Bundled Event Batch Data and may be either transmitted in real time or in batch. The Integration Message Broker mediates communication among applications. It serves function specific applications such as handling patient data, patient wellness parameters, application data, and message Sessions and Deferral. These two modules are supported by a publish/subscribe API enabling an Events Grid. The API tracks, in a continuous timeline structure, any events triggered by a predetermined set of parameters. These include events such as medication adherence completion, non-adherence, patient routine activity or lack thereof. All parameters form a data stream that is recorded individually, in an event timeline. The Services Bus Integration Broker analyzes any state change data and, applying role based rules, makes it available as reporting data for all roles and recorded into EMR systems for care givers to track. ALL supported by a data integration layer with warm and cold or warehouse data storage.

Figure 21:
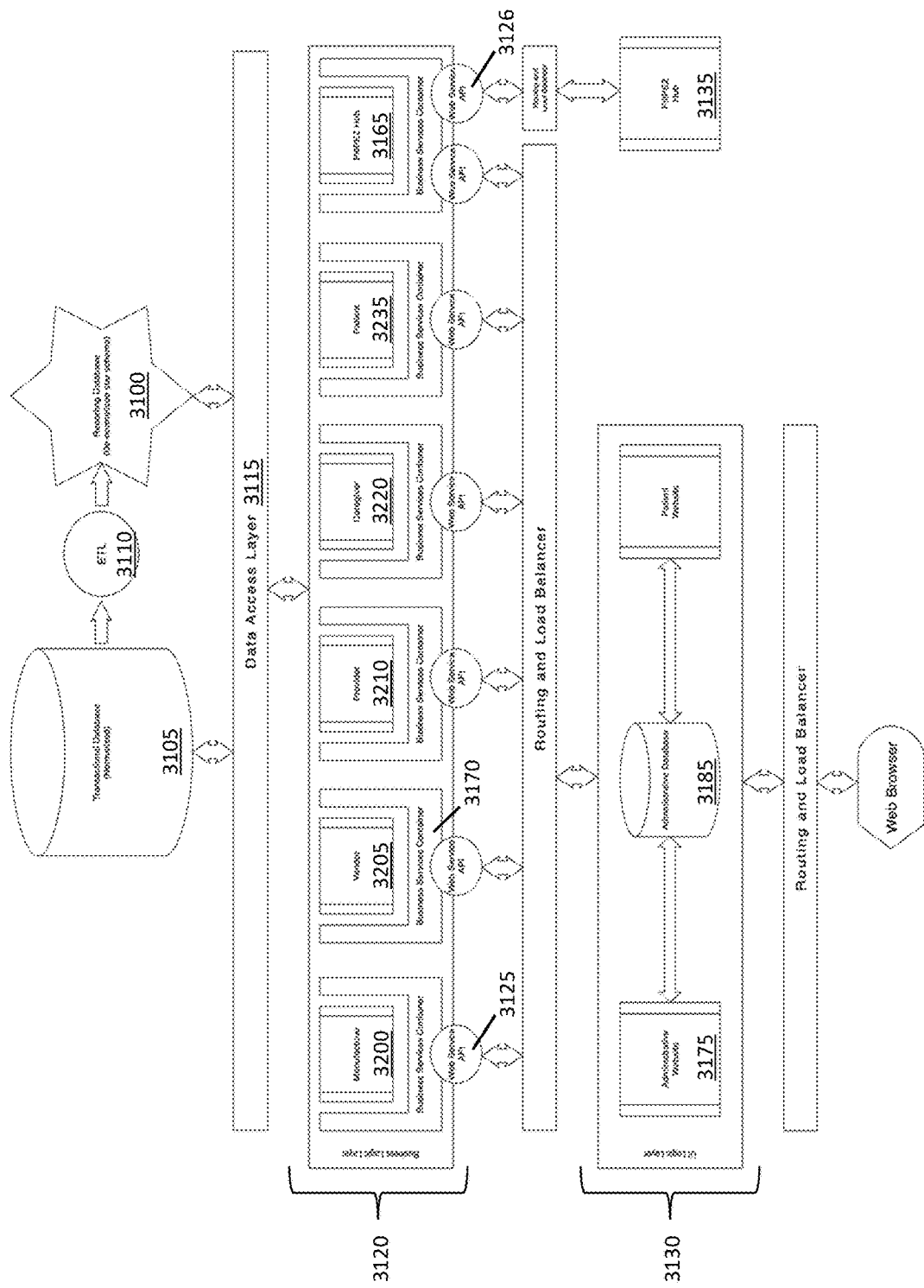
FIG. 21 depicts the cloud system diagram, showing the high-level logic layers.

FIG. 21 depicts some of the high-level layers of the cloud service architecture. The cloud service comprises a transactional database 3105, a reporting database 3100, business/domain logic 3120, web service logic 3125, and user interface (UI) logic 3130. The cloud service can be deployed using a managed service, such as Amazon Web Service or Microsoft Azure. The managed service supports, thus allowing for horizontal scalability.

Figure 18:
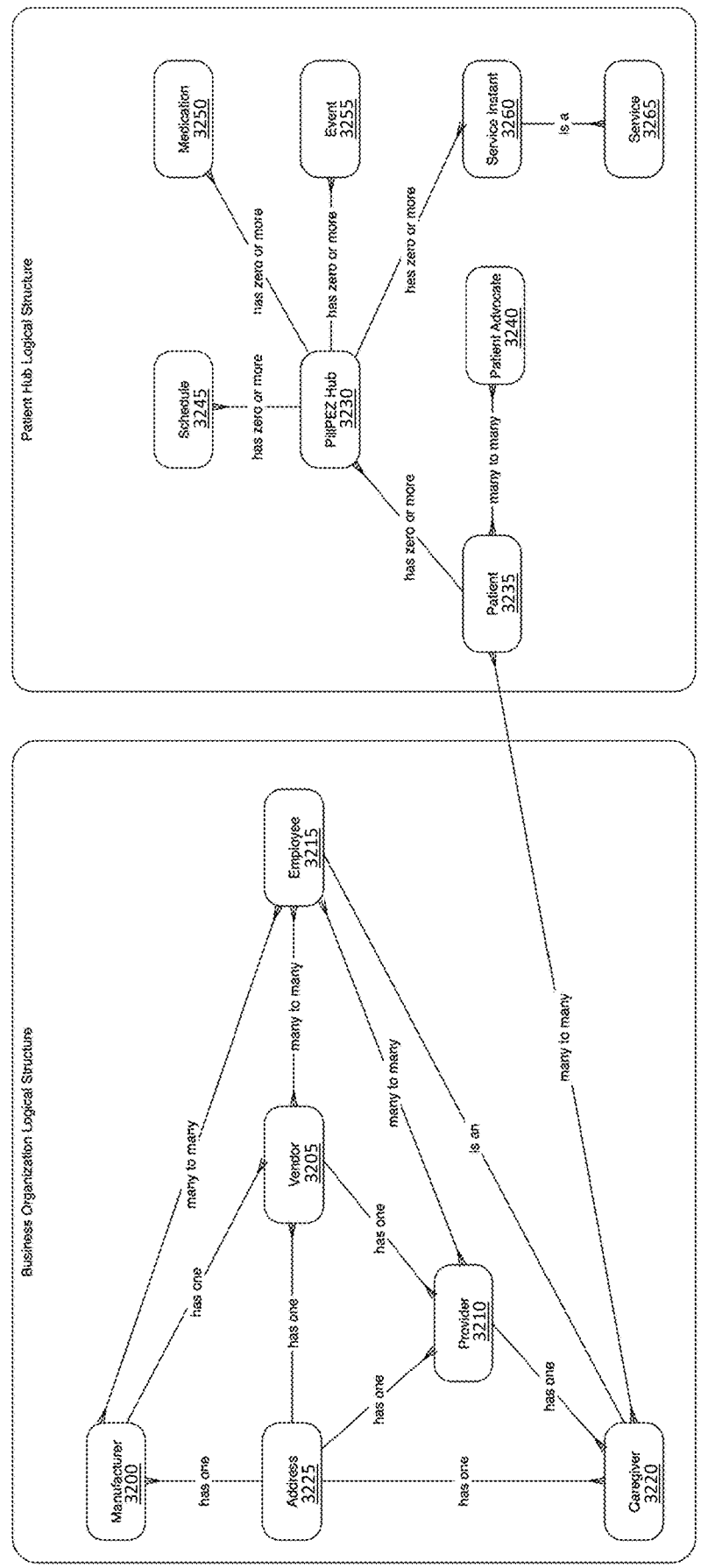
FIG. 18 depicts a diagram of the entity relationships for the business organizational structure and patient structure.

The transactional database logical schema, shown in FIG. 18 is divided into two functional domains: Business Organizational Structure, and Hub logical structure. The Business Organizational Structure defines a hierarchical relationship between the organizations that provide product and/or services. The example model has manufacturer 3200 as a "root" organization. Zero or more manufacturers may exist. A manufacturer may supply product to zero or more vendors 3205. In turn, a vendor may resell product to zero or more providers 3210. Each organizational model may have zero or more employees 3215. Permissions and access rights to data and functionality are provided by a separate system, such as LDAP, and represented by the administration database 3185 in FIG. 21.

Patient Hub Structure—represents a hub configuration, for both service logic and data, in the cloud. Configuration parameters, delivery details and schedules, and software services to support additional hardware devices are managed within the cloud environment and "sent" to the hub as required (on-boarding and upon modification).

The reporting database 3100 exists to maximize the efficiency of reporting. This is achieved by removing load from the transactional database, employing an optimized star schema, an de-normalizing the data. An Extract, Transform, and Load (ETL) process 3110 copies data from the transactional database 3105 to the reporting database 3100 in real-time or batch.

The data access layer 3115 abstracts the database API's and converts objects to and from the database domain (e.g. RDBMS) and the business logic domain (e.g. Java objects, XML, JSON etc.).

The Business Logic Layer 31120 provides services, via a Web Service API 3125, for consumption by the UI Logic Layer 3130 and the Hub 3135. Services are broadly divided up into units by business hierarchy. For example, Manufacturer 3200, Vendor 3205, and Provider 3210. Each of these functional units, or micro-services, execute within a container, such as Docker. Horizontal scalability is achieved by replicating a container 3170 where needed.

The UI Logic Layer 3130 acts as a visual front end to the business logic web services API, as well as managing access rights to users and user roles. Administrative roles are associated with the major organizational types. For example, manufacturer administrator, vendor administrator etc. An administrator is able to create users with roles defined at a lower organizational level, but not for a higher level. For example, a vendor administrator can create a provider administrator, but not a manufacturer administrator. Furthermore, users may only be created for organizations that are subordinate, or children of the creating organization.

Figure 19:
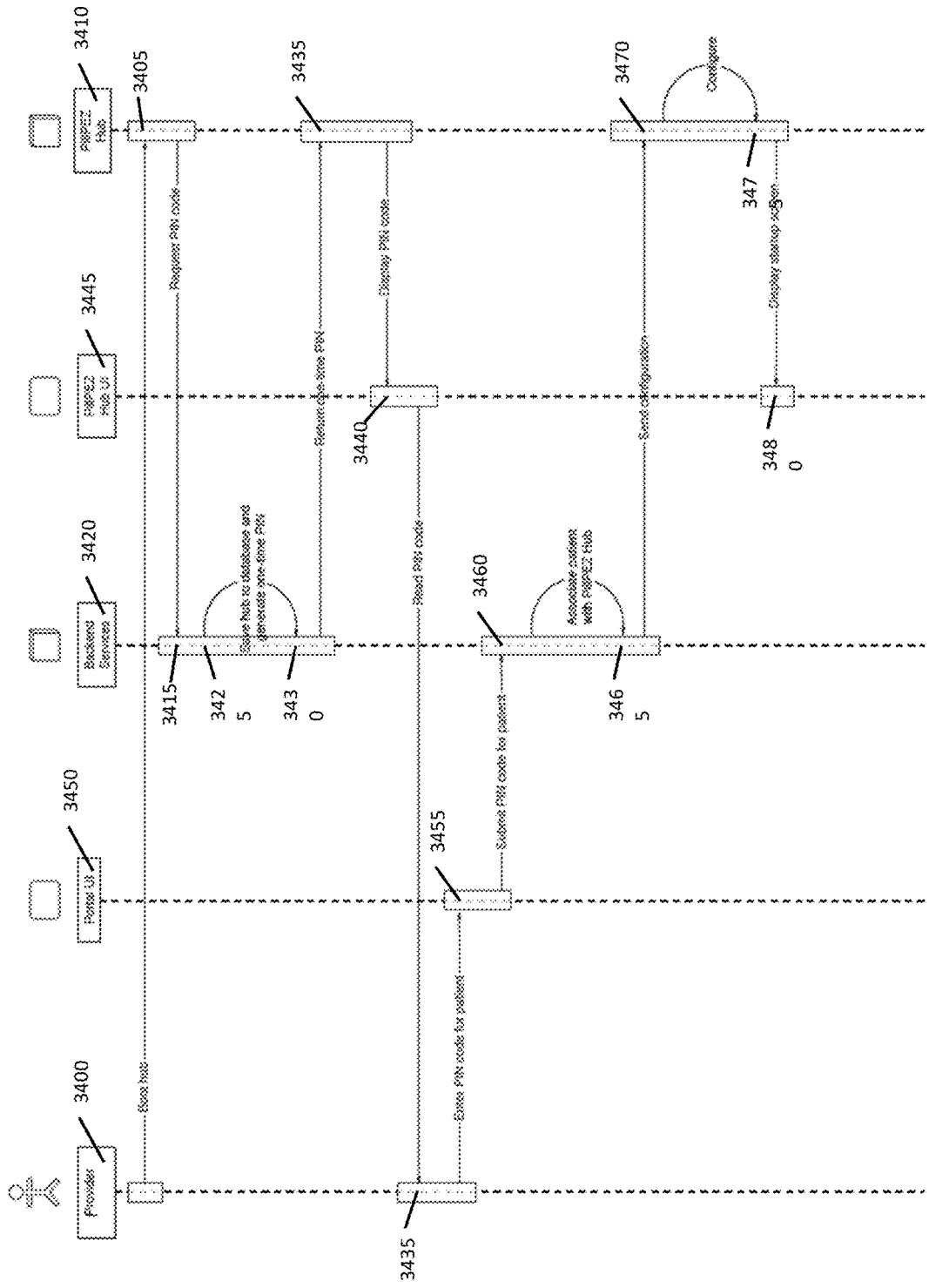
FIG. 19 depicts a diagram of the initial configuration of the hub on the cloud service.

In a discussion of Hub Configuration, FIG. 19 depicts the backend view of the initial configuration when on-boarding a new hub. This figure shows the provider/caregiver 3400, having already created the patient account in the web app, boots (turns on) 3405 the hub 3410. The hub 3410 then requests a PIN code 3415 from the backend 3420, using a web service call. The backend 3420 generates the PIN 3425, stores it in the device record 3430, and returns it 3435 to the hub 3410. The hub 3410 then displays the PIN 3440 on its screen through the Hub UI 3445. The provider 3400 will access the patient record in the portal UI 3450 and choose the option to add a device. The PIN code can then be entered 3455 into the portal. If the PIN code is known 3460, the business logic will then associate the device with the patient 3465. The device is notified, then requests its configuration data 3470 from the backend, then loads the configuration 3475, and then displays the startup screen 3480.

Figure 17:
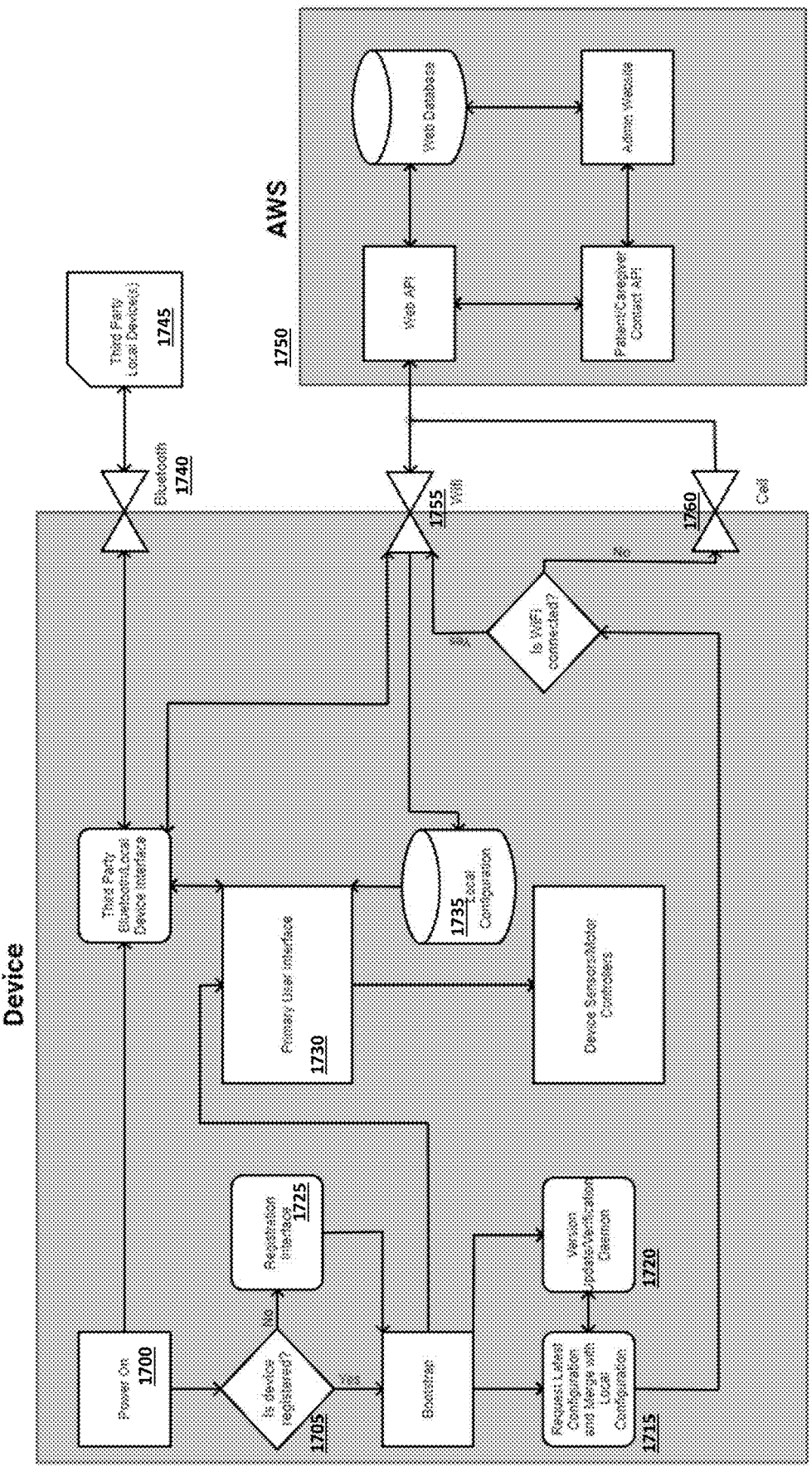
FIG. 17 depicts the hub startup processes.

FIG. 17 expands on the discussion of initial hub configuration from a device level perspective. This flowchart gives a rough abstraction of the software architecture of the hub and how it interacts with an AWS cloud infrastructure as well as third party devices. By starting from the "Power On" card, one can see when different sections of the software are activated, and how they interact with each other.

When the device is first powered on 1700, it will immediately attempt to establish a connection with any configured third-party devices 1745 over Bluetooth 1740 and WiFi 1755 (after OS bootstrap). It will also check if the device has been registered 1705. If not, it will run a special interface for first-time registration 1725 and if so, it will start the main user interface 1730 as well as fetch the latest configuration from the AWS backend 1750 Additionally, a simple daemon 1720 is created that will periodically check in with the backend to both verify the connection is active and to check for any new configuration versions 1715 allowing for live updates to a user's schedule and other settings. The device will also be able to use either WiFi 1755 or a cell connection 1760 to communicate with the backend. The configuration is stored locally 1735 so that the device will remain useable even if both connectivity options are unavailable.

Once this link is made, the device may prompt the user for some initial setup procedures depending on the settings selected on the web app. If user authentication is enabled, methods such as fingerprint or facial recognition will require an initial setup by the authorized user. All other set up is optimally done ahead of time to reduce any complexity perceived by the user, and to provide a straightforward "plug and play" device.

In a discussion of market benefits, the hub modules are provisioned to work in any combination, making it easy for any organization to adopt. Along with the modular hub design, the integrated reporting aspect of the invention is also designed to be customized per use case. The reporting can be edited to provide select data so that feedback is streamlined and succinct.

Hospitals, clinical groups, managed care organizations and home care providers (commercial or family) find benefit and utility with a value-based appraisal of the system and are expected to benefit from all hub modules. This model provides value by reducing the amount of man hours, or in-person care, required for each patient as well as by reducing hospital readmissions by keeping users on care plans, adhering to medications, and by monitoring vital signs readings. With the potential for reimbursement for care coupled with deferring rehospitalization costs, both hospitals and home care providers may find value in implementing some amount of remote management of patients.

Providers who receive reimbursements through Medicaid/Medicare benefit significantly from the medication management, remote patient monitoring, and personal emergency response system modules. These modules provide a source of CPT code-based reimbursement without an increased demand for employed time and labor. The technology also allows reallocation of caregiver hours to provide additional support within capitated payment systems. This may provide an additional source of both value and reimbursements.

Clinics, Home Care Group, and others who operate under a fee-for-service model benefit similarly to Providers/Resellers who heavily rely on CPT code reimbursements and reimbursements through insurance for these outpatient services. These groups may differ from providers/resellers as the beneficial modules of the system would likely include the medication management, remote patient monitoring, and wellness check modules.

Hospitals and Home Health Providers which operate under a value-based approach benefit from all hub modules because each module assists with raising the quality of care which in turn raises the potential for state rewards and better resource management. Providers/Resellers who operate by billing CPT codes and receiving reimbursements through Medicaid/Medicare benefit from medication management, remote patient monitoring (RPM), and personal emergency response system (PERS) because these modules provide an additional source of CPT code generation which provides more opportunity for reimbursement. Clinics/Groups who operate under a fee-for-service model and like Providers/Resellers also heavily rely on CPT code reimbursements and reimbursements through insurance, benefit from the medication management, remote patient monitoring, and wellness check modules because of the CPT incentive. Medication management covers adherence and reminder aspects that work to keep a patient in compliance with a medication schedule, Remote Patient Monitoring (RPM) covers additional accessories such as a blood pressure cuff, heart rate monitor, pulse oximeter, weight scale, to name a few, that provide feedback data in real-time to help monitor current health status as well as predict future health issues, Personal Emergency Response System (PERS) covers rapid response assistance that brings care to a person in need in an efficient and timely manner, Wellness Checks cover automated prompts supplied to the patient through the device UI, for example, "How are you feeling today (1-5)?", "Are you exhibiting any flu-like symptoms?", "What is your current pain level (1-10)?", as another feedback loop to provide real-time data to help monitor the current health status of the patient and to assess, for example, whether proper rehabilitation measures are being followed.

The following discussion comprise but are not limited to a number of alternate examples of the HMS. In a first alternate example, electricity required to drive and power the hub device could be supplied through wireless power transmission. Wireless power transmission (WPT) or wireless energy transmission (WET), or electromagnetic power transfer is the transmission of electrical energy without wires as a physical link. In a wireless power transmission system, a transmitter device, driven by electric power from a power source, generates a time-varying electromagnetic field, which transmits power across space to a receiver device, which extracts power from the field and supplies it to an electrical load. Utilizing the technology of wireless power transmission can eliminate the use of the wires and batteries, thus increasing the mobility, convenience, and safety of the HMS device for all users.

In another alternate example, the HMS device would be used as a power source in a wireless power transmission system. Wireless power transmission (WPT) or wireless energy transmission (WET), or electromagnetic power transfer is the transmission of electrical energy without wires as a physical link. In a wireless power transmission system, a transmitter device, driven by electric power from a power source, generates a time-varying electromagnetic field, which transmits power across space to a receiver device, which extracts power from the field and supplies it to an electrical load. As a wireless transmission device, the HMS could provide wireless power to common electric and electronic devices enabled for wireless power reception. Examples could include mobile phones, tablets, sensors, CPAP machines or any other enabled device allowing increased mobility, convenience, and safety for users.

In another alternate example, the HMS device would include a carbon monoxide (CO) sensor to monitor for dangerous levels of carbon monoxide gas proximate to the device, enabling the device to provide local audible and visual notifications (alarms) as well as sending notifications via SMS of the alarm trigger. CO is a colorless, tasteless and odorless gas produced by incomplete combustion of carbon-containing materials. It is often referred to as the "silent killer" because it is virtually undetectable by humans. CO detectors are designed to measure CO levels over time and sound an alarm before dangerous levels of CO accumulate in an environment, giving people adequate warning to safely ventilate the area or evacuate. In the U.S. (as of January 2017) 32 states have enacted statutes regarding carbon monoxide detectors, and another 11 have promulgated regulations on CO detectors,[15] as well as in Washington, D.C. and New York City. Including a CO detector alarm in the HMS would add an additional level of safety in homes where CO detectors exist and provide a measure of safety in areas that do not have CO detectors such as homes, RV's, guest rooms, accessory dwelling units, and any other area without a CO alarm. In an alarm state the HMS would provide an onscreen notification of the alarm, a loud audible alarm signal, and (unlike standalone alarms) send an SMS or e-mail notification to any alternate caregiver if programmed into the unit thus providing a secondary level of safety for those living alone.

The HMS utilizes Bluetooth communication to interact with peripheral sensors and devices. These include but are not limited to Bluetooth enabled health meters, proximity sensors, motion sensors, temperature sensors and other devices utilizing Bluetooth technology. In an alternate example, the HMS device would communicate to other devices using Radio Frequency (RF) communication. RF communication can be accomplished utilizing a variety of frequencies and standards (i.e. Z-Wave, Zigbee, direct communication, etc.) allowing many current devices to interact within a home or control system. These devices include appliances, A/V equipment, temperature sensors, thermostats, water sensors, flow sensors, occupancy sensors, motion sensors, doorbells, pressure sensors, lighting control, security systems, smart phones, tablets and more. With RF interoperability comes the ability to interact with and monitor the home environment, thus giving insight into the activities of daily living, health, wellness and safety of users. The HMS would become a conduit of this information and couple it with its inherent functionalities such as medication adherence reporting and creating a much more powerful information set for caregivers about users. Further, RF communication between the HMS and health meters allows for use of RF meters for remote monitoring of health indicators such as weight, blood pressure, etc. to give real time insight into user health trends.

In other examples, the HMS would integrate an on-board temperature sensor to give the user insight to the temperature of the local environment as well as communicate that information remotely to designated caregivers. The temperature would be displayed on the user interface. The device would be configured to send automated SMS or email messages to designated contacts if the temperature registered above or below preconfigured setpoints. Including an onboard temperature sensor allows a user with poor vision a secondary way to know what the temperature is other than a thermostat which may be difficult to read (for those with poor eyesight) or inaccessible for those with limited mobility. Giving those outside the home insight to the temperature or "notifications" if the temperature is too high or too low provides a means of safety for the user and does so without the need for an internet connected thermostat.

In other examples, the HMS would use optical retina scanning for user identification and authentication. Authentication is important in cases where it is critical only the correct user has access to the HMS output. It can also be used to verify the identity of a caregiver to support federally mandated "Electronic Visit Verification." Like fingerprints, each person's retina is unique and, due to its unique and unchanging nature, the retina appears to be the most precise and reliable biometric identifier, aside from DNA. Retinal scanning also provides a viable option for users who lack the dexterity for PIN code or fingerprint authentication. Retinal scanning also mitigates some users' privacy concerns of facial recognition and is more reliable than face recognition. In addition to authentication, retinal scanning also has medical application. Communicable diseases such as AIDS, malaria, chicken pox (shingles), as well as hereditary diseases such as leukemia, lymphoma, and sickle cell anemia affect the eyes. Likewise, indications of chronic health conditions such as congestive heart failure, atherosclerosis, and cholesterol issues first appear in the eyes. Retinal scanning would provide a proactive layer of health insight to caregivers for users of the HMS.

In other examples, the Selective Non-Deliver (SND) feature will establish remote communication via electronic means with the HMS device's onboard date and time facilitator and the HMS device's cloud based scheduling software application to temporarily or permanently suspended the HMS device's onboard motorized package delivery system. Furthermore, the Selective Non-Deliver (SND) feature will electronically record Selective Non-Deliver (SND) events and generate an optional SMS or e-mail notification. Utilizing the Selective Non-Deliver (SND) feature will increase the accuracy of package delivery reporting, improve user convenience, and the HMS device's safety.

In another alternate example, a sequential roll of perforated packages are delivered via the onboard delivery and cutter mechanism on predetermined dates and times dictated by the HMS device's cloud based scheduling software application. The Missed Package Feature (MPF) retrieves, collects, and stores packages within the sequential perforated package roll that are delivered outside the predetermined date and time parameters dictated by the device's cloud based scheduling software application. Furthermore, the Missed Package Feature (MPF) will electronically record packages retrieved outside the predetermined date and time parameters, provide an onscreen notification, and generate an optional SMS or e-mail notice. Missed Package Feature (MPF) will increase the accuracy of package delivery reporting and synchronize the date and time of the sequential perforated package roll with the HMS device's cloud-based scheduling software application. The Missed Package Feature (MPF) will also improve the safety of the HMS devices for all users.

In another alternate example, the Voice Activation and Response Interface (VAARI) acts as an alternate HMS device's activation method using audio-based input and interaction commands. With assistance from the device's artificial intelligence, the audio-based user interface facilitates device control by accurately processing and carrying out a user's command as per the user's preference. The Voice Activation and Response Interface (VAARI) receives audio-based input commands, converts them in onscreen or spoken voice acknowledgements and executes commands. The speech recognition voice component of Voice Activation and Response Interface (VAARI) processes multiple simultaneous commands and interprets multiple spoken accents and dialects. Voice Activation and Response Interface (VAARI) events will be electronically recorded and HMS device's reporting. Utilizing the Voice Activation and Response Interface (VAARI) will provide users with an alternative activation method and improve user convenience.

In another example the HMS device's electronically records events and transmits event history, that is maintained by the provider of care over time and may include key administrative clinical data relevant to the user. The Electronic Health Record Integration (EHRI) feature supports visibility into care-related activities directly or indirectly through various interfaces, including evidence-based decision support, quality management, and outcomes. The Electronic Health Record Integration (EHRI) feature may provide information including but not limited to demographics, progress notes, problems, medications, vital signs, past medical history, immunizations, and laboratory data. The Electronic Health Record Integration (EHRI) feature automates access to information, reduces errors, improves accuracy and streamlines the care team's workflow.

In another example, we disclose automatic identification tag attached to users that consists of a tiny radio transponder, a radio receiver and transmitter. When triggered by an electromagnetic interrogation pulse from a nearby RFID reader device, the tag transmits digital data identifying the user with a unique number. This number will authenticate the users of the HMS device's Radio-Frequency Identification (RFID) tags can be either passive, active, or battery-assisted passive. An active tag has an on-board battery and periodically transmits its ID signal. A battery-assisted passive tag has a small battery on board and is activated when in the presence of an RFID reader. The RFID security device shall be used where the device uses a unique marker of the individual for security.

In another example, an Electronic Visit Verification feature may be implemented. This would enable providers to verify a caretaker is performing as expected in their duties to a patient. The Electronic Visit Verification (EVV) feature uses a familiar, off the shelf, platform to capture home care hours, duties and travel electronically. Information is securely delivered as often as needed, to any number of administrative agency health record or care management software platforms processing or the online web application. The service eliminates the need to train home care workers on new technologies, satisfies the initial electronic time capture requirements and seamlessly integrates into existing or new agency business systems. The service is extremely affordable and can be set up within any time capture system requirements. When new attendance or payroll solutions are introduced, this service will easily deliver data to the agency's new platforms without disrupting the point of care environment or the home care agency's business process.

TELEHEALTH is generally the distribution of health-related services and information via electronic information and telecommunication technologies. It allows long-distance patient and clinician contact, care, advice, reminders, education, intervention, monitoring, and remote admissions. Telemedicine is sometimes incorrectly used as a synonym or is used in a more limited sense to describe remote clinical services, such as diagnosis and monitoring. When rural settings, lack of transport, a lack of mobility, decreased funding, or a lack of staff restrict access to care, telehealth may bridge the gap.

As well as provider distance-learning; meetings, supervision, and presentations between practitioners; online information and health data management and healthcare system integration. Telehealth could include two clinicians discussing a case over video conference; a robotic surgery occurring through remote access; physical therapy done via digital monitoring instruments, live feed and application combinations; tests being forwarded between facilities for interpretation by a higher specialist; home monitoring through continuous sending of patient health data; client to practitioner online conference; or even videophone interpretation during a consult.

The Health Resources Services Administration defines telehealth as the use of electronic information and telecommunications technologies to support long-distance clinical health care, patient and professional health-related education, public health and health administration. Technologies include videoconferencing, the internet, store-and-forward imaging, streaming media, and terrestrial and wireless communications.

Telehealth is different from telemedicine because it refers to a broader scope of remote healthcare services than telemedicine. While telemedicine refers specifically to remote clinical services, telehealth can refer to remote non-clinical services, such as provider training, administrative meetings, and continuing medical education, in addition to clinical services.

There are several other ways to define telehealth one in terms of Information and communication technologies. ICT's have great potential to address some of the challenges faced by both developed and developing countries in providing accessible, cost effective, high-quality health care services. Telemedicine uses ICTs to overcome geographical barriers and increase access to health care services. This is particularly beneficial for rural and underserved communities in developing countries—groups that traditionally suffer from lack of access to health care. In light of this potential, the World Health Organization (WHO) established the Global Observatory for eHealth (GOe) to review the benefits that ICTs can bring to health care and patients' wellbeing.

The Observatory is charged with determining the status of eHealth solutions, including telemedicine, at the national, regional, and global level, and providing WHO's Member States with reliable information and guidance on best practices, policies, and standards in eHealth. In 2005, following the formation of WHO's eHealth strategy, the Observatory conducted a global eHealth survey to obtain general information about the state of eHealth among Member States. Based on the data from that survey, the GOe carried out a second global survey in 2009; it was designed to explore eight thematic areas in detail, the results of each being reported and analyzed in individual publications—the Global Observatory for eHealth series. The eHealth series is primarily meant for government ministries of health, information technology, and telecommunications, as well as others working in eHealth—academics, researchers, eHealth professionals, nongovernmental organizations, and donors.

Medication adherence represents a significant challenge to the efficacy and cost-effectiveness of health care. Problems with medication adherence are well documented in many common conditions, including hypertension, chronic obstructive pulmonary disease, depression, and diabetes. Existing literature suggests that typical rates of adherence are often as low as 50% significantly impacting the delivery of care as it was originally prescribed. Recognition of this fact has led many authors including the World Health Organization to argue that in coming years, increasing the effectiveness of adherence interventions may have a greater impact on long term health than improvements in specific medical treatments.

WIRELESS COMMUNICATIONS otherwise known as "over the air" is the transfer of information or power between two or more points that are not connected by an electrical conductor. The most common wireless technologies use radio waves. With radio waves, intended distances can be short, such as a few meters for Bluetooth or as far as millions of kilometers for deep-space radio communications. It encompasses various types of fixed, mobile, and portable applications, including two-way radios, cellular telephones, personal digital assistants (PDAs), and wireless networking. Other examples of applications of radio wireless technology include GPS units, garage door openers, wireless computer mouse, keyboards and headsets, headphones, radio receivers, satellite television, broadcast television and cordless telephones. Somewhat less common methods of achieving wireless communications include the use of other electromagnetic wireless technologies, such as light, magnetic, or electric fields or the use of sound.

The term wireless has been used twice in communications history, with slightly different meaning. It was initially used from about 1890 for the first radio transmitting and receiving technology, as in wireless telegraphy, until the new word radio replaced it around 1920. The term was revived in the 1980s and 1990s mainly to distinguish digital devices that communicate without wires, such as the examples listed in the previous paragraph, from those that require wires or cables. This became its primary usage in the 2000s, due to the advent of technologies such as mobile broadband, Wi-Fi and Bluetooth.

Wireless operations permit services, such as mobile and interplanetary communications, that are impossible or impractical to implement with the use of wires. The term is commonly used in the telecommunications industry to refer to telecommunications systems (e.g. radio transmitters and receivers, remote controls, etc.) which use some form of energy (e.g. radio waves, acoustic energy,) to transfer information without the use of wires. Information is transferred in this manner over both short and long distances. In non-limiting terms, we include but are not limited to one or more of the following wireless technologies for the transfer of data and information between devices, the internet, servers and clients running application or serving data to the pre-packaged tablet delivery system; these include a Subscriber Identity Module or SIM Card; Bluetooth; and WIFI and others as identified below:

SIM CARD is an example of wireless connectivity to the internet, we disclose a Subscriber Identity Module (SIM) card or SIM. The SIM contains its unique serial number (ICCID), international mobile subscriber identity (IMSI) number, security authentication and ciphering information, temporary information related to the local network, a list of the services the user has access to, and two passwords: a personal identification number (PIN) for ordinary use, and a personal unblocking code (PUC) for PIN unlocking. Identity is verified by the SIM card using the IMSI. The IMSI, is retrieved from the SIM card and sent to the preferred network. The network looks up the IMSI and its associated authentication key. The network then generates a random number. In one instance the random number is signed with the authentication key on file with the network. In a second instance, the randomly generated number is sent to the SIM where the SIM signs it with its authentication key and sends it back to the network. The signed network number and signed SIM card number are then compared. If the two values match the SIM card is validated and access to the network is granted.

BLUETOOTH is a wireless technology standard used for exchanging data between fixed and mobile devices over short distances using short-wavelength UHF radio waves in the industrial, scientific and medical radio bands, from 2.400 to 2.485 GHz, and building personal area networks (PANs). It was originally conceived as a wireless alternative to RS-232 data cables. Bluetooth is managed by the Bluetooth Special Interest Group (SIG), which has more than 35,000 member companies in the areas of telecommunication, computing, networking, and consumer electronics.

The IEEE standardized Bluetooth as IEEE 802.15.1, but no longer maintains the standard. The Bluetooth SIG oversees development of the specification, manages the qualification program, and protects the trademarks; as such a network of patents apply to the technology, which are licensed to individual qualifying devices.

WIFI is a family of wireless networking technologies, based on the IEEE 802.11 family of standards, which are commonly used for local area networking of devices and Internet access. Wi-Fi is a trademark of the non-profit Wi-Fi Alliance, which restricts the use of the term Wi-Fi Certified to products that successfully complete interoperability certification testing. As of 2010, the Wi-Fi Alliance consisted of more than 375 companies from around the world. [5] As of 2009, Wi-Fi-integrated circuit chips shipped approximately 580 million units yearly.[6] Devices that can use Wi-Fi technologies include desktops and laptops, smartphones and tablets, smart TVs, printers, digital audio players, digital cameras, cars and drones.

Wi-Fi uses multiple parts of the IEEE 802 protocol family and is designed to interwork seamlessly with its wired sibling Ethernet. Compatible devices can network through wireless access points to each other as well as to wired devices and the Internet. The different versions of Wi-Fi are specified by various IEEE 802.11 protocol standards, with the different radio technologies determining radio bands, and the maximum ranges, and speeds that may be achieved. Wi-Fi most commonly uses the 2.4 gigahertz (120 mm) UHF and 5 gigahertz (60 mm) SHF ISM radio bands; these bands are subdivided into multiple channels. Channels can be shared between networks but only one transmitter can locally transmit on a channel at any moment in time.

WiMAX (Worldwide Interoperability for Microwave Access) is a family of wireless broadband communication standards based on the IEEE 802.16 set of standards, which provide multiple physical layer (PHY) and Media Access Control (MAC) options. The forum describes WiMAX as "a standards-based technology enabling the delivery of last mile wireless broadband access as an alternative to cable and DSL". IEEE 802.16m or WirelessMAN-Advanced was a candidate for the 4G, in competition with the LTE Advanced standard. WiMAX was initially designed to provide 30 to 40 megabit-per-second data rates, with the 2011 update providing up to 1 Gbit/s for fixed stations. The latest version of WiMAX, WiMAX release 2.1, popularly branded as/known as WiMAX 2+, is a smooth, backwards-compatible transition from previous WiMAX generations. It is compatible and inter-operable with TD-LTE.

5G is the fifth-generation wireless technology for digital cellular networks that began wide deployment in 2019. As with previous standards, the covered areas are divided into regions called "cells", serviced by individual antennas. Virtually every major telecommunication service provider in the developed world is deploying antennas or intends to deploy them soon. The frequency spectrum of 5G is divided into millimeter waves, mid-band and low band. Low band uses a similar frequency range as the predecessor, 4G.

G millimeter wave is the fastest, with actual speeds often being 1-2 Gb/s down. Frequencies are above 24 GHz reaching up to 72 GHz which is above the extremely high frequency band's lower boundary. The reach is short, so more cells are required. Millimeter waves have difficulty traversing many walls and windows, so indoor coverage is limited.

5G mid-band is the most widely deployed, in over 20 networks. Speeds in a 100 MHz wide band are usually 100-400 Mb/s down. In the lab and occasionally in the field, speeds can go over a gigabit per second. Frequencies deployed are from 2.4 GHz to 4.2 GHz. Sprint and China Mobile are using 2.5 GHz, while others are mostly between 3.3 and 4.2 GHz, a range which offers increased reach. Many areas can be covered simply by upgrading existing towers, which lowers the cost.

FINGERPRINT READERS are a method for capturing a fingerprint using a sensor that consists of rolling or touching with the finger onto a sensing area, which according to the physical principle in use (optical, ultrasonic, capacitive, or thermal) captures the difference between valleys and ridges. When a finger touches or rolls onto a surface, the elastic skin deforms. The quantity and direction of the pressure applied by the user, the skin conditions and the projection of an irregular 3D object (the finger) onto a 2D flat plane introduce distortions, noise, and inconsistencies in the captured fingerprint image. These problems result in inconsistent and non-uniform irregularities in the image.

During each acquisition, therefore, the results of the imaging are different and uncontrollable. The representation of the same fingerprint changes every time the finger is placed on the sensor plate, increasing the complexity of any attempt to match fingerprints, impairing the system performance and consequently, limiting the widespread use of this biometric technology.

In order to overcome these problems, as of 2010, non-contact or touchless 3D fingerprint scanners have been developed. Acquiring detailed 3D information, 3D fingerprint scanners take a digital approach to the analog process of pressing or rolling the finger. By modelling the distance between neighboring points, the fingerprint can be imaged at a resolution high enough to record all the necessary detail.

WEBCAM is a video camera that feeds or streams an image or video in real time to or through a computer to a computer network, such as the Internet. Web cams can be used during a video chat session involving two or more people, with conversations that include live audio and video.

SMOKE DETECTORS work using one or both of the following methods. Ionization-type smoke alarms have a small amount of radioactive material between two electrically charged plates, which ionizes the air and causes current to flow between the plates. When smoke enters the chamber, it disrupts the flow of ions, thus reducing the flow of current and activating the alarm.

Photoelectric-type alarms aim a light source into a sensing chamber at an angle away from the sensor. As smoke enters the chamber and crosses the path of the light beam, light is scattered by the smoke particles, aiming it toward the sensor, which in turn triggers the alarm. It is recommended that both technologies be used in combination within an alarm for additional accuracy of detection.

MOTION DETECTION is based on non-contact sensors incorporating optical, microwave, or acoustic sensor technology; in many cases a transmitter/receiver pair. However, the detector may consist of a single or passive sensor, one that senses a signature only from the moving object via emission or reflection, i.e., it can be emitted by the object, or by some ambient emitter such as the sun or a radio station of sufficient strength. Changes in the optical, microwave or acoustic field in the device's proximity are interpreted by the electronics based on technology such as infrared sensors, radar sensors, or video camera software.

BARCODE SCANNERS are optical scanners that can read printed barcodes, decode the data contained in the barcode and send the data to a computer. The barcode is a machine-readable optical label that contains information about the item to which it is attached. It consists of a light source, a lens and a light sensor translating for optical impulses into electrical signals. Additionally, nearly all barcode readers contain decoder circuitry that can analyze the barcode's image data provided by the sensor and sending the barcode's content to the scanner's output port.

DISPLAY DEVICE is an output device for presentation of information in visual or tactile form (the latter used for example in tactile electronic displays for blind people). When the input information that is supplied has an electrical signal the display is called an electronic display. Today these displays generally comprise 2 technologies, these are:

LIQUID-CRYSTAL DISPLAY (LCD) is a flat-panel display or other electronically modulated optical device that uses the light-modulating properties of liquid crystals combined with polarizers. Liquid crystals do not emit light directly, instead using a backlight or reflector to produce images in color or monochrome.

The backlight in liquid crystal display provides an even light source behind the screen. This light is polarized, meaning only half of the light shines through to the liquid crystal layer. The liquid crystals are made up of a part solid, part liquid substance that can be "twisted" by applying electrical voltage to them. They block the polarized light when they are off, but reflect red, green, or blue light when activated. Each LCD screen contains a matrix of pixels that display the image on the screen;

LED display is a flat panel display that uses an array of light-emitting diodes as pixels for a video display. Their brightness allows them to be used outdoors where they are visible in the sun for store signs and billboards; and Other display types include but not limited to Electroluminescent (ELD) displays; Thin-film transistor (TFT) displays; OLED displays; AMOLED displays; Plasma (PDP) displays; and Quantum dot (QLED) displays.

TOUCH SCREEN is a computer display screen that is also an input device. The screens are sensitive to pressure; a user interacts with the computer by touching pictures or words on the screen. This interaction allows for the elimination of additional accessories, such as a trackpad, buttons or a mouse, when navigating an interface, or program.

A resistive touch screen panel is coated with a thin metallic electrically conductive and resistive layer that causes a change in the electrical current which is registered as a touch event and sent to the controller for processing. Resistive touch screen panels are generally more affordable but offer only 75% clarity and the layer can be damaged by sharp objects. Resistive touch screen panels are not affected by outside elements such as dust or water.

A capacitive touch screen panel is coated with a material that stores electrical charges. When the panel is touched, a small amount of charge is drawn to the point of contact. Circuits located at each corner of the panel measure the charge and send the information to the controller for processing. Capacitive touch screen panels must be touched with a finger unlike resistive and surface wave panels that can use fingers and stylus. Capacitive touch screens are not affected by outside elements and have high clarity.

INFRARED THERMOGRAPHY (IRT), thermal imaging, and thermal video are examples of infrared imaging science. Thermographic cameras usually detect radiation in the long-infrared range of the electromagnetic spectrum (roughly 9,000-14,000 nanometers or 9-14 µm) and produce images of that radiation, called thermograms. Since infrared radiation is emitted by all objects with a temperature above absolute zero according to the black body radiation law, thermography makes it possible to see one's environment with or without visible illumination. The amount of radiation emitted by an object increases with temperature; therefore, thermography allows one to see variations in temperature. When viewed through a thermal imaging camera, warm objects stand out well against cooler backgrounds; humans and other warm-blooded animals become easily visible against the environment, day or night. As a result, thermography is particularly useful to the military and other users of surveillance cameras.

Some physiological changes in human beings and other warm-blooded animals can also be monitored with thermal imaging during clinical diagnostics. Thermography is used in allergy detection and veterinary medicine. Some alternative medicine practitioners promote its use for breast screening, despite the FDA warning that "those who opt for this method instead of mammography may miss the chance to detect cancer at its earliest stage". Government and airport personnel used thermography to detect suspected swine flu cases during the 2009 pandemic.

PULSE OXIMETRY is a noninvasive method for monitoring a person's oxygen saturation by, in its most common (transmissive) application mode, a sensor device is placed on a thin part of the patient's body, usually a fingertip or earlobe, or in the case of an infant, across a foot. The device passes two wavelengths of light through the body part to a photodetector. It measures the changing absorbance at each of the wavelengths, allowing it to determine the absorbances due to the pulsing blood alone.

ELECTROCARDIOGRAM (EKG) is a test which measures the electrical activity of your heart to show whether it is working normally. An EKG records the heart's rhythm and activity on a moving strip of paper or a line on a screen.

HEALTH INSURANCE PORTABILITY AND ACCOUNTABILITY ACT (HIPAA) is a series of regulatory standards that outline the lawful use and disclosure of protected health information (PHI). PHI transmitted, stored, or accessed electronically also falls under HIPAA regulatory standards and is known as electronic protected health information, or ePHI. HIPAA compliance is regulated by the Department of Health and Human Services (HHS) and enforced by the Office for Civil Rights (OCR).

HIPAA regulation outlines a set of national standards that all covered entities and business associates must address. These standards require covered entities and business associates to conduct annual audits of their organization to assess Administrative, Technical, and Physical gaps in compliance with HIPAA Privacy and Security standards. Under HIPAA, a Security Risk Assessment is NOT ENOUGH to be compliant—it's only one essential audit that HIPAA-beholden entities are required to perform in order to maintain their compliance year-over-year. Once covered entities and business associates have identified their gaps in compliance through these self-audits, they must implement remediation plans to reverse compliance violations. These remediation plans must be fully documented and include calendar dates by which gaps will be remedied.

Covered entities and business associates must develop Policies and Procedures corresponding to HIPAA regulatory standards as outlined by the HIPAA Rules. These policies and procedures must be regularly updated to account for changes to the organization. Annual staff training on these Policies and Procedures is required, along with documented employee attestation stating that staff has read and understood each of the organization's policies and procedures.

HIPAA-beholden organizations must document ALL efforts they take to become HIPAA compliant. This documentation is critical during a HIPAA investigation with HHS OCR to pass strict HIPAA audits.

HIPAA Compliant Software Security requirements comprise specific provisions for administrative safeguards, physical safeguards, and access control. The administrative requirements include Access authorization, Log in monitoring, Password management, Data backup plan, Disaster recovery plan, and Emergency mode operation plan.

Physical safeguards include a facility security plan, and Data backup and storage. Access control regulations include unique user identification, automatic logoff, and encryption and decryption.

MOBILE DASHBOARD provides a portable means of monitoring the most important, high-level key performance indicators (KPIs) and data related to all areas of a business or organization. It offers ease of access through mobile devices, on the go, with critical metrics displayed at-a-glance.

Mobile devices and dashboards are quickly becoming pivotal in performance monitoring, combining ease of use with real-time dashboard reporting that offers users unlimited access to invaluable business-centric information at any time or location.

VIRTUAL ASSISTANT, as an example Amazon Alexa, also known simply as Alexa, is a VIRTUAL ASSISTANT AI developed by Amazon, first used in the Amazon Echo and the Amazon Echo Dot smart speakers developed by Amazon Lab126. It is capable of voice interaction, music playback, making to-do lists, setting alarms, streaming podcasts, playing audiobooks, and providing weather, traffic, sports, and other real-time information, such as news. Alexa can also control several smart devices using itself as a home automation system. Users can extend the Alexa capabilities by installing "skills" (additional functionality developed by third-party vendors, in other settings more commonly called apps such as weather programs and audio features).

PERS—(Personal Emergency Reporting System) A communications system that notifies a central monitoring facility in case of problems. A PERS is activated by the elderly or physically impaired either from a transmitter worn on the wrist or around the neck. Some systems use infrared transmitters and receivers to monitor a person's daily activities and ensure that they are mobile during certain hours of the day.

EVV—Electronic visit verification is a method used to verify home healthcare visits to ensure patients are not neglected and to cut down on fraudulently documented home visits.

PRN Medicines that are taken "as needed" are known as "PRN" medicines. "PRN" is a Latin term that stands for "pro re nata," which means "as the thing is needed." It's important to know the difference between daily and "as needed" medicines.

PID CONTROLLER—A proportional-integral-derivative controller (PID controller or three-term controller) is a control loop mechanism employing feedback that is widely used in industrial control systems and a variety of other applications requiring continuously modulated control. A PID controller continuously calculates an error value {\displaystyle e(t)} as the difference between a desired setpoint (SP) and a measured process variable (PV) and applies a correction based on proportional, integral, and derivative terms (denoted P, I, and D respectively), hence the name. In practical terms it automatically applies accurate and responsive correction to a control function. An everyday example is the cruise control on a car, where ascending a hill would lower speed if only constant engine power were applied. The controller's PID algorithm restores the measured speed to the desired speed with minimal delay and overshoot by increasing the power output of the engine.

SMART HOME SENSORS or to define it in a broader sense, home automation refers to home attributes such as lighting, climate, entertainment systems, appliances, access control to the home, and alarm systems. A home automation system typically connects controlled devices to a central hub or "gateway". The user interface for control of the system uses either wall-mounted terminals, tablet or desktop computers, a mobile phone application, or a Web interface that may also be accessible off-site through the Internet.

WIRELESS POWER RECEPTION is a type of wireless power transfer. It uses electromagnetic induction to provide electricity to portable devices. Energy is transferred through inductive coupling. An alternating current is run through an induction coil in the charging station or pad (the primary or transmission coil). Any moving electric charge creates a magnetic field, as stated by Oersted's law. The magnetic field fluctuates in strength as the AC current is continually changing amplitude. A changing magnetic field generates an electromotive force otherwise known as Faraday's law of induction. This makes an alternating electric current in a second induction coil (the receiving, or secondary coil) in the portable device. It is then converted to direct current with a rectifier and used to charge a battery or provide operating power. Greater distances between sender and receiver coils can be achieved when the inductive charging system uses resonant inductive coupling. Resonant inductive coupling is a phenomenon with inductive coupling where the coupling becomes stronger when the secondary (load bearing) side of the loosely coupled coil resonates.

WIRELESS POWER TRANSMISSION (WPT) or WIRELESS ENERGY TRANSMISSION (WET), or ELECTROMAGNETIC POWER TRANSFER is the transmission of electrical energy without wires as a physical link. In a wireless power transmission system, a transmitter device, driven by electric power from a power source, generates a time-varying electromagnetic field, which transmits power across space to a receiver device, which extracts power from the field and supplies it to an electrical load.

PASSIVE ACOUSTICS is the action of listening for sounds, often at specific frequencies or for purposes of specific analyses.

SOUND EVENT DETECTION aims at processing the continuous acoustic signal and converting it into such symbolic descriptions of the corresponding sound events present at the auditory scene. Automatic sound event detection can be utilized in a variety of applications, including context-based indexing and retrieval in multimedia databases, unobtrusive monitoring in health care, surveillance, and military applications. The symbolic information about the sound events can be used in other research areas, e.g., audio context recognition, automatic tagging, and audio segmentation.

SELF-HEALING CUTTING MAT is a mat with an elastic surface and is made up of individual small pieces of material that are tightly pressed together to form the solid surface. A blade will simply pass in between these small pieces and will separate the pieces instead of cutting through them. Whenever a cut is made, the surface's memory retaining properties close it back.

CARBON MONOXIDE DETECTORS are designed to measure CO levels over time and sound an alarm before dangerous levels of CO accumulate in an environment, giving people adequate warning to safely ventilate the area or evacuate. Different carbon monoxide detectors set off different types of alerts. In a biomimetic sensor a gel changes color when it absorbs carbon monoxide, and this color change triggers the alarm. In a metal oxide semiconductor when the silica chip's circuitry detects carbon monoxide, it lowers the electrical resistance, and this change triggers the alarm. In an electrochemical sensor, electrodes in a chemical solution sense changes in electrical currents when they come into contact with carbon monoxide, and this change triggers the alarm.

RF COMMUNICATIONS refers to a wireless electromagnetic signal used as a form of communication. Radio waves are a form of electromagnetic radiation with identified radio frequencies that range from 3 kHz to 300 GHz. Frequency refers to the rate of oscillation (of the radio waves.) RF propagation occurs at the speed of light and does not need a medium like air to travel.

TEMPERATURE SENSORS are for everyday use in buildings, water regulation and refrigeration, for example, and are also vital in many other applications such as consumer, medical, and industrial electronics. There are four types of temperature sensors that are most used in modern-day electronics: thermocouples, RTDs (resistance temperature detectors), thermistors, and semiconductor based integrated circuits (IC). Thermocouples are the most used type of temperature sensor. They are used in industrial, automotive, and consumer applications. Thermocouples are self-powered, require no excitation, can operate over a wide temperature range, and have quick response times. Thermocouples are made by joining two dissimilar metal wires together. This causes a Seebeck Effect. The Seebeck Effect is a phenomenon in which a temperature difference of two dissimilar conductors produces a voltage difference between the two substances. It is this voltage difference that can be measured and used to calculate the temperature. An RTD is a resistor with well-defined resistance vs. temperature characteristics. As temperature changes, the resistance of any metal changes as well. This difference in resistance is what RTD temperature sensors are based on. RTD elements usually have higher thermal mass, and therefore respond slower to changes in temperature than thermocouples. They also require an excitation current to flow through the RTD. If this current is known, the resistance can be calculated. Thermistors are like RTDs in that temperature changes cause measurable resistance changes. Thermistors are usually made from a polymer or ceramic material. In most cases, thermistors are cheaper but are also less accurate than RTDs. The NTC (Negative Temperature Coefficient) thermistor is the most used thermistor for temperature measurement application. An NTC thermistor's resistance decreases as the temperature increases. A common approach of using a thermistor, is where a thermistor and a fixed value resistor form a voltage divider with an output that is digitized by an ADC. Semiconductor based temperature sensor ICs come in two different types: local temperature sensor and remote digital temperature sensor. Local temperature sensors are ICs that measure their own die temperature by using the physical properties of a transistor. Remote digital temperature sensors measure the temperature of an external transistor. Local temperature sensors can use either analog or digital outputs. Analog outputs can be either voltage or current while digital outputs can be seen in several formats such as I2C, SMBus, 1-Wire®, and Serial Peripheral Interface (SPI). Remote digital temperature sensors work like local temperature sensors by using the physical properties of a transistor. The difference is the transistor is located away from the sensor chip.

A RETINAL SCAN is performed by casting an unperceived beam of low-energy infrared light into a person's eye as they look through the scanner's eyepiece. This beam of light traces a standardized path on the retina. Because retinal blood vessels absorb light more readily than the surrounding tissue, the amount of reflection varies during the scan. The patter of variations is digitized and stored.

VOICE ACTIVATION AND RESPONSE INTERFACE (VAARI) makes spoken human interaction with computers possible, using speech recognition to understand spoken commands and answer questions, and typically text to speech to play a reply.

SPEECH RECOGNITION enables the recognition and translation of spoken language into text by computers. Modern general-purpose speech recognition systems are based on Hidden Markov Models. These are statistical models that output a sequence of symbols or quantities. HMIs are used in speech recognition because a speech signal can be viewed as a piecewise stationary signal or a short-time stationary signal. In a short time-scale, speech can be approximated as a stationary process. In speech recognition, the hidden Markov model would output a sequence of n-dimensional real-valued vectors, outputting one every 10 milliseconds. The vectors would consist of cepstral coefficients, which are obtained by taking a Fourier transform of a short time window of speech and decorrelating the spectrum using a cosine transform, then taking the first coefficients. The hidden Markov model will tend to have in each state a statistical distribution that is a mixture of diagonal covariance Gaussians, which will give a likelihood for each observed vector. Each word, or each phoneme, will have a different output distribution; a hidden Markov model for a sequence of words or phonemes is made by concatenating the individual trained hidden Markov models for the separate words and phonemes.

ELECTRONIC HEALTH RECORD INTEGRATION allows a system to go beyond standard clinical data collection in a provider's office and can be inclusive of a broader view of a patient's care. An electronic health record (EHR) is a digital version of a patient's paper chart. EHRs are real-time, patient-centered records that make information available instantly and securely to authorized users. EHRs are a vital part of health IT and can: contain a patient's medical history, diagnoses, medications, treatment plans, immunization dates, allergies, radiology images, and laboratory and test results, allow access to evidence-based tools that providers can use to make decisions about a patient's care, and automate and streamline provider workflow. One of the key features of an EHR is that health information can be created and managed by authorized providers in a digital format capable of being shared with other providers across more than one health care organization. EHRs are built to share information with other health care providers and organizations—such as laboratories, specialists, medical imaging facilities, pharmacies, emergency facilities, and school and workplace clinics—so they contain information from all clinicians involved in a patient's care.

RADIO-FREQUENCY IDENTIFICATION systems consist of a tiny radio transponder, a radio receiver and transmitter. When triggered by an electromagnetic interrogation pulse from a nearby RFID reader device, the tag transmits digital data back to the reader. RFID tags can be passive, active, or battery-assisted passive. A passive tag is powered by energy from the RFID reader's interrogating radio waves. An active tag has an on-board battery and periodically transmits its ID signal. A battery-assisted passive tag has a small battery on board and is activated when in the presence of an RFD reader.

PRE-PACKAGED TABLET describes a medication which has been taken out of its original container, and re-packaged in a production unit, labelled with pre-printed instructions which require minimal completion for discharge.

STRIP PACKAGING is an alternative form of unit dose packaging in which a pharmaceutical product is enclosed between two webs of heat-sealable flexible film sent through a heated reciprocating platen and a heated crimp roller.

NON-TRANSITORY COMPUTER READABLE MEDIUM are those terms that represent the various operations of methods described below and may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general-purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of two computing components, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Thus, in some aspects, a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Processes or steps described in one implementation can be suitably combined with steps of other described implementations.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device.

It is to be understood that the claims are not limited to the precise configuration and components illustrated above. Various modifications, changes and variations may be made in the arrangement, operation and details of the methods and apparatus described above without departing from the scope of the claims.

For the sake of convenience, the operations are described as various interconnected functional blocks or distinct software modules. This is not necessary, however, and there may be cases where these functional blocks or modules are equivalently aggregated into a single logic device, program, or operation with unclear boundaries. In any event, the functional blocks and software modules or described features can be implemented by themselves, or in combination with other operations in either hardware or software.

Having described and illustrated the principles of the systems, methods, processes, and/or apparatuses disclosed herein in a preferred example thereof, it should be apparent that the systems, methods, processes, and/or apparatuses may be modified in arrangement and detail without departing from such principles. Claim is made to all modifications and variation coming within the spirit and scope of the following claims.

To reduce the complexity and length of the Detailed Specification, Applicant(s) herein expressly incorporate(s) by reference all of the following materials identified in each paragraph below. The incorporated materials are not necessarily "prior art" and Applicant(s) expressly reserve(s) the right to swear behind any of the incorporated materials. A more complete understanding may be derived by referring to the description when considered in connection with the following Attachments. If the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

The invention claimed is:

1. An integrated health management system, comprising:
a processor connected to a communications system and a memory wherein the memory stores a database, wherein the database is configured as a distributed database, wherein the distributed database is distributed across at least one of different physical locations, one or more processors located proximate to the processor, and a local network of interconnected processors, the processor coupled to a patient data pipeline, the patient data pipeline performing at least one of a stream processing and a data transformation process;
a provisioning layer coupled to the patient data pipeline, the provisioning layer assisting in system management;
an application server comprising at least one sensor and one application operating in combination for generation of first data;
a first healthcare system database within the patient data pipeline, the first healthcare system database to store the first data;
a second healthcare system database within the patient data pipeline, the second healthcare system database to transform and store the first data as transformed data;
an actions module coupled to the patient data pipeline comprising:
a machine learning module, the machine learning module to receive the transformed data and user intervention data as an input and to output predictions associated with healthcare outcomes;
a tablet delivery apparatus configured to dispense medication based at least in part on the predictions associated with the healthcare outcomes to a user, wherein the delivery apparatus includes:
an input alignment guide to adjust pre-packaged tablets into the delivery apparatus,
a processor modulated differential drive for directional control of the pre-packaged tablets, wherein the differential drive comprises a dual motor drive system with independent actuators;
a sensor for sensing a location and an orientation of the pre-packaged tablet during a delivery wherein the sensed location and orientation of the pre-packaged tablet is used to modulate the differential drive based on at least one of a predetermined configuration within the processor and a dynamic configuration responsive to the sensed location and orientation;
a cutter mechanism and a cutter mechanism control logic wherein the cutter mechanism control logic is configured to:
monitor the sensed pre-packaged tablet location and orientation,
initiate a cutting sequence responsive to at least one of the predetermined configuration within the processor and the dynamic configuration responsive to determining an optimal sensed location and orientation;
generate and log a message into the distributed database responsive to the cutting sequence;
a sensor data collection system, wherein the collected sensor data is responsive to the user and stored in the distributed database; and
a personal emergency reporting system to:
determine a change in healthcare outcomes based at least in part on the predictions associated with the healthcare outcomes; and
responsive to determining the change, generate a user intervention message to at least one of a patient, a caretaker, or a healthcare professional and request new biometric data.

2. The integrated health management system of claim 1, wherein the patient data pipeline is distributed across one or more physical locations.

3. The integrated health management system of claim 1, wherein the first healthcare system database is a warm path store or a cloud service.

4. The integrated health management system of claim 1, wherein the first data collected by the first healthcare system database is at least one of the biometric data and user intervention data.

5. The integrated health management system of claim 1, further comprising a patient authentication system to authenticate a patient based at least in part on one or more of the biometric data or a personal identification number (PIN).

6. The integrated health management system of claim 5, wherein the patient healthcare system prevents the integrated health management from performing operations until the patient is authenticated.

7. The integrated health management system of claim 1, further comprising a patient authentication system to authenticate a user based at least in part on at least one of a retinal scan or a fingerprint scan.

8. The integrated health management system of claim 1, wherein the machine learning module is trained based at least in part on communication with one or more data sets within the patient data pipeline.

9. The integrated health management system of claim 1, wherein the biometric data includes at least one of heart rate data, blood pressure data, temperature data, blood oxygen level data, and weight data.

10. The integrated health management system of claim 1, wherein the delivery apparatus system comprises a cutter mechanism and a cutter control system.

11. The integrated health management system of claim 1, wherein the tablet delivery apparatus system is configured to withhold pre-packaged tablets based at least in part on the change in the healthcare outcomes.

12. The integrated health management system of claim 1, wherein the tablet delivery apparatus system is configured to deliver prepackaged medication based at least in part on the change in the healthcare outcomes.

13. A method for managing patient healthcare comprising:
receiving from an application server comprising at least one sensor and one application operating in combination with the sensor, first data;
configuring a processor to operate a provisioning layer, the provisioning layer coupled to a patient data pipeline, the patient data pipeline comprising a first healthcare system database, the first healthcare system database to store the first data, wherein the patient data pipeline is configured for stream processing and data transformation;
configuring a second healthcare system database associated with the patient data pipeline to generate transformed data based at least in part on the first data;
configuring a machine learning module associated with the patient data pipeline to process the transformed data and user intervention data to generate one or more predictions associated with one or more healthcare outcomes;
causing a tablet delivery apparatus to dispense medication based at least in part on the predictions associated with the one or more healthcare outcomes to a user, wherein the delivery apparatus includes:
an input alignment guide to adjust pre-packaged tablets into the delivery apparatus,
a processor modulated differential drive for directional control of the pre-packaged tablets, wherein the differential drive comprises a dual motor drive system with independent actuators;
a sensor for sensing a location and an orientation of the pre-packaged tablet during a delivery wherein the sensed location and orientation of the pre-packaged tablet is used to modulate the differential drive based on at least one of a predetermined configuration within the processor and a dynamic configuration responsive to the sensed location and orientation;
a cutter mechanism and a cutter mechanism control logic wherein the cutter mechanism control logic is configured to:
monitor the sensed pre-packaged tablet location and orientation,
initiate a cutting sequence responsive to at least one of the predetermined configuration within the processor and the dynamic configuration responsive to determining an optimal sensed location and orientation;
generate and log a message into the distributed database responsive to the cutting sequence;
a sensor data collection system, wherein the collected sensor data is responsive to the user and stored in the distributed database; and
determine a change in healthcare outcomes based at least in part on the predictions associated with the healthcare outcomes; and
responsive to determining the change, generate a user intervention message to at least one of a patient, a caretaker, or a healthcare professional and request new biometric data.

14. The method of claim 13, wherein the patient data pipeline is configured to be located across one or more physical locations.

15. The method of claim 13, wherein the first healthcare system database is a warm path store or a cloud service.

16. The method of claim 13, further comprising responsive to generating the one or more predictions associated with one or more healthcare outcomes, authenticating a patient by at least one of a biometric verification process or a personal identification number.

17. The method of claim 16, wherein the biometric verification process is performed by at least one of retinal scanner and fingerprint scanner.

18. The method of claim 16, wherein generating the one or more predictions are responsive to a complication of the biometric verification process.

19. The method of claim 13, wherein the machine learning module is trained by communications with one or more data sets associated with the patient data pipeline.

20. The method of claim 13, wherein delivering the medication further comprises at least one of tearing, separating, pulling, and cutting the pre-packaged tablet from other pre-packaged tablets.

21. The method of claim 13, wherein the user interface is at least one of a display associated with the tablet delivery apparatus, a mobile device or a medical office display.

22. An integrated health management system, comprising:
a processor connected to a communications system and a memory wherein the memory stores a database, wherein the database is configured as a distributed database, wherein the distributed database is distributed across at least one of different physical locations, one or more processors located proximate to the processor, and a local network of interconnected processors, the processor coupled to a patient data pipeline, comprising:
a provisioning layer configured for system management, and
an application server comprising at least one sensor and one application operating in combination for the generation of first data;
a first healthcare system database within the patient data pipeline, the first healthcare system database configured to store the first data;
a second healthcare system database within the patient data pipeline, the second healthcare system database configured generate, based at least in part on the first data, transformed data; and
an actions module coupled to the patient data pipeline comprising:
a machine learning module configured to:
receive at least one of the first data or the transformed data as an input to output predictions associated with healthcare outcomes;
modify a delivery of a medication based at least in part by the predictions associated with the healthcare outcomes;
determine a change in healthcare outcomes based at least in part on the predictions associated with the healthcare outcomes; and
responsive to determining the change, generate a user intervention message to at least one of a patient, a caretaker, or a healthcare professional and request new biometric data; and
a tablet delivery apparatus configured to dispense the medication based at least in part on the predictions associated with the healthcare outcomes, wherein the delivery apparatus includes:
an input alignment guide to adjust pre-packaged tablets into the delivery apparatus,
a processor modulated differential drive for directional control of the pre-packaged tablets, wherein the differential drive comprises a dual motor drive system with independent actuators;

a sensor for sensing a location and an orientation of the pre-packaged tablet during a delivery wherein the sensed location and orientation of the pre-packaged tablet is used to modulate the differential drive based on at least one of a predetermined configuration within the processor and a dynamic configuration responsive to the sensed location and orientation;

a cutter mechanism and a cutter mechanism control logic wherein the cutter mechanism control logic is configured to:
- monitor the sensed pre-packaged tablet location and orientation,
- initiate a cutting sequence responsive to at least one of the predetermined configuration within the processor and the dynamic configuration responsive to determining an optimal sensed location and orientation;
- generate and log a message into the distributed database responsive to the cutting sequence;

a sensor data collection system, wherein the collected sensor data is responsive to the user and stored in the distributed database.

23. The integrated health management system of claim 22, wherein the first data includes biometric data and user intervention data.

* * * * *